(12) United States Patent
Wiener et al.

(10) Patent No.: US 8,409,166 B2
(45) Date of Patent: Apr. 2, 2013

(54) METHOD FOR PRESSURE MEDIATED SELECTIVE DELIVERY OF THERAPEUTIC SUBSTANCES AND CANNULA

(75) Inventors: Stephen M. Wiener, Boston, MA (US); Robert F. Hoyt, Jr., Boyds, MD (US); John R. Deleonardis, McLean, VA (US); Randall R. Clevenger, Mount Airy, MD (US); Robert J. Lutz, Olney, MD (US); Douglas V. Christini, North Brunswick, NJ (US); Brian Safer, Silver Spring, MD (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 0 days.

(21) Appl. No.: 13/094,764

(22) Filed: Apr. 26, 2011

(65) Prior Publication Data

US 2011/0263974 A1    Oct. 27, 2011

Related U.S. Application Data

(60) Continuation of application No. 12/009,646, filed on Jan. 17, 2008, now abandoned, which is a division of application No. 09/700,999, filed as application No. PCT/US99/11277 on May 21, 1999, now abandoned.

(60) Provisional application No. 60/086,565, filed on May 21, 1998, provisional application No. 60/087,099, filed on May 28, 1998.

(51) Int. Cl.
*A61M 31/00* (2006.01)

(52) U.S. Cl. ........................... 604/500; 600/431

(58) Field of Classification Search .............. 604/65–67, 604/96.01, 101.01–101.05, 103, 500, 506–510; 600/431
See application file for complete search history.

(56) References Cited

U.S. PATENT DOCUMENTS

| 3,952,742 | A | * | 4/1976 | Taylor ........................ 604/21 |
| 4,024,873 | A | | 5/1977 | Antoshkiw et al. |
| 4,531,936 | A | | 7/1985 | Gordon |
| 4,781,677 | A | * | 11/1988 | Wilcox ........................ 604/28 |
| 4,836,204 | A | | 6/1989 | Landymore et al. |
| 5,087,244 | A | | 2/1992 | Wolinsky et al. |
| 5,171,217 | A | | 12/1992 | March et al. |
| 5,211,624 | A | | 5/1993 | Cinberg et al. |
| 5,250,040 | A | | 10/1993 | Parks et al. |
| 5,282,785 | A | | 2/1994 | Shapland et al. |
| 5,470,350 | A | | 11/1995 | Buchholtz et al. |
| 5,484,412 | A | | 1/1996 | Pierpont |
| 5,514,088 | A | | 5/1996 | Zakko |
| 5,662,609 | A | | 9/1997 | Slepian |
| 5,674,192 | A | | 10/1997 | Sahatjian et al. |
| 5,720,720 | A | | 2/1998 | Laske et al. |
| 5,728,066 | A | | 3/1998 | Daneshvar |
| 6,369,039 | B1 | | 4/2002 | Palasis et al. |

FOREIGN PATENT DOCUMENTS

| EP | 0 321 614 | 6/1989 |
| FR | 2 659 239 | 3/1990 |
| WO | WO 94/15655 | 7/1994 |

OTHER PUBLICATIONS

Hoyt, Jr. et al., "Gallbladder Catheterization: A common Portal for Selectively Delivering Therapeutic Agents to Murine Hepatobiliary and Pancreatic Tissues," Contemporary Topics by the American Association for Laboratory Animal Science 35(4): 59, 1996 (Abstract only).*

Mann et al., "Pressure-mediated oligonucleotide transfection of rat and human cardiovascular tissues," *Proc. Natl. Acad. Sci. USA* 96:6411-6416, 1999.

Morrison et al., "High-flow microinfusion: tissue penetration and pharmacodynamics," *Am. J. Physiol.* 266:R292-R305, 1994.

Van den Bogacrde et al., "Intraductal Administration of Albendazole for Biliary Ascariasis," *American Journal of Gastroenterology* 92(9):1531-1533, 1997.

Clevenger et al., "Use of Fluorescent Latex Microspheres for Visual and Histologic Evaluation of Vector/Drug Delivery in Mice," *Con-*

*temporary Topics by the American Association for Laboratory Animal Science* 35(4): 59, 1996 (Abstract only).

DeLoenardis et al., "Digital Fluoroscopy: An Important New Tool for Developing Novel Gene Delivery Techniques in Mice," *Contemporary Topics by the American Association for Laboratory Animal Science* 35(4): 59, 1996 (Abstract only).

Wiener et al., "Manometric changes during retrograde biliary infusion in mice," *Am J Physiol Gastrointest Liver Physiol* 279:G49-G66, 2000.

Wiener et al., "Organ-Specific Gene Transfer to the Hepatobiliary Tree of Mice," *Contemporary Topics by the American Association for Laboratory Animal Science* 35(4): 60, 1996 (Abstract only).

\* cited by examiner

*Primary Examiner* — Theodore Stigell
(74) *Attorney, Agent, or Firm* — Klarquist Sparkman, LLP

(57) ABSTRACT

Methods and devices are disclosed for selective delivery of therapeutic substances to specific histologic or microanatomic areas of organs. Introduction of the therapeutic substance into a hollow organ space (such as an hepatobiliary duct or the gallbladder lumen) at a controlled pressure, volume or rate allows the substance to reach a predetermined cellular layer (such as the ephithelium or sub-epithelial space). The volume or flow rate of the substance can be controlled so that the intralumenal pressure reaches a predetermined threshold level beyond which subsequent subepithelial delivery of the substance occurs. Alternatively, a lower pressure is selected that does not exceed the threshold level, so that delivery occurs substantially only to the epithelial layer. Such site specific delivery of therapeutic agents permits localized delivery of substances (for example to the interstitial tissue of an organ) in concentrations that may otherwise produce systemic toxicity. Occlusion of venous or lymphatic drainage from the organ can also help prevent systemic administration of therapeutic substances, and increase selective delivery to superficial epithelial cellular layers. Delivery of genetic vectors can also be better targeted to cells where gene expression is desired. The access device comprises a cannula with a wall piercing tracar within the lumen. Two axially spaced inflatable balloons engage the wall securing the cannula and sealing the puncture site. A catheter equipped with an occlusion balloon is guided through the cannula to the location where the therapeutic substance is to be delivered.

39 Claims, 28 Drawing Sheets

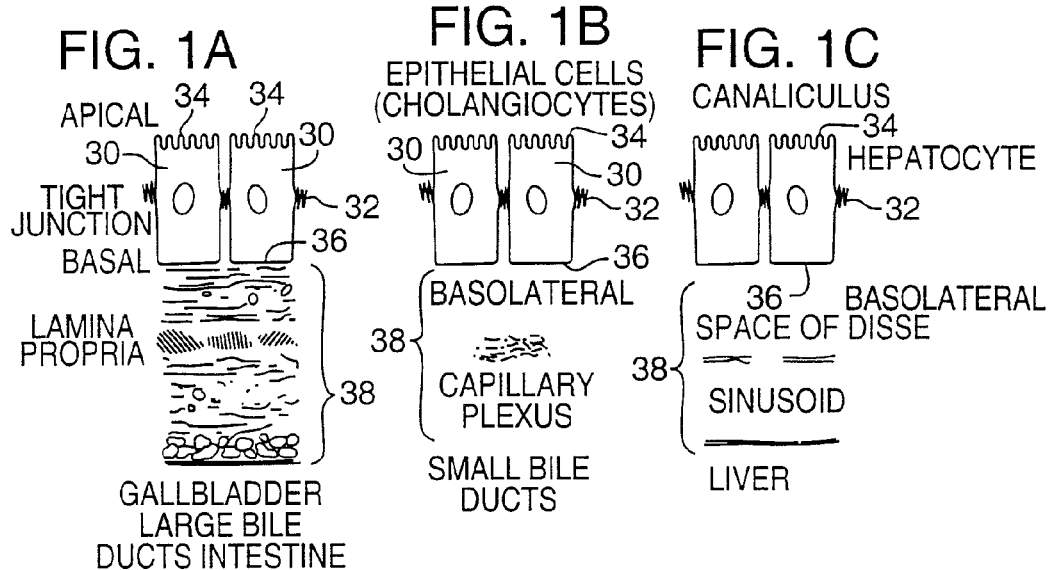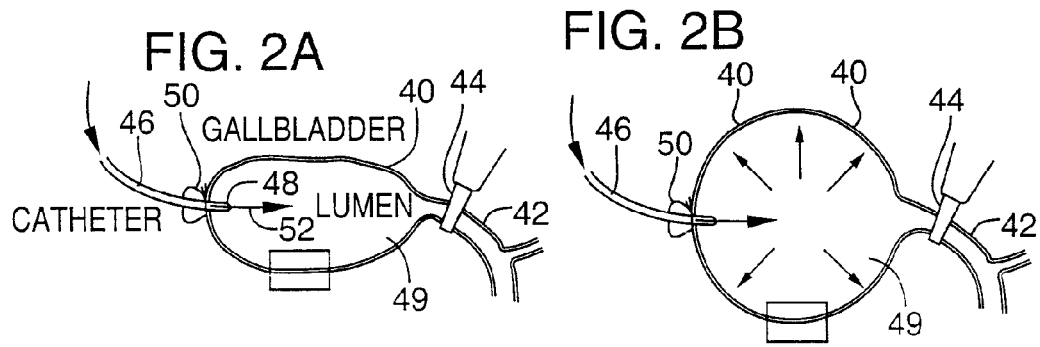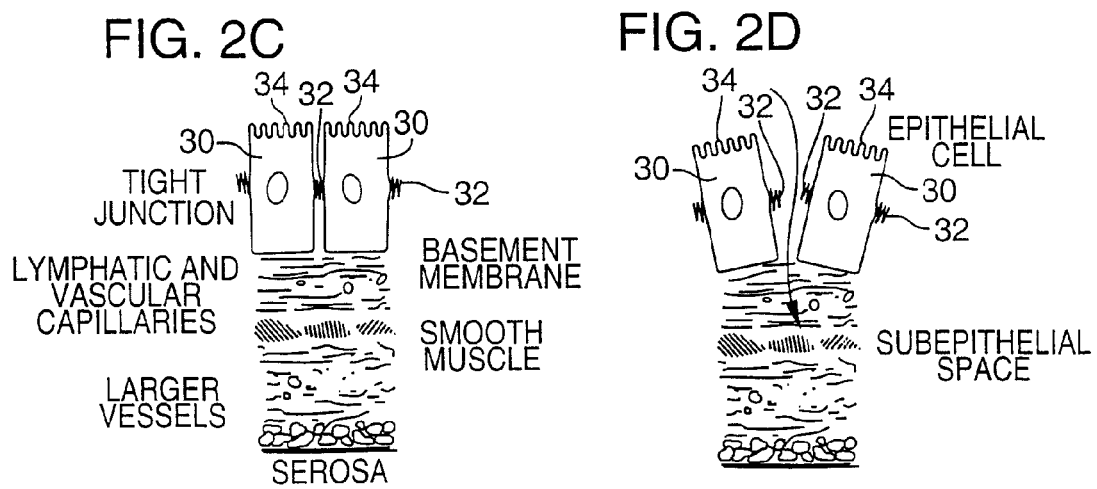

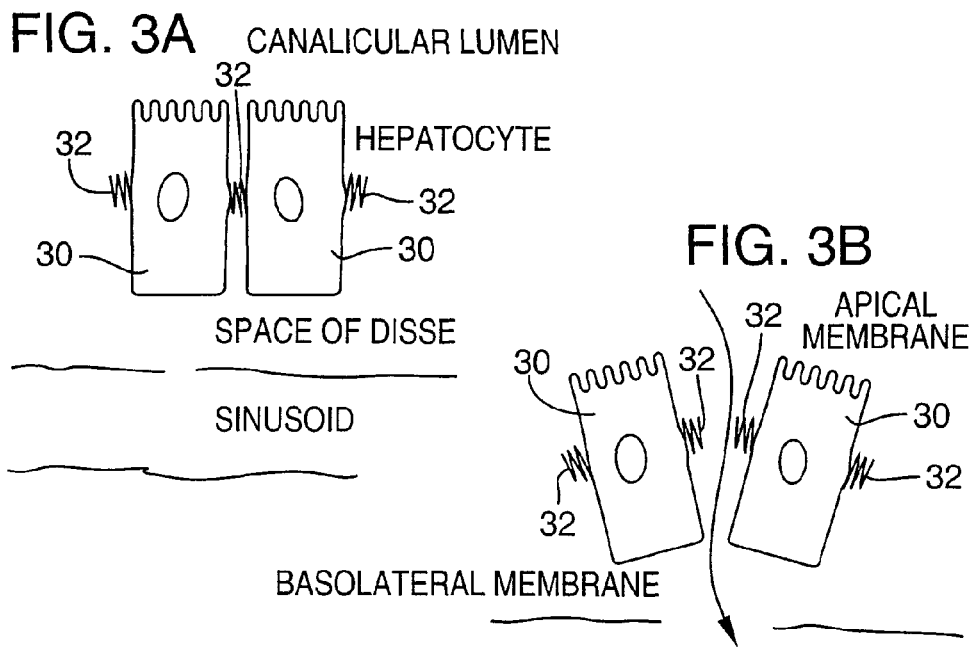
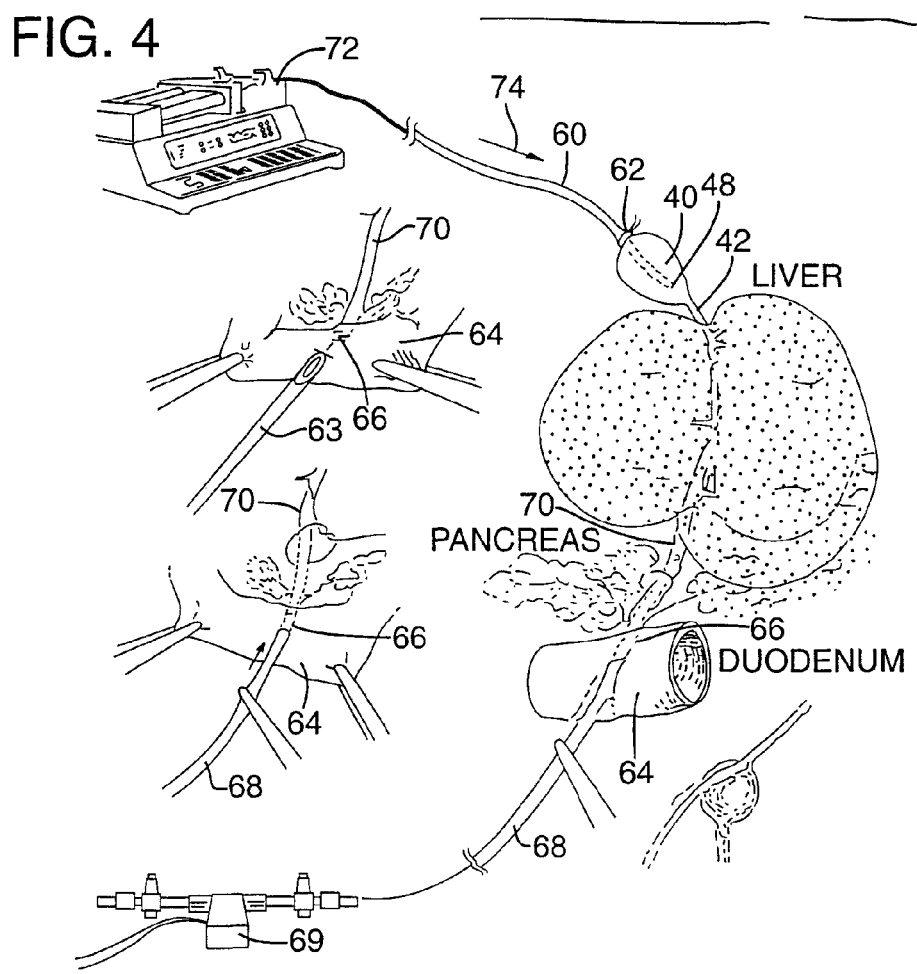

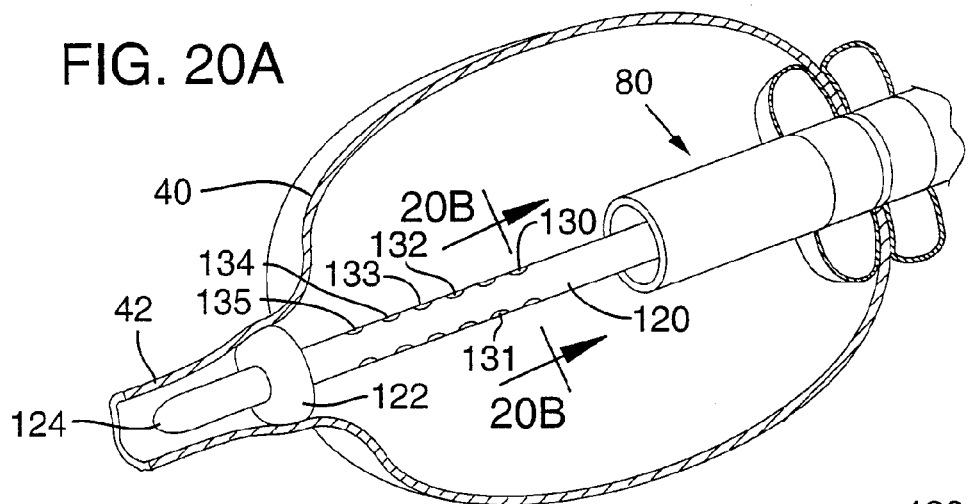
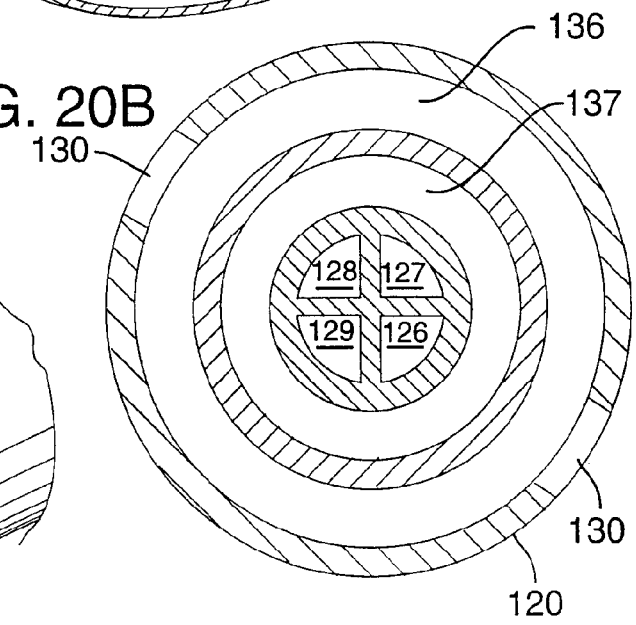
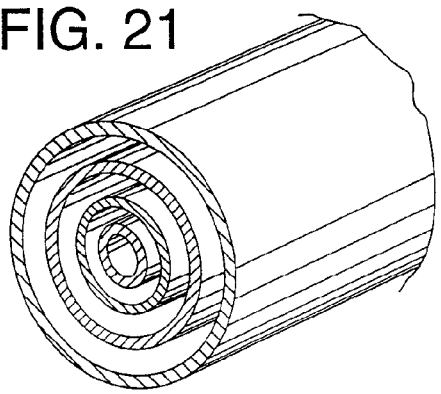
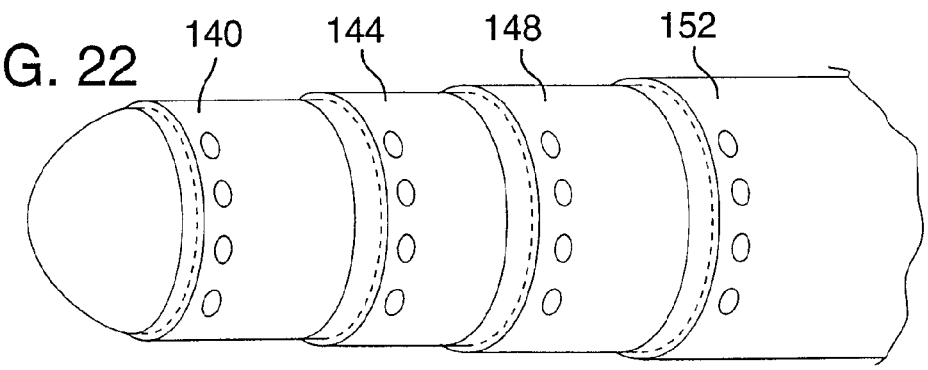

METHOD FOR PRESSURE MEDIATED SELECTIVE DELIVERY OF THERAPEUTIC SUBSTANCES AND CANNULA

This is a continuation of U.S. patent application Ser. No. 12/009,646, filed Jan. 17, 2008, now abandoned, which is a divisional of U.S. patent application Ser. No. 09/700,999, filed Dec. 4, 2000, (now abandoned) which is a §371 U.S. national stage of PCT/US99/11277, filed May 21, 1999, which was published in English under PCT Article 21(2), which in turn claims the benefit of U.S. Provisional Application 60/086,565, filed May 21, 1998 and U.S. Provisional Application No. 60/087,099, filed May 28, 1998, all of which are incorporated herein in their entirety.

FIELD OF THE INVENTION

This invention concerns selective delivery of therapeutic agents, such as drugs or genetic vectors, to specific organs, tissue compartments or cell types.

BACKGROUND OF THE INVENTION

Local delivery of therapeutic agents to target organs or tissues is a very desirable technique for delivering drugs with minimal side effects. U.S. Pat. No. 5,087,244 is an example of such targeted drug delivery, in which an endovascular catheter has a flexible balloon that is inflated to contact the internal walls of the vessel. A drug is then delivered through minute holes in the balloon, which is in intimate contact with the walls of the vessel. U.S. Pat. No. 5,282,785 discloses another endovascular drug delivery catheter, in which an expandable balloon brings a perforated drug delivery portion of the catheter into intimate contact with a radially restricted portion of the vessel wall, for transmural delivery of drugs through the contiguous catheter and lumen wall. See also U.S. Pat. No. 5,662,609, according to which a catheter with a pair of expandable balloons is used to isolate a portion of a blood vessel between the balloons for treatment via infusions, and U.S. Pat. No. 5,674,192, in which a single expandable balloon is used to contact a portion of vessel wall for treatment.

U.S. Pat. Nos. 4,781,677 and 5,514,088 both disclose treatment of gallstones by direct infusion of a solvent (such as methyl tertiary butyl ether) into the gallbladder through a catheter positioned in that organ.

U.S. Pat. No. 5,720,720 discloses high flow microinfusion of drugs (such as chemotherapeutic agents) into the brain parenchyma. Using this approach, a catheter is inserted into a brain tumor, and a chemotherapeutic agent is introduced through the catheter at a sufficient flow rate to cause rapid diffusion of the substance throughout the relatively homogenous, porous medium of the brain.

None of these methods or devices, however, discloses selective delivery of therapeutic substances (such as drugs and DNA vectors) to specific microanatomic regions or cell types in an organ. This is a significant drawback because many diseases involve abnormalities that are restricted to particular microanatomic or cellular regions. General systemic delivery of a therapeutic substance at a sufficient concentration to reach this localized region can cause widespread toxicity. General systemic delivery of drugs and gene therapy vectors can also be much less effective than site directed delivery, because selected delivery introduces the drug or vector directly into the tissue where it is to act. Site specific delivery can be accomplished to a certain degree by use of tissue-specific ligands, but the availability of identified ligands, and the degree of specificity of known ligands, may be insufficient to prevent negative systemic effects. The discovery and design of such ligands is also a complex, time-consuming and expensive process.

It is thus an object of the present invention to provide improved regional and tissue- or cell-specific delivery of therapeutic (including diagnostic) agents.

SUMMARY OF THE INVENTION

Improved regional-, organ-, tissue-, and cell-specific delivery of therapeutic agents is achieved via infusion of therapeutic agents into body lumens (such as the gallbaldder or hepatobiliary ducts, gastrointestinal tract, genitourinary tract, trachea, arteries, veins, or other ductular sites) under controlled pressures. In particular, it has been found that delivery of liquid agents to specific histological depths in the walls of the lumen (for example walls of an organ space) can be achieved by controlling the conditions (such as pressure/flow rate/volume) under which the agent is delivered to the lumen. Administration of the agent into a closed region of the hollow organ that is capable of being pressurized, at relatively low pressures, permits specific delivery of the agent to superficial layers of the organ, such as the apical surface of epithelial cells. Administration of the agent at least initially above a threshold higher pressure/flow rate/volume can disrupt microanatomic barriers, and selectively deliver the agent to deeper layers, such as the subepithelial space. Delivery into the subepithelial space permits access of the agent to the basal surface of the cell and other anatomic structures (such as the vascular sinusoids in the liver). Local administration of the drug in accordance with this invention can therefore permit site (and even cell type) specific drug delivery.

One aspect of the invention is a method of determining conditions (such as pressures and flow rates) at which delivery of an agent is directed to specific cell types or depths, such as the apical surface of superficial epithelial cells or a subepithelial space. In the case of a vascular site, delivery would be to the apical surface of endothelial cells or to specific tissue compartments such as the vascular intima or media. In certain embodiments, this method involves isolating a closed organ space (such as the lumen of the gall bladder, the hepatobiliary tree, or a parotid or pancreatic duct) so that it forms a closed pressure system. A test fluid having a preselected viscosity (such as liquid saline) is then introduced into the closed system at a preselected flow rate (or in a preselected volume) to determine a threshold pressure at which microanatomic barriers (such as tight junctions between cells) in the closed system are disrupted. A therapeutic substance may then subsequently be administered as part of a fluid flow during which the peak pressure is not exceeded, to substantially avoid subepithelial or systemic administration of the substance. Alternatively, the peak pressure may be exceeded to purposefully administer the substance to subepithelial (including systemic) regions.

In other embodiments, a first administration of a test fluid is followed by a second administration of the test fluid to determine a second peak pressure (which is lower than the first peak pressure). The therapeutic substance is then administered into the organ as part of a fluid flow during which the second peak pressure is not exceeded, to achieve optimum avoidance of systemic administration of the drug. Alternatively, the therapeutic substance is administered into the organ space as part of a fluid flow during which the second peak pressure is equaled or exceeded, to achieve selective systemic administration. In particular embodiments, in which the hollow organ is the hepatobiliary tract, selective administration during which the peak pressure is not exceeded will selectively direct the substance to cholangiocytes (epithelial cells that line the tract), while selective administration in a flow during which the peak pressure is equaled or exceeded will also direct the substance to the hepatocytes and to the sinusoids in the liver (by movement of the substance through disrupted microanatomic structures such as tight junctions that separate the lumen of the tract from the subepithelial space).

Another aspect of the invention is a method of delivering agents to a hollow, pressurizable organ cavity, such as the interior of a hollow viscus or the lumen of a duct, at a controlled or preselected pressure, that selectively targets either superficial internal cells (such as the apical surface of a polarized epithelium), or deeper histological regions (such as the subepithelial space) substantially without damaging the cells or causing significant systemic delivery of the agent. In particular embodiments, the preselected pressure is only slightly above a normal, physiologic intralumenal pressure, and is below the first pressure peak threshold (or in more specific embodiments below the second pressure peak threshold). The delivery pressure may be, for example, no more than about 2-5 mm Hg above the normal physiologic intralumenal pressure to achieve specific epithelial delivery. In certain embodiments, for non-vascular delivery the constant pressure is 5-100 mm Hg (for example 25-75 or about 50 mm Hg, or at least 5, 25, 50 or 100 mm Hg), and for vascular delivery the constant pressure is 5-400 mm Hg (for example 5-200 mm Hg, 5-100 mm Hg, or at least 5, 25, 50 or 100 mm Hg). In specific embodiments, the delivery pressure is below a threshold pressure for disruption of microanatomic structures such as tight junctions between the epithelial cells that inhibit access of the agent to the subepithelial space under normal physiological conditions.

In another embodiment, a fluid is administered at a defined constant infusion pressure selected to insure that the infusate is confined to the intralumenal space. Alternatively, a constant infusion pressure may be selected that will insure that tight junction disruption occurs to thereby permit delivery to subepithelial or subendothelial tissue compartments along an intralumenal-subepithelial or intralumenal-subendothelial pressure gradient. The use of pressure gradients to deliver therapeutic agents is particularly useful because diffusion limits the distribution of large macromolecules and thereby interferes with the effective delivery of drugs and other potentially therapeutic agents to targeted sites. Alternatively, very high uncontrolled pressure result in a substantially ballistic delivery of drugs or particles, that can be traumatic to the tissue that is being treated. A particular embodiment of the present invention is the use of a controlled pressure gradient to selectively deliver non-particulate molecules (such as molecules up to 500 nm in diameter) to subepithelial or subendothelial tissue compartments. Pathways through which molecules may move can, as disclosed in the present invention, be created through the use of constant rate or constant pressure administration to open tight junctions. Alternatively, such pathways may be created or facilitated by known methods, such as pharmacological or electrical disruption, and then utilized with the present invention to permit more effective delivery of a therapeutic agent to subepthelial or subendothelial tissue compartments. An example of pharmacological creation of a pathway through which molecules may move along a pressure gradient is the use of Zona Occludens Toxin (See U.S. Pat. Nos. 5,864,014, 4,827,534, and 5,664,389 for information on Zona Occludens Toxin).

In vascular surgery creating an anastomosis between two vessels is often complicated by a disparity in diameter between the donor and recipient vessels. Similarly, surgical reversal of a vasectomy or an ovarian tubal ligation is complicated by having to locate portions of the vas deferens or fallopian tubes that are sufficiently wide to permit effective rejoining. A mechanism for achieving expansion of tubular structures would therefore be clinically useful and helpful. Devices of the present invention can be used to expand a tubular structure (such as a blood vessel or duct) or viscus to a predetermined cross-sectional target diameter. Such expansion can be performed either in vivo or ex vivo, with subsequent anastomosis between donor and recipient structures. In another embodiment of the invention, this expansion is combined with continuous intralumenal infusion of drugs, genetic vectors, or other therapeutic agents to the donor and/or recipient structures.

Utilization of pressure to deliver molecules to different histological compartments occurs through creation of a pressure gradient, particularly a controlled gradient that is selected to direct the delivery of the molecules to a preselected site (such as a specific histological layer) in an organ. This gradient involves the establishment of a controlled pressure difference between two compartments of a structure. Thus in the case of a luminal or ductular structure, a pressure gradient may be created between the lumen of the tube and deeper structures. In the case of a epithelial organ or duct this pressure gradient may be created between the apical membrane surface of the epithelial cell and the lamina propria or the serosa. In the case of a vascular structure this pressure gradient may be created between the apical membrane surface of the endothelial cell and the smooth muscle layer or the adventitia. The pressure gradient may consist of the application of a higher pressure within the lumen than is present in the deeper structures, or alternatively may consist of the application of higher pressure on the outside of the structure than exists on the inner portions of the structure. This invention specifically embodies the creation of either type of pressure gradient, so that infusate may be driven from the inside of a structure to the outside, or from the outside towards the inside of the structure. The latter embodiment is of particular use in structures that have discrete lumens (vessels, trachea, gastrointestinal tract, urinary bladder, etc.) as well as those that do not (for example, nerves). The pressure can be applied by an external cuff placed around the anatomical structure, to isolate and pressurize an external surface area (such as a complete circumferential region) of the structure.

Just as application of an elevated intralumenal pressure may also be used to increase uptake and transport by epithelial or endothelial cells, so too, application of an elevated external pressure may also be utilized to increase uptake and transport by external surface cells, such as, for example, adventitia, serosa, epineurium, etc. Specific devices are described in this invention that permit establishment of either kind of pressure gradient.

Another aspect of the invention is that the administration of agents at volumes/pressures substantially below the baseline (physiologic) intralumenal volume/pressure (for example the physiologic pressure of a gallbladder in which the cystic duct has been occluded) will result in only minimal (or no) delivery to epithelial cells. Intralumenal pressure can be reduced below physiological levels by introducing a catheter into the organ, and suctioning the fluid (such as bile) from the organ. As pressure/volume are increased toward baseline intralumenal volume/pressure (e.g. the pressure immediately after occlusion and suction of the liquid contents of the organ, such as the bile in the gallbladder), delivery to epithelial cells will increase. When pressure/volume is substantially above the baseline volume/pressure, then subepithelial delivery will occur.

According to another aspect of the invention, a therapeutic substance (such as a non-particulate organic compound) is delivered by infusion into a body lumen lined with epithelial cells, while infusion parameters (such as flow rate, pressure, and volume) are controlled so as to selectively result in delivery of the therapeutic substance either to the superficial cells, or to the subepithelial space and cells as well. Appropriate infusion control may be achieved in various ways. For example, infusion may be performed only at a specified pressure (e.g. pressure increase with respect to a baseline), or only at a pressure within a specified range, with the specified pressure selected either to maximize or to avoid delivery to the subepithelial space. Similarly, infusion may be performed at a given flow rate, until a specific threshold (such as a peak) pressure is reached, which may be maintained for a desired interval. Once the peak pressure is reached, and microanatomic disruptions occur, pressure tends to decline and plateau, even as the infusion continues at the same flow rate. Infusion may also be controlled by infusing a specified volume at a specified rate such that the lumen is either filled sufficiently for delivery to only superficial cells, or is overfilled sufficiently for delivery to deeper spaces and cells.

There are also instances in which systemic delivery of drugs via high pressure infusion is desired. The method of the invention could be used as a substitute for invasive vascular procedures, such as direct intra-arterial delivery of chemotherapeutic substances. Instead of intravascular delivery (and the attendant problem of thrombosis), direct delivery to organs can be achieved by introduction of the agent into a hollow, pressurized viscus or duct (such as the hepatobiliary tree or parotid duct) at a pressure that is intended to provide subepithelial delivery. Avoidance of intravascular administration (as in hepatic artery infusion) for targeted delivery eliminates the problems of endothelial damage and attendant morbidity, while also avoiding the more widespread systemic delivery that is inherent when any drug is delivered directly into the cardiovascular system. It is also possible to combine intrabiliary delivery with temporary occlusion of venous or lymphatic drainage, to further isolate the organ and prevent widespread systemic administration of a drug, even when it is introduced at a sufficient pressure to provide subepithelial delivery of the drug.

Particular control parameters may be established in various ways. For example, a baseline volume or threshold pressure of a body lumen may be established through measurements in a sample population at predetermined infusion rates. The baseline as measured may be further correlated with demographic data such as height and weight. Infusion is then controlled in accordance with these predetermined variables, for example by introducing specified volumes at selected flow rates that are predicted to exceed (or not exceed) a threshold pressure at which microanatomic disruption occurs.

In another embodiment, an inert infusate may be used first to establish a critical pressure at which delivery to spaces deep to the surface cells begins. In this embodiment, an inert infusate is infused into a given body lumen at a given rate, and the intralumenal pressure is tracked until a pressure threshold peak is reached and passed, at which time infusion is stopped. The infusion of inert infusate may then be repeated at least once, and the peak pressure again measured. The last-measured peak pressure is then taken as the pressure level at which infusate will begin to enter the space deep to the surface cells. If delivery only to surface cells is desired, infusion of the therapeutic agent then proceeds via an infusion during which the last-measured peak pressure is not exceeded. If delivery to spaces and cells deep to the superficial cells is desired, infusion of the therapeutic agent proceeds via an infusion during which the infusion pressure, at least early in the infusion, meets or exceeds the last-measured peak pressure.

According to another aspect of the present invention, the delivered therapeutic substance may be a drug. Significant examples include chemotherapy agents, anti-inflammatory drugs, and any agent having potentially undesirable systemic effects (including cancer chemotherapeutic agents such as cytoxan, and treatments for hepatic biliary cirrhosis requiring administration of corticosteroids). Alternatively, the therapeutic agent may be a DNA vector for use in gene therapy, such as an adenoviral vector that carries a gene for correcting a genetic disorder, such as cystic fibrosis. The vector may also be specifically targeted to particular cells, including (a) the epithelial cells or to the subepithelial cells (or both); (b) endothelial cells, foam cells of an atherosclerotic plaque, and/or smooth muscle cells; (c) cells of the external surface layer of a structure and/or deeper cells (or both); (d) nerve cells or glial cells; or other celltypes within a structure, thus providing additional specificity. The vector may even be targeted specifically to receptors found only on particular surfaces of certain polar cells (such as the basal or apical surfaces of polar epithelial cells), such that the vector is taken up by the certain polar cells only if delivery is made to the space adjacent the particular surface.

One useful embodiment of the present invention is for apical epithelial or cholangiocyte-specific delivery of genetic material in the hepatobiliary system at relatively low, sub-threshold delivery pressures. Such superficial delivery of therapeutic substances is particularly desired in diseases such as primary biliary cirrhosis, sclerosing cholangitis, and AIDS associated biliary tract diseases such as MAI and cryptosporidium infection. Alternatively, at higher supra-threshold pressures, combined hepatocyte and cholangiocyte delivery may also be performed, or even delivery to the subepithelial layer (such as the lamina propria in the case of the larger intra- and extrahepatic bile ducts, or to the Ito, Stellate, Kuppfer, or other subepithelial cells in the liver). Deeper penetration would be desired, for example, in diseases such as hepatocellular carcinoma and hepatic fibrosis where the therapeutic agent is targeted for hepatic tissue. In the case of cholangiocarcinoma it may be efficacious to target both cholangiocytes as well as deeper subepithelial celltypes. Outside the biliary system, directed subepithelial delivery could be used for treatment of diseases such as Crohn's disease, where delivery of anti-inflammatory agents to the lamina propria would be desired. Similarly, directed subepithelial delivery of chemotherapeutic agents such as cytoxan or pro-inflammatory agents such as interleukin-8 (IL-8) could be used in the treatment of urinary bladder carcinoma.

Delivery confined to a particular inner or outer layer may also be useful in certain circumstances. For example, intralumenal delivery confined to the cells lining the lumen of a viscus or other ductular structure (epithelial cells) or vascular structure (endothelial cells) may be useful. An example of delivery to just the epithelium would be the administration of a pro-inflammatory agent such as interleukin-8 (IL-8) targeted to just epithelial cells, in the treatment of certain malignant conditions. Similarly, delivery confined to endothelial cells may be used in the treatment of certain vascular disorders.

Another aspect of the invention includes an access cannula and catheter or access port for targeted delivery of therapeutic agents. The cannula includes distal and proximal ends, and contains a lumen configured to contain a sharp tipped trochar that penetrates the wall of a desired body lumen, for example the wall of a hollow organ such as the gallbladder or intestine.

The cannula further includes a pair of balloons spaced axially along the cannula, so that after inflation the two balloons engage opposing inner and outer faces of the organ. After the inner balloon is inflated, the catheter is withdrawn slightly until the first balloon is snug against the interior wall of the body lumen. The second balloon is then inflated while sufficient tension is maintained to keep the first balloon snug against the interior wall of the body lumen. The two inflated balloons thus press against the interior and exterior surfaces of the wall of the body lumen, keeping the catheter in place and sealing against leaks.

The process of the present invention may include sealing, evacuating and rinsing the targeted body lumen, followed by infusion of the therapeutic substance under controlled conditions as above. After infusion, any remaining infusate may be aspirated, further reducing potential systemic effects.

Pressure itself may also facilitate cell transport processes and this may be utilized for improved delivery. For example, constant rate and constant pressure intralumenal infusion may be utilized to enhance uptake via the apical membrane surface of epithelial and/or endothelial cells. Alternatively, constant rate and constant pressure intralumenal infusion may also be utilized to enhance transcytosis of molecules from the apical to basal or basolateral cell surface.

A particular embodiment of the present invention is the use of constant pressure intralumenal delivery in combination with methods for measuring the expansion of a viscous, duct, or vessel. Such methods may include the use of intralumenal ultrasound, which has been described for the evaluation of tissue compartment diameters. Intralumenal ultrasound or other methods may be combined with pressure-mediated delivery to permit evaluation of the depth of delivery of a therapeutic agent.

In another embodiment of the invention, constant pressure administration may be used to compress the inner surface layer of a luminal structure, such as a atherosclerotic plaque in a blood vessel. Very high intralumenal pressures may be used also to cause epithelial or endothelial denudation.

BRIEF DESCRIPTION OF THE DRAWINGS

FIG. 1 is a schematic view of the epithelial cells that line the gallbladder (A), the small bile ducts (B), and the liver (C).

FIGS. 2A and 2C are schematic views of site specific delivery to the apical surface of an epithelial cell in a gall bladder at relatively low biliary pressures; FIGS. 2B and 2D show site specific delivery to the subepithelial space at higher biliary pressures.

FIG. 3A is a schematic view of site specific delivery to the apical surface of a hepatocyte in the liver at relatively low, subthreshold hepatobiliary pressures, while FIG. 3B is a schematic view of delivery to the subepithelial layers once the threshold pressure is exceeded.

FIG. 4 is a schematic view of a system for infusing liquid under pressure into the closed ductular system of the hepatobiliary tree, for site specific delivery of drugs and other agents.

FIG. 20A is a view similar to FIG. 19, showing a multi-lumen catheter inserted in the gallbladder for pressure controlled multiple rinsing and draining of the gallbladder.

FIG. 20B is a cross-section through the catheter of FIG. 20A, showing the multiple channels of the catheter, and their fluid connections to the exterior of the catheter.

FIG. 21 is a view of a tip of an alternative embodiment of the catheter in which there are multiple concentric delivery channels through the catheter.

FIG. 22 is a view of an alternative embodiment of the catheter in which a series of bands on the catheter have small openings through which to introduce material into the gall bladder, and through which to drain it.

DETAILED DESCRIPTION

Figure 5A:
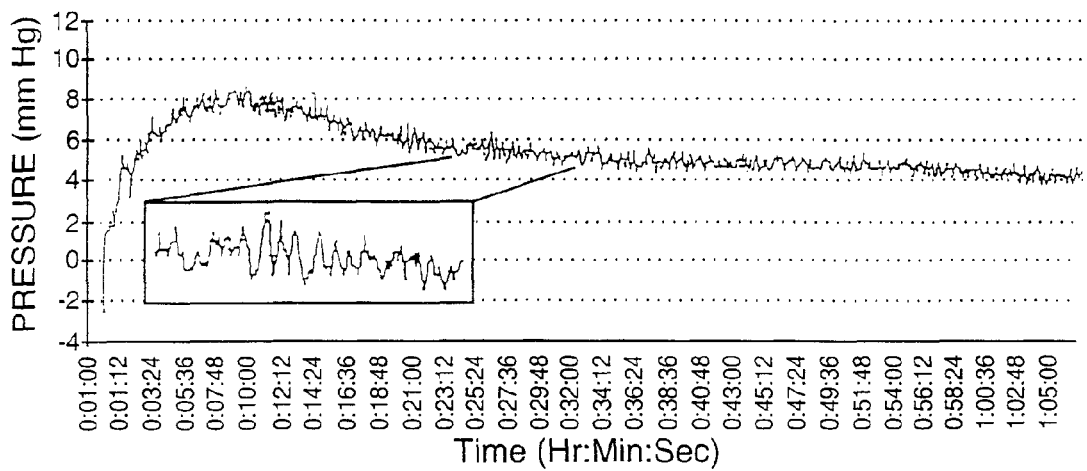
FIG. 5 is a graph showing measured intrabiliary pressure after occlusion of the comon bile duct in a single animal (FIG. 5A), and in a group of animals (FIG. 5B).

The present invention is a method of specific delivery of agents (such as therapeutic or diagnostic drugs) into pressurized body cavities, such as the lumen of an organ, including a hollow viscus (e.g. gallbladder, small intestine) or a duct (e.g. the ducts of the salivary, parotid or hepatobiliary systems). The body cavities are anatomically, manometrically isolated (for example by occluding one or more ducts from the organ that communicate with the gastrointestinal tract). An agent to be delivered is then introduced by an infusion into the isolated body cavity either above or below a threshold pressure/flow/volume at which transepithelial delivery of the agent occurs. Hence agents delivered below this threshold are delivered preferentially to the cells of a superficial epithelial lining, while agents delivered above this threshold are also delivered to the subepithelial space (which can include periductular or even systemic vascular administration, for example through the sinusoids of the liver).

Many cavitary organs in the body (such as the gall bladder, hepatobiliary ducts, parotid ducts, and gastrointestinal organs) contain epithelial cells that are lined by polarized epithelial cells. These cells are "polarized" in the sense that they have an apical surface facing the lumen, and a basal surface which is substantially isolated from the lumen by tight junctions between the epithelial cells. The surfaces of these polar cells are often specialized for unidirectional passage of biological substances through the cell, for example for delivery into the lumen.

FIG. 1 shows schematic cross-sections of the histological architecture of several different classes of tissue, FIG. 1A shows the architecture common in gallbladder, large bile ducts and intestine, in which polarized epithelial cells 30 are joined to one another by tight junctions 32, which isolate the apical surfaces 34 of the cells 30 from a basal cellular surface 36 and a subepithelial space 38 having a lamina propria. The architecture of the small bile ducts in FIG. 1B illustrates that the epithelial cells (called cholangiocytes in these bile ducts) have a subepithelial space that is occupied by a capillary plexus, but does not have a lamina propria. FIG. 1C shows that in the liver, the subepithelial space 38 is occupied by the Space of Disse and the sinusoids of the liver, but no lamina propria.

Regardless of the subepithelial anatomy, tight junctions between epithelial cells form a physical and functional barrier between the lumen and the subepithelial space. Therefore, in all of these structures there are at least two sites that can be targeted for drug delivery: the epithelial cells that line the luminal space and the spaces (and their cellular and other structures) located deep to the epithelial cells. Endothelial cells lining body cavities and ducts other than those specifically discussed can also be the target of pressure directed delivery of agents in accordance with this invention. However for purposes of illustration, pressure directed delivery will be illustrated in the hepatobiliary tree.

FIG. 2A schematically illustrates a gall bladder 40 having a cystic duct 42 which is occluded by a clip 44. A catheter 46 has been introduced through the wall of gallbladder 40 so that the distal tip 48 of catheter 46 is present in the lumen 49. A positioning/sealing device 50 around catheter 46 helps retain the catheter in position, and assists in sealing the opening through which catheter 46 has been introduced. Arrow 52 illustrates delivery of a liquid (such as a drug) under relatively low pressure conditions, in which case the tight junctions are not disrupted (FIG. 2C), and delivery occurs substantially completely to the apical surface of the epithelial cell. FIG. 2B, in contrast, shows delivery of a liquid medium into gallbladder 40 under relatively high pressure conditions that disrupt tight junctions 32 (FIG. 2D) and permit access of the liquid medium to the subepithelial space.

FIG. 3A illustrates delivery of an agent to the apical surface of the epithelial cell in the liver under low pressure delivery conditions, while FIG. 3B illustrates disruption of microanatomic structures such as the tight junctions, which allows delivery to the subepithelial Space of Disse and the sinusoids in the liver under relatively higher pressure delivery conditions.

Systematic evaluation of the manometric and histological consequences of retrograde biliary infusion in mice was conducted using (i) a novel system for simultaneous cholangiomanometry; (ii) digital fluoroscopic evaluation of the distribution of radioopaque dye; (iii) histological evaluation of the distribution of fluorescent latex microspheres of sizes comparable to adenoviral and liposomal vectors; and (iv) histological evalution of the pattern of gene transfer obtained following administration of a recombinant adenoviral vector. These evaluations, which illustrate several different embodiments of the invention, are described in the following examples.

EXAMPLE 1

Delivery Device and Infusion Data

FIG. 4 illustrates an apparatus used for demonstrating the effect of retrograde biliary infusion on intrabiliary pressure, and the site specific delivery of agents to the cells. Twenty to forty gram anesthesized CD-1 male mice (Charles River) were used as experimental subjects. Following a midline laparotomy, the gallbladder 40 was manually drained through the cystic duct 42. A cholecystotomy catheter 60 (silastic tubing, 0.012" ID/0.025 OD) was introduced through the wall of the gallbladder 40, and secured within the gallbladder lumen with the catheter tip 48 advanced so that it was immediately proximal to the junction with the cystic duct 42. An absorbent cellulose (X0-Med, Jacksonville, µl) packing 62 was packed around the entrance site of the catheter into the gallbladder to prevent bile from leaking into the peritoneum.

A twenty-three gauge needle 63 was used to make an opening in the duodenum 64 and to perform a sphincterotomy on the Sphincter of Oddi 66 (which helps control passage of bile into the small intestine). A polyethylene tubing catheter 68 for recording intrabiliary pressure (ID 0.011", OD 0.024") was inserted through the duodenal opening and advanced through the Sphincter of Oddi 66 into the common bile duct 70. The catheter 68 was then advanced so that its tip could be visualized imediately rostral to the junction with the superior pancreatic duct. Preplaced 6-0 silk ties were used to secure the catheter in position. Since the biliary tree is a closed ductular system, the pressure recorded in the common bile duct (by a pressure transducer 69) accurately reflected the pressure throughout the entire hepatobiliary system (the ducts and canaliculi through which bile flows). Intrabiliary pressure was continuously recorded every 0.5-2.0 seconds using a low pressure transducer (Digimed, Indianapolis) and a personal computer.

Figure 5B:
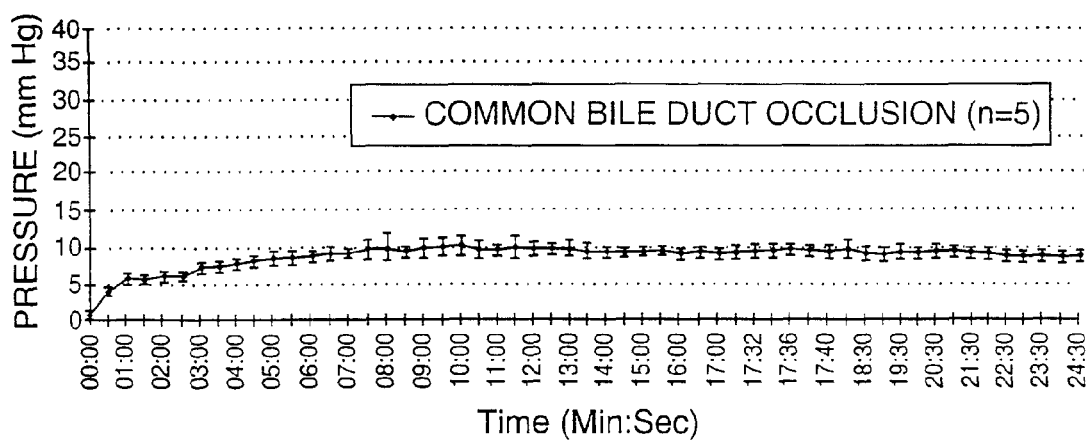

Retrograde biliary infusions were administered by using the cholecystotomy catheter 60 and a microinfusion pump 72 (Harvard). Infusions traveled in a normograde direction 74, moving sequentially down the cystic duct 42 and common bile duct 70 until the tip of the pressure catheter 68 was reached. Since the pressure catheter prevented further normograde flow, the infusate then reversed direction and moved up the hepatic duct towards the liver. Hence infusions through the catheter 60 into the gallbladder 40 permitted delivery of the infusate throughout the hepatobiliary system, including the ducts and canaliculi of the liver. Baseline measurements of intrabiliary pressure were continuously recorded for 25 minutes during common bile duct occlusion with no retrograde biliary infusion. Since bile was still being formed, the intrabiliary pressure gradually rose from a baseline of $0.8\pm0.2$ mm Hg (n=5) reaching a mean pressure of $10.0\pm1.4$ mm Hg by 10 minutes (FIG. 5). This pressure remained fairly constant for at least 25 minutes, when recording was discontinued.

Figure 6:
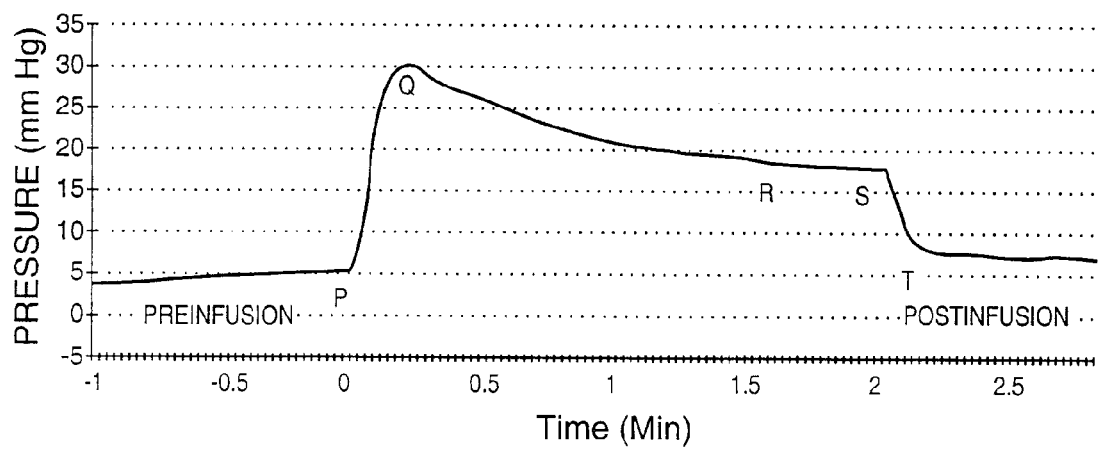
FIG. 6 is a graph showing measured intrabiliary pressure during infusion after occlusion of the common bile duct, indicating pressure change as a function of time at an infusion rate of 240 per 2 minutes.

Retrograde biliary infusions at various constant infusion rates resulted in a characteristic pattern of pressure changes, which is illustrated in FIG. 6. There was a progressive rise at P in intralumenal pressure until a peak pressure Q was reached, followed by a slight decline in pressure, and then a plateau pressure R that was substantially sustained until the infusion was completed. Once the infusion was stopped at S, pressure immediately underwent a rapid decline T toward the preinfusion value. Hence the pressure reached a threshold at Q where microanatomic barrier structures were physiologically disrupted, so that the infusate could more readily escape from the gallbladder during the lower plateau R.

Figure 7:
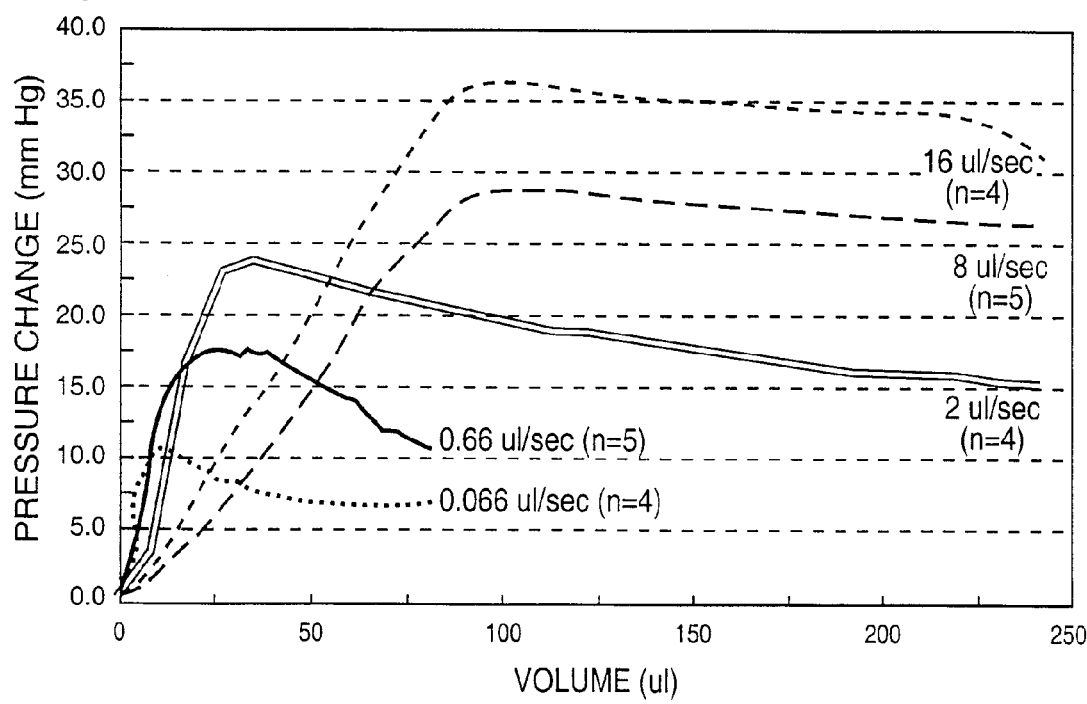
FIG. 7 is a graph similar to FIG. 6, but showing mean intrabiliary pressure as a function of volume infused, for infusion rates of 0.06, 0.66, 2.00, 8.00 and 16.00 µl/sec of 0.9% NaCl.

FIG. 7 shows that the intrabiliary pressure changes as a function of volume with varying infusion rates, hence pressure changes (and threshold pressures) were dependent upon the infusion rate and volume. Greater peak pressures were achieved with faster infusion rates. The pressure rose more rapidly with time at the higher infusion rates, and the initial slope of the pressure-volume curve during the filling phase of the infusion tended also to vary with infusion rate, being lower at the faster infusion rates. The peak pressure (which is an example of a particular type of threshold event) was also higher for higher infusion rates.

Figure 8A:
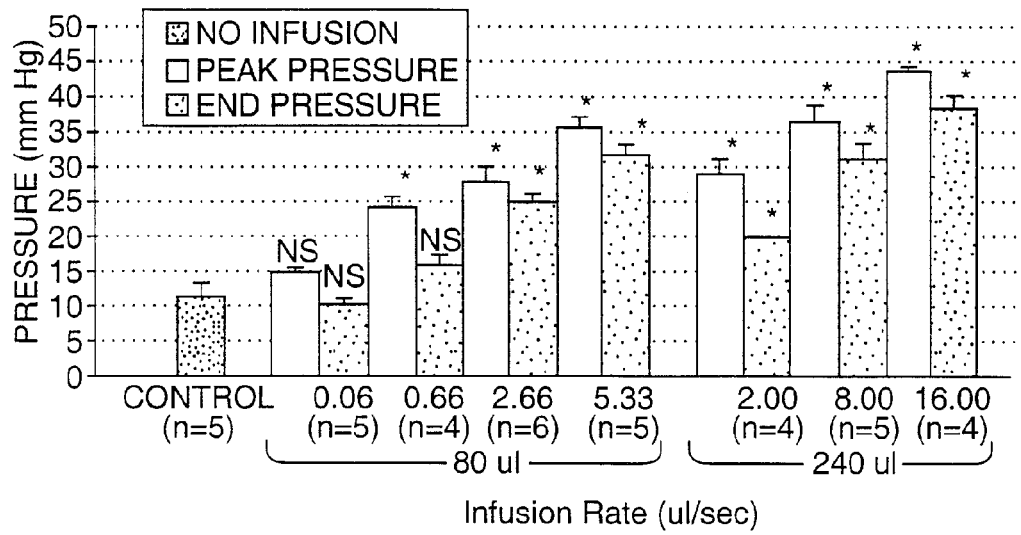
FIG. 8A is a histogram which shows the maximum intrabiliary pressure during retrograde biliary infusion, and the pressure when the infusion was completed, in animals with an occluded common bile duct.

FIG. 8A is a histogram showing the peak pressure and end of infusion pressure at different infusion volumes and rates. Peak (threshold) pressures were significantly different between the no infusion group (n=5) and those animals that received infusions of 80 µl at 0.66 µl/second (n=4), 2.66 µl/second (n=6), and 5.33 µl/second (n=5). Volumes of 240 µl infused at 2 µl/second (n=4), 8 µl/second (n=5), and 16 µl/second (n=4) also resulted in peak pressures significantly different from control ($p<0.05$). The 80 µl, 0.066 µl/second infusion (n=5) resulted in a peak intrabiliary pressure of $14.5\pm0.9$ mm Hg and this was not significantly different from the no infusion group ($11.5\pm1.5$ mm Hg), but was significantly different ($p<0.05$) from the other 80 µl infusion groups. Peak pressures were rate-dependent; at a given infusion volume, each infusion rate evaluated resulted in peak pressures significantly different ($p<0.05$) from those obtained using the other infusion rates. The maximal peak pressure observed was $43.6\pm0.6$ mm Hg (240 µl infused at 16 µl/second).

Figure 8B:
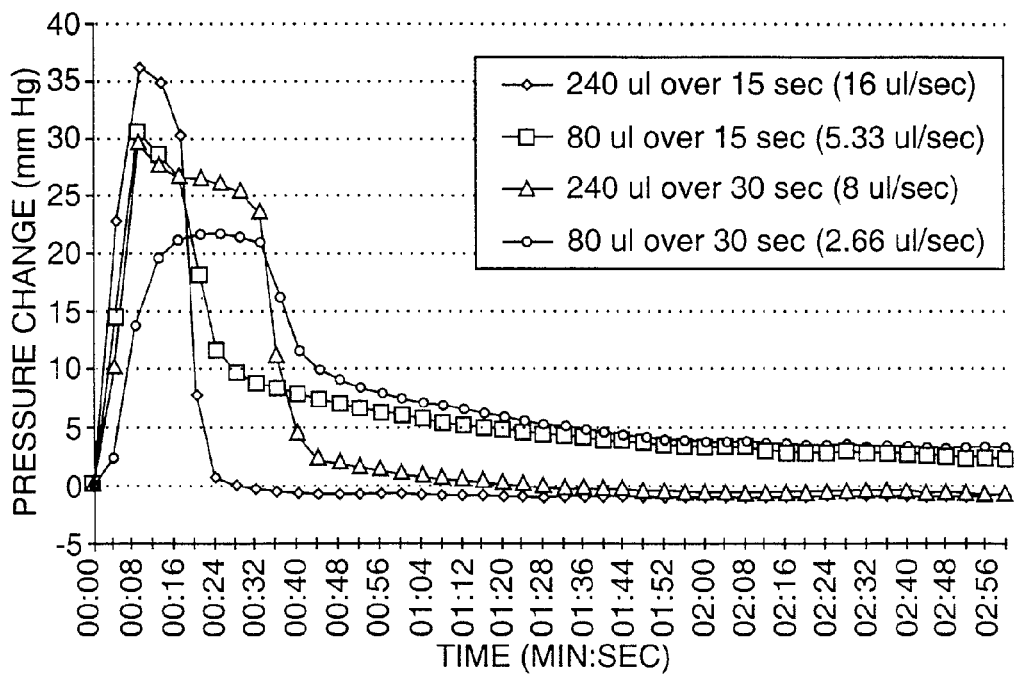
FIG. 8B is a graph of intrabiliary pressure change versus time for a variety of infusion rates, showing that intrabiliary pressure rapidly declines toward the preinfusion pressure following completion of an infusion, illustrating that more rapid larger volume infusions lead to lower recovery pressures.

Pressures at the end of infusion were also dependent upon both the infusion rate and volume. Although infusion at 0.66 µl/second resulted in a significant elevation in peak pressure, by the end of the infusion the pressure was no longer significantly elevated compared to the peak pressure obtained with common bile duct occlusion alone. For all other infusion rates that resulted in significant elevations in peak pressure, end of infusion pressure remained significantly elevated compared to the control pressure. Post-infusion pressures tended to be lower following larger volume, more rapid infusions (FIG. 8B).

Figure 9A:
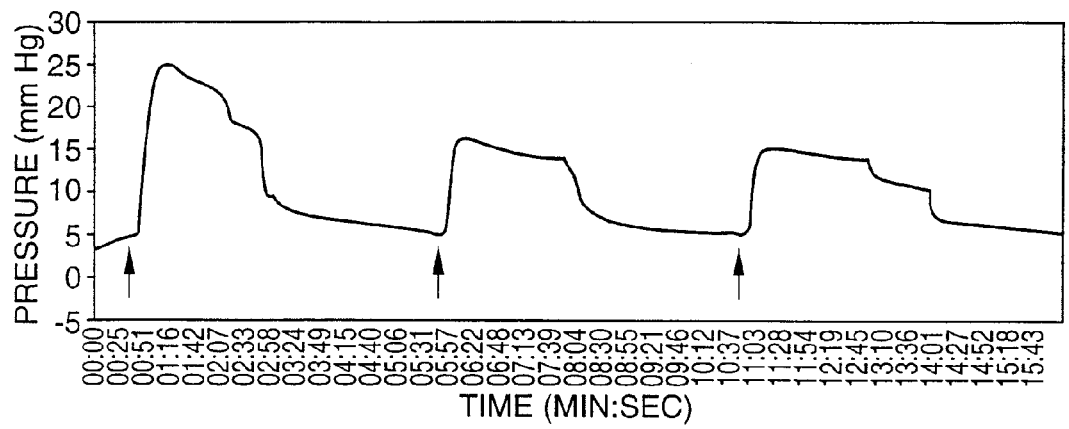
FIG. 9A is a graph of intrabiliary pressure versus time for three sequential infusions of 80 µl over two minutes, illustrating that repeat infusions reach a threshold pressure peak at a lower pressure than the initial infusion.
Figure 9B:
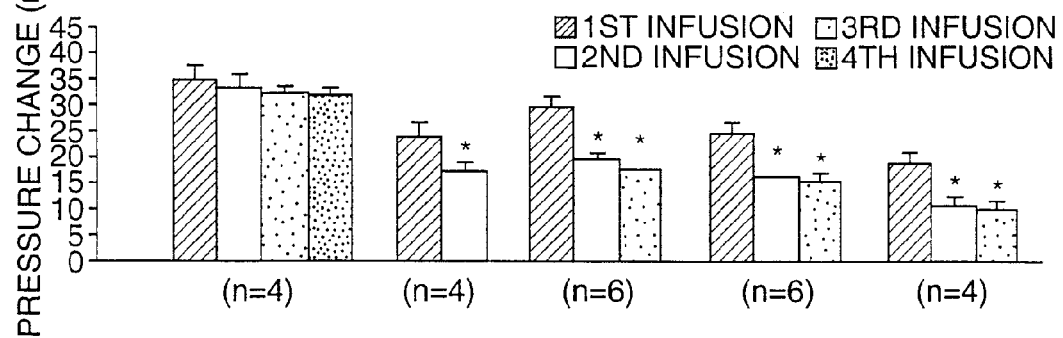
FIG. 9B is a histogram illustrating that threshold peak pressures for repeat infusions after the second infusion do not differ significantly from the peak pressure of the second infusion.

In some studies, a single animal underwent a sequence of up to four repeat infusions at the same infusion volume and rate. Pressure was continuously monitored and each infusion was separated by approximately three minutes from the next infusion. FIG. 9A shows a typical time course of three infusions. FIG. 9B shows that repeat infusions resulted in significantly smaller rises in pressure than were produced by the initial infusion for a particular infusion rate and volume. This finding was statistically significant except at the largest volume and fastest rate evaluated (240 µl infused at 16 µl/second). At any given infusion volume and rate, the pressure changes produced by the second, third, and fourth infusions were not significantly different from each other, even if the second infusion had resulted in a pressure change significantly smaller than that achieved by the first infusion.

In order to evaluate the impact of infusate viscosity and temperature on intralumenal pressure, animals underwent retrograde biliary administration using a range of fluid viscosities at different rates and volumes of infusion. Solutions of different viscosity were prepared by diluting radiopaque contrast dye with 0.9% NaCl in the following dye to saline ratios: undiluted dye, 9:1. 3:1, 1:1, 1:3; and saline without dye. The biliary infusion system was modified in order to deliver approximately 37° C. infusions. The infusion catheter was routed through a length of ⅜" silicone tubing that was continuously perfused with 39 degree C. water. Solutions were preheated to 39° C. and drawn up immediately prior to use. The time required for securing the catheter within the gallbladder lumen resulted in an approximately 2° C. decline in temperature as measured at the catheter tip. Fluid viscosity was determined using an Ostwald Capillary Viscometer at 22 and 37° C.

Figure 10A:
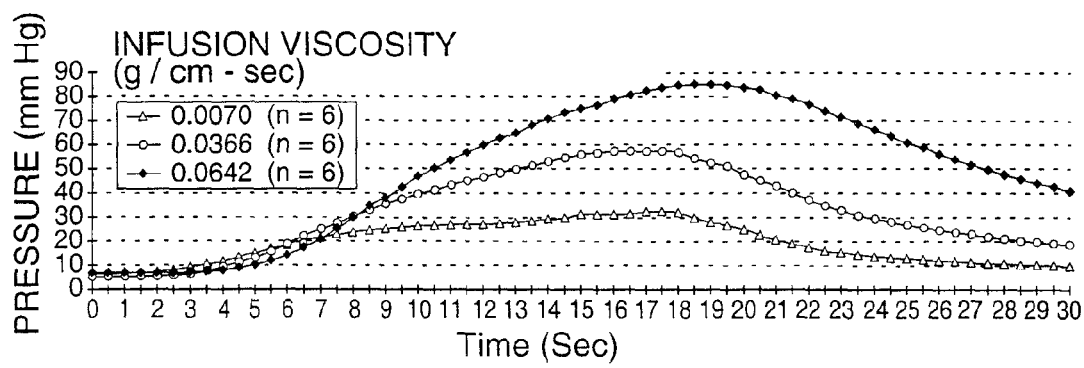
FIG. 10A is a graph of pressure change versus time for infusates of different viscosities (21.90 and 1.05 centipoise)
Figure 10B:
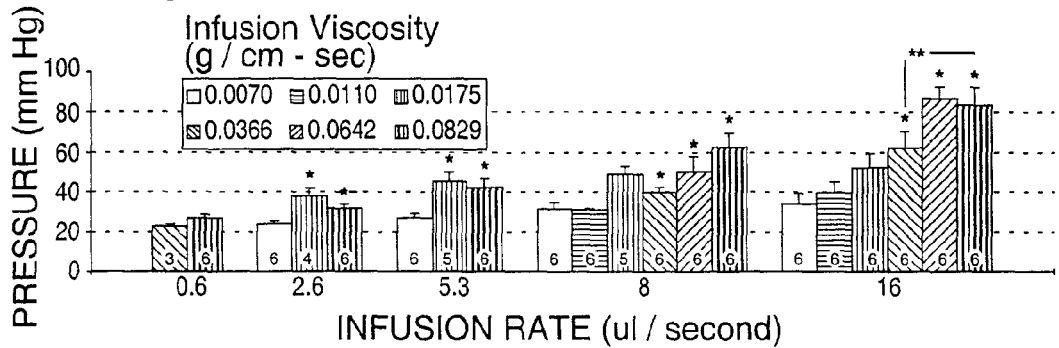
FIG. 10B is a histogram which illustrates the effect of viscosity on peak intrabiliary pressure at different volumes and rates of infusion.
Figure 10C:
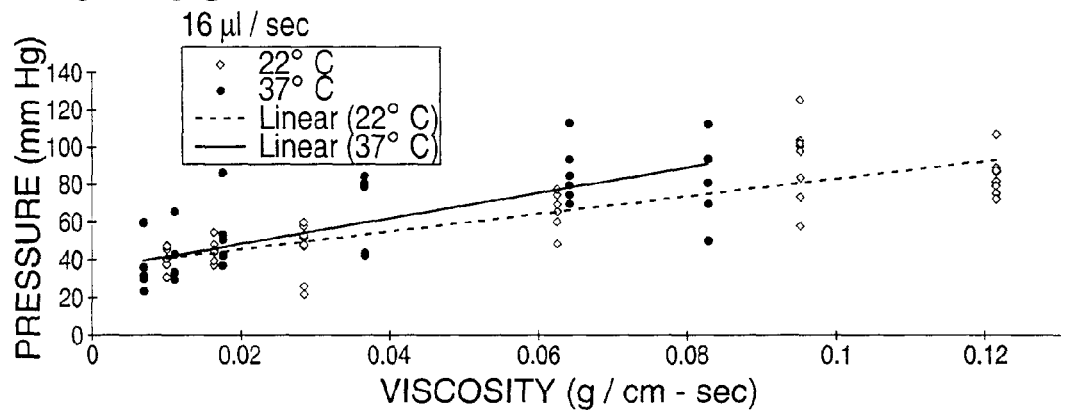
FIG. 10C is a graph of a linear regression analysis of the relationship between viscosity and peak intrabiliary pressure at two infusion temperatures.

As infusion viscosity was increased, intrabiliary pressure was similarly elevated. The graph shown in FIG. 10A presents the temporal pattern of intrabiliary pressure changes at different infusion viscosities. The effect of viscosity on intrabiliary pressure became more apparent at later stages of the infusion. Following 11.5 seconds of infusion (240 µl; 16 µl/second) intrabiliary pressure was significantly greater with the higher viscosity infusion (27.1±2.7 mm Hg at infusion viscosity 0.0070 g/cm-sec versus 56.8 mm Hg±8.8 mm Hg at infusion viscosity 0.0642 g/cm-sec; $p<0.05$). The relationship between fluid viscosity and intralumenal biliary pressure held over a range of infusion rates and volumes but was increasingly evident at larger volumes and faster rates of infusion (FIG. 10B). FIG. 10C is a linear regression analysis of peak intrabiliary pressure as a function of infusion viscosity at two different infusion temperatures. Intrabiliary pressure was dependent upon infusion viscosity at both 22 and 37° C. (correlation coefficients: 22° C., r=0.82; 37° C., r=0.74). Although higher viscosity infusions tended to result in greater increases in pressure at 37° than at 22° C., the linear regression lines shown in FIG. 10C were not significantly different ($p>0.05$). Repeat infusions with solutions of different viscosities (data not shown) followed the same pattern as were seen with saline infusions, i.e., repeat infusions resulted in significantly lower peak pressure changes than were produced by the initial infusion.

EXAMPLE 2

Radiopaque Tracer Studies

A silastic catheter was placed in the gallbladder as described above. Straight (1 mm×3 mm) or curved (1 mm×5 mm) Kleinert-Kutz microvascular clips (MVC; Pilling-Weck, Research Triangle, North Carolina) were then placed rostral to the junction of the superior pancreatic duct with the common bile duct to turn the hepatobiliary system into a closed pressure system. Infusions were administered as in Example 1, and the microvascular clip occlusion caused the infusion to move retrograde into the hepatic duct and then into smaller hepatic ducts and ductules. At the end of the administration period (infusion plus dwell time) the clip was removed and the cholecystotomy catheter was withdrawn.

To evaluate the impact of hepatic venous drainage on the distribution of radioopaque dye and adenovirus following retrograde biliary infusion, the suprahepatic inferior vena cava was temporarily occluded for 5 to 10 minutes with a curved microvascular clip at a level just cephalad to the liver and caudal to the postcaval foramen of the diaphragm. Digital fluoroscopic studies were performed with Renograffin and an OEC Series 9400 X-Ray Imaging System (OEC Diasonics, Salt Lake City).

In some animals Renograffin was rapidly infused retrograde, and digital fluoroscopy was utilized to determine if, and when, dye entered the systemic circulation. Digital images captured at thirty frames per second revealed the rapid appearance of dye in the systemic circulation. Dye appeared to travel up the suprahepatic inferior vena cava before being seen in the heart. Temporary obstruction of the suprahepatic IVC prevented systemic distribution during and after high pressure retrograde biliary infusion. Accordingly, while some degree of lymphatic drainage may possibly have occurred, high pressure retrograde biliary infusion of radioopaque dye appears to have primarily resulted in systemic delivery of infusate via hepatic venous drainage.

Simultaneous measurement of intrabiliary pressure during digital fluoroscopic recording of retrograde biliary infusion revealed that radioopaque dye appeared in the systemic circulation as the intrabiliary pressure was rapidly rising. At an infusion rate of 8 µl/second, pressure began to rise after two seconds or 16 µl of dye had been infused. Dye began to be evident in the lungs after three seconds or 24 µl had been infused. This initial systemic appearance of the tracer therefore indicates that the pressure achieved after two seconds at this infusion rate was a pressure at which subepithelial delivery of the dye has occurred, and represents a pressure level below which this infusate should be administered (at this flow rate) if only epithelial administration is desired.

The intensity of dye in the liver continued to increase even after systemic distribution was first detected. After 5 seconds (40 µl), dye became more pronounced in the inferior vena cava. At six seconds (48 µl), peak pressure was reached and dye was much more evident in both the liver, inferior vena cava, and lungs. This peak pressure therefore represented another threshold at which preferential subepithelial delivery was achieved, that is a pressure that could be used in a situation in which substantially only supepithelial delivery is desired. Digital subtraction fluoroscopy was utilized to compare the hepatic distribution of dye following repeat infusions in the same animal. With each new infusion, the liver parenchyma was filled earlier and at a lower pressure (data not shown). Hence, preferential subepithelial delivery can become enhanced following an initial infusion.

The appearance of substantial dye in the systemic vascular circulation is an indication that the pressure in the hepatobiliary system has exceeded a level at which primarily or substantially exclusively apical epithelial delivery will occur. Hence once tracer appears in the systemic vascular system, subepithelial delivery of the tracer has occurred in the liver. This test can be used to predict infusate pressures or volumes, below the peak pressure, where systemic (instead of local) administration occurs.

EXAMPLE 3

Latex Microsphere as Model for Vector Delivery

In order to both corroborate the digital fluoroscopic studies and histologically evaluate the distribution of infusate, 100 nm and 200 nm diameter fluorescent latex microspheres were administered by retrograde biliary infusion. Spheres of this diameter were selected since they are close in diameter to adenoviral (80 nm) and liposomal (200-500 nm) vectors. Yellow green (490 nm peak excitation wavelength) carboxylate-modified fluorescent latex mircrospheres (Molecular Probes, Eugene, Oreg.) were diluted in 1× PBS and extensively sonicated prior to use. Sphere concentration was maintained constant at $1 \times 10^{11}$ spheres per animal, while the volume and rate of infusion were varied between animals. Following the completion of infusion, fresh frozen sections were prepared from the liver and lung and evaluated under fluorescent microscopy. To visualize histologic detail more completely, some slides were stained with Evans Blue (0.05% for 20 seconds), which appears red at a 580 nm excitation wavelength. Since tight junction pore diameter is less than 18 D in diameter, these latex spheres cannot pass outside of the biliary tree in the absence of either (a) physical disruption of the integrity of the tight junction barrier or (b) transcytosis across hepatocytes and/or biliary epithelial cells.

With retrograde biliary infusion of 100 nm spheres at a low infusion rate ($1 \times 10^{11}$ spheres in 80 µl infusion volume, infused at a rate of 0.66 µl/second), spheres were found throughout acinar zones 1 through 3. Spheres were located in periportal bile ducts and canaliculi, as well as in canaliculi and hepatic sinusoids adjacent to central veins. These findings indicate that, at this low infusion rate and low pressure, primarily localized epithelial and peri-ductular delivery was occurring, without substantial systemic administration.

A comparison of the distribution detected following retrograde biliary infusion of different infusion volumes (infusion volumes of 20, 80, and 240 µl; infusion time 30 seconds for each). At the largest volume infused, very few spheres were found in the liver and those detected were found adjacent to and in central venules. Both 100 nm and 200 nm spheres were found in the pulmonary parenchyma following high pressure retrograde biliary infusion. These findings are consistent with the digital fluoroscopic studies and indicate that high pressure retrograde biliary infusion leads to hepatic sinusoidal and subsequent systemic distribution of 100-200 nm diameter latex microspheres.

Distribution of microspheres is therefore another test that can be used to select a pressure or volume, at a selected infusate rate and viscosity, at which either primarily epithelial or sub-epithelial delivery will occur, in a particular species, organ, or individual. The results of such tests (or computer or other modeling thereof) can then be used to select infusate parameters in subsequent subjects.

EXAMPLE 4

Adenoviral Vector Preparation and Transfer Evaluation

AvlLacZ4 is a replication-deficient, Ela-deleted, recombinant adenovirus (Human, Type 5) that expresses a recombinant nuclear targeted $E.\ coli$ β-galactosidase gene under the control of a Rous Sarcoma Virus (RSV) promoter. Virus was prepared and titered as previously described in Mittereder et al., $J.\ Virol.$ 70:7498-7509, 1996, which is incorporated by reference. Freshly removed tissues were fixed in 10% neutral buffered formalin for at least six hours and then embedded in paraffin and titered as previously described in Mittereder et al. Immunohistochemical detection of β-galactosidase protein was performed using a modified Avidin-Biotin Complex technique. Primary antibody was Rabbit IgG anti-β-galactosidase antibody or negative control rabbit IgG antibody (Cortex Biochem). Secondary antibody was Goat IgG anti-Rabbit IgG antibody. Detection was with Avidin-Biotin Complex and DAB Chromagen. Slides were counterstained with hematoxylin (Biomeda).

Levels of gene transfer one week following intravenous and retrograde biliary infusion were evaluated by determining the percentage of immunohistochemically positive hepatocyte and cholangiocyte nuclei as observed in six random 200× fields. Levels of gene transfer three days following intravenous and retrograde biliary infusion were evaluated by counting the percentage of immunohistochemically positive nuclei as observed in four random 400× fields. Transmission electron microscopy was performed on serum obtained by cardiac puncture fifteen minutes following high pressure retrograde biliary infusion. Particles with a diameter of 80 nm and a morphology characteristic of adenovirus were present in low concentration (data not shown).

Temporarily obstructing hepatic venous drainage resulted in retention within the liver of radioopaque dye delivered by high pressure retrograde infusion. Similarly, interference with hepatic venous return augmented gene transfer. Animals were administered $6 \times 10^8$ biological plaque-forming units of β-gal adenovirus intravenously, by very high pressure retrograde biliary infusion (240 µl, 2 µl/second), with or without temporary hepatic venous obstruction for 5 minutes or 10 minutes. Livers were removed one week following vector administration and evaluated by immunohistochemistry for evidence of gene transfer. One week following intravenous administration no gene transfer was detected in the liver. This is consistent with the low adenoviral dosage used and the late time point utilized for evaluating for evidence of gene transfer. However, positive hepatocytes and cholangiocytes were detected one week following high pressure retrograde biliary infusion of an identical dosage of adenovirus, showing the relative effectiveness of focal delivery compared with systemic administration.

Figure 11:
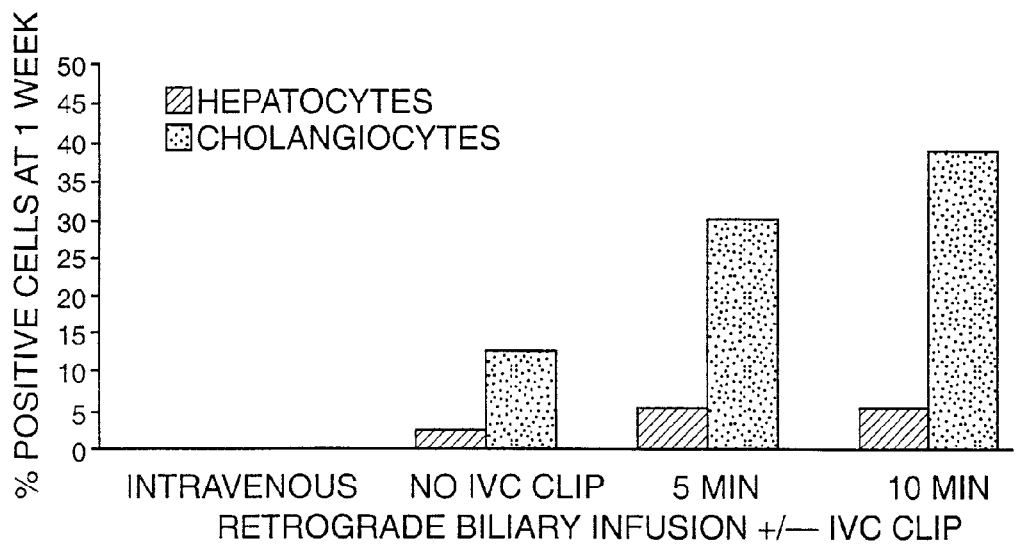
FIG. 11 is a histogram showing preferential delivery of β-gal adenovirus to cholangiocytes instead of hepatocytes both before and after clipping the inferior vena cava.

The percentage of hepatocytes and cholangiocytes with positive nuclei was increased by temporary occlusion of the suprahepatic inferior vena cava (FIG. 11), hence temporary occlusion of venous outflow from the liver can be used to improve organ specific delivery of gene transfer (for example at least doubling or tripling preferential delivery to cholangiocytes as compared to hepatocytes as shown in FIG. 11). Selective cholangiocyte delivery could be enhanced by increasing the duration of the temporary occlusion of the venous return from the liver. The greatest increase in gene transfer occurred in biliary epithelial cells near portal triads. Positive hepatocytes were also found in a primarily periportal distribution following inferior vena cava occlusion combined with retrograde biliary infusion. In some animals the suprahepatic inferior vena cava was removed one week after high pressure retrograde infusion of β-gal adenovirus and evaluated by immunohistochemistry. Gene transfer was detected in endothelial cells from suprahepatic vena cavas removed from animals that underwent high pressure retrograde biliary infusion combined with suprahepatic inferior vena cava occlusion. This indicates that high pressure retrograde infusion led to circulation of adenovirus into the vena cava.

Figure 12:
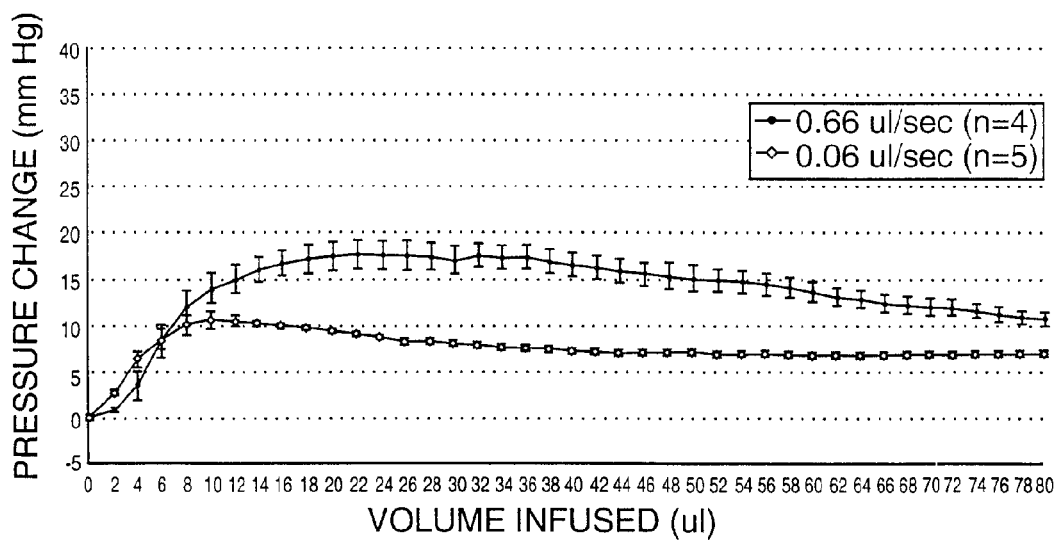
FIG. 12 is a graph of intrabiliary pressure change over time during infusion of 80 µl of infusate at 0.06 µl/sec and at 0.66 µl/sec.

To determine whether gene transfer occurred at lower delivery pressures, animals were administered β-gal adenovirus by retrograde biliary infusion using two different infusion parameters (80 µl; 0.66 µl/second (n=4) versus 0.066 µl/second (n=5)). As previously shown in FIG. 8B, infusion of 0.9% NaCl under these same conditions produced distinctly different intrabiliary pressure curves and peak pressures. Infusion at 0.66 µl/second resulted in a significant rise in intrabiliary pressure ($p<0.05$), while infusion at 0.06 µl/second only led to a non-significant change in pressure. FIG. 12 shows a more detailed comparison of pressure change as a function of volume infused for 80 µl infused at 0.066 µl/second and 0.66 µl/second. The pressure-volume curves differ early and remain distinct throughout much of the infusion.

Figure 13:
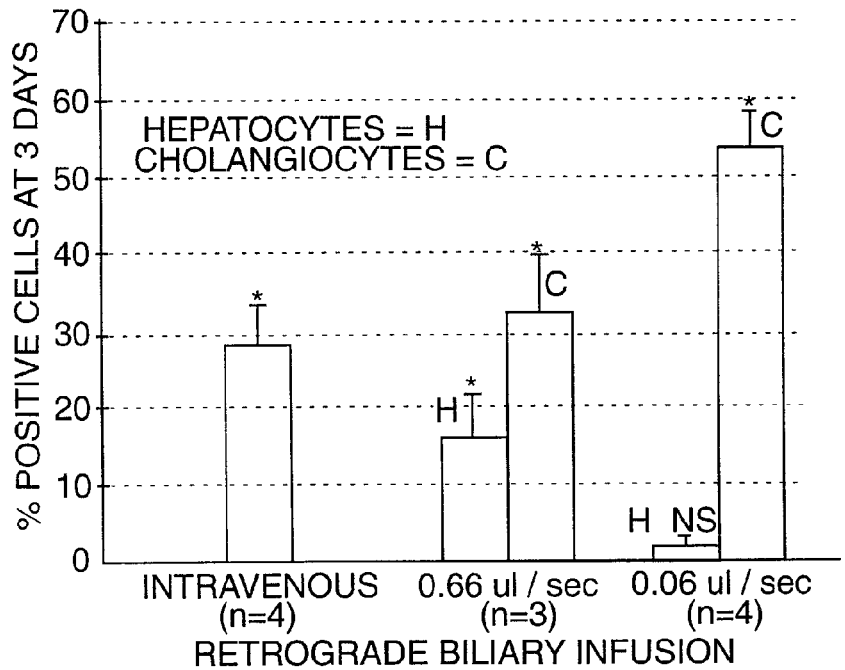
FIG. 13 is a histogram showing the percentage of cholangiocyte and hepatocyte nuclei positive for gene transfer, comparing intravenous (iv) administration to intrabiliary infusion at 0.06 µl/sec and 0.66 µl/sec flow rates, demonstrating that the lower flow rate resulted in preferential delivery to cholangiocytes.

For animals that received β-gal adenovirus by retrograde biliary infusion, the total amount of time of common bile duct occlusion was maintained constant at 25 minutes for contact time with cholangiocytes. For comparison, an additional group of animals received intravenous β-gal adenovirus. Tissues were removed three days following virus administration and evaluated for evidence of gene transfer by beta-galactosidase immunohistochemistry. The three experimental groups had distinctly different histological patterns of gene transfer. FIG. 13 is a histogram summarizing the patterns of gene transfer observed by β-galactosidase immunohistochemistry three days following administration of $3\times10^9$ bpfu of β-gal adenovirus.

Intravenous administration (n=4) resulted in a completely sinusoidal pattern of gene transfer: 28.2±5.0 percent hepatocytes were positive for gene transfer, while no cholangiocytes were positive. This level of gene transfer was significant ($p<0.05$) when compared to vehicle infusion (n=6). The higher pressure retrograde biliary infusion group (80 µl, 0.66 µl/second, n=3) had a mixed pattern of both cholangiocyte (32.2±7.3 percent positive, $p<0.05$) and hepatocyte gene transfer (16.1±1.0 percent positive, $p<0.05$). The lowest infusion pressure group (80 µl, 0.066 µl/second, n=4) had gene transfer almost exclusively in cholangiocytes (53.4±4.5 percent positive, $p<0.05$), with only a very low, non-significant percentage of hepatocytes positive for gene transfer (1.9±1.0 percent positive, $p>0.05$). These results show that cholangiocyte-selective gene transfer occurred by reducing the intrabiliary pressure and thereby decreasing the leakage of infusate during retrograde biliary administration. Decreased leakage may also have increased cholangiocyte gene transfer by lengthening the amount of time the virus was in contact with this cell type.

These findings indicate that retrograde biliary infusion beyond a critical filling volume/pressure results in redistribution of infusate through the hepatic sinusoids with subsequent hepatic venous drainage, and systemic vascular distribution of the infusate. The very low infusion rates (and pressures) much more efficiently delivered the genes to the epithelial cells, to the substantial exclusion of subepithelial delivery. As shown in FIG. 13, delivery at the higher rate/pressure (0.66 µl/second) resulted in preferential delivery to the cholangiocytes, but only by a ratio of about 2:1 of cholangiocytes to hepatocytes. However, delivery at the lower rate/pressure (0.06 µl/second) yielded preferential delivery to cholangiocytes, by a ratio of about 10:1 or more of cholangiocytes to hepatocytes.

Intrabiliary pressure changes were dependent upon the infusion volume, rate, and viscosity, and the pressure curves for any substance can be prepared in accordance with the examples in this specification. Digital fluoroscopic evaluation provides detailed information about the pressure at which the biliary tree is filled to the point of systemic leakage. Delivery of infusate under conditions that result in relatively low intrabiliary pressures leads to a primarily periductular and canalicular distribution of agents, such as the 100 and 200 nm latex microspheres or adenoviral vectors. In contrast, retrograde biliary infusion under conditions that result in significant elevations in intrabiliary pressure lead to a sinusoidal distribution of infused microspheres and a mixed pattern of cholangiocyte and hepatocyte gene transfer.

Figure 14:
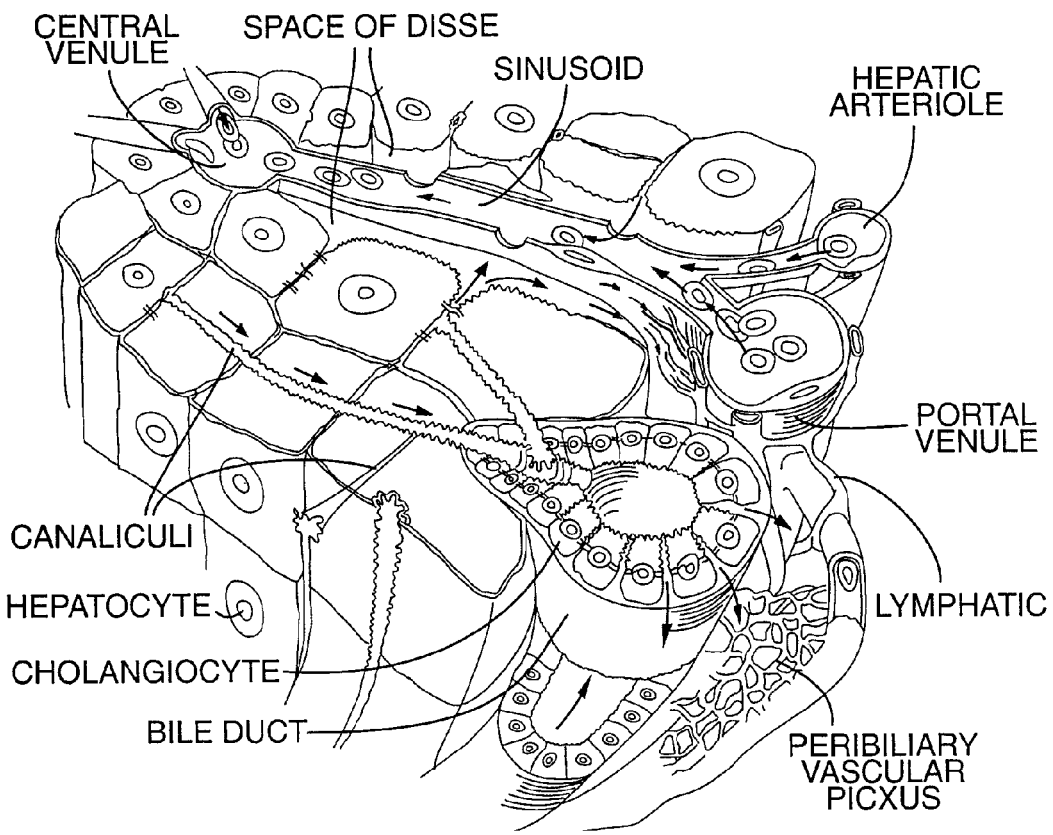
FIG. 14 is a schematic diagram illustrating some of the potential histological pathways that may be taken by high pressure retrograde biliary infusion.

The histological patterns of microsphere distribution and gene transfer observed at different infusion volumes and rates indicate that tight junctions involved in the acute release of excess intralumenal volume/pressure were located between adjacent cholangiocytes at the level of either small bile ducts and/or the tight junctions between adjacent hepatocytes at the level of the biliary canaliculi. FIG. 14 schematically shows the potential pathways that may be taken by a high pressure retrograde biliary infusion. Disruption of tight junctions at the level of bile ducts lacking a lamina propria (i.e., smaller ducts) would result in the leakage of retrograde biliary infusate into subepithelial spaces, where it would be drained by vascular capillaries, ultimately resulting in a sinusoidal redistribution of the infusate. Disruption of tight junctions at the level of the biliary canaliculi would result in leakage into the Space of Disse. Infusate would then either be drained into lymphatic capillaries contiguous with this space but located beyond the limiting plate, or would travel through fenestrae into the vascular (sinusoidal) space. Passage of molecules greater than 100 nm in diameter into the sinusoidal space would require disruption of fenestrae. The 200 nm microspheres had a similar sinusoidal pattern of distribution following retrograde biliary infusion as that obtained with 100 nm microspheres. Accordingly, high pressure retrograde biliary infusion may also disrupt fenestrae in a manner analogous to what has been previously shown to occur following high pressure vascular perfusion.

By measuring the intrabiliary volume/pressure capacitance (change in pressure with change in volume) and determining the volume/pressure thresholds for disruption of tight junctions, it is possible to utilize intrabiliary administration parameters that maximize local delivery and result in only minimal (or substantially no) systemic distribution of infusate (for example a local to systemic delivery of at least 2:1, 3:1, 5:1, 10:1 or even more). This specific delivery can be accomplished using a variety of approaches. Since repeat infusions fail to achieve the same peak pressure as the initial infusion, an initial infusion specifically designed to measure the pressure threshold for tight junction disruption could be followed by a second infusion that would be utilized to measure at what volume/pressure infusate leaked across disrupted junctions (using radiographic tracer studies and histologic examination of tissues as described above). The therapeutic agent would then be delivered using a volume/pressure below this leakage threshold. Each infusion should have the same fluid viscosity, and the therapeutic molecule ideally will have only minimal diffusion through opened tight junctions. Alternatively, capacitance and disruption/leakage thresholds could be determined and the therapeutic agent administered at sub-disruption pressures once tight junction repair had occurred (for example after a few hours have passed to allow the tight junctions to be re-established).

Catheters or other devices make it possible to remove residual, non-absorbed infusate following a defined period of contact with targeted cells. Low pressure focal delivery, in combination with removal of non-absorbed material, would thus permit the use of more therapeutically useful dosages of otherwise toxic materials because removal of the infusate minimizes the potential for dose-limiting systemic toxicity. Repetitive administration can also occur either through endoscopic and laparoscopic approaches, or alternatively by administration from novel, implantable devices that would permit episodic retrograde biliary infusion on controlled (and potentially outpatient) schedules.

Prior determination of intrabiliary capacitance and the critical pressure threshold for disruption of tight junctions can be used to allow selective delivery of experimental and therapeutic agents to the hepatic sinusoidal space. Retrograde biliary infusion of therapeutic agents can be made at controlled pressures specifically designed to disrupt biliary ductular and/or canalicular tight junctions and cause leakage. This method of sinusoidal perfusion would be an alternative to portal venous and hepatic arterial catheterization. Convection-based (i.e., pressure gradient) methods of drug delivery have been previously reported to increase the effective delivery of relatively non-diffusable agents following direction injection into the brain parenchyma. Similarly, convection-based delivery to the hepatic parenchyma through a non-vascular (e.g., retrograde biliary infusion) route of administration provides a method for maximizing delivery to poorly vascularized areas of diseased tissue within the hepatic parenchyma.

Polarized epithelia separated by tight junctions are found lining ductular structures in many organs. Diseases of these cells are important causes of human morbidity and mortality. Accordingly, administration of therapeutic agents through ductular structures using pressure-controlled intralumenal delivery are relevant for both hepatobiliary and non-hepatobiliary tissue targets and diseases. Examples of diseases that can be treated by ductular administration of therapeutic agents include diseases of the biliary epithelia (cystic fibrosis, autoimmune cholangiopathies, and opportunistic infectious diseases associated with AIDS); diseases such as cirrhosis which are associated with hepatic fibrosis; diseases of the salivary or parotid gland; and a variety of malignancies, for example pancreatic adenocarcinomas which are poorly vascularized and do not respond well to traditional methods of treatment. The present method can also be adapted for the delivery of agents to other hollow organs, such as the selective delivery of anti-inflammatory agents to the bowel wall in diseases of the intestine (such as Crohn's disease in which local administration of corticosteroids or other anti-inflammatory drugs may be desired). Selective delivery in the bowel (or any other hollow organ) can be achieved by isolating a segment of the hollow organ (for example between first and second inflatable balloons) to convert that portion of the hollow organ into a pressurizable segment into which the infusate can be introduced at a selected pressure/volume/flow rate.

EXAMPLE 5

Delivery Devices

Figure 15:
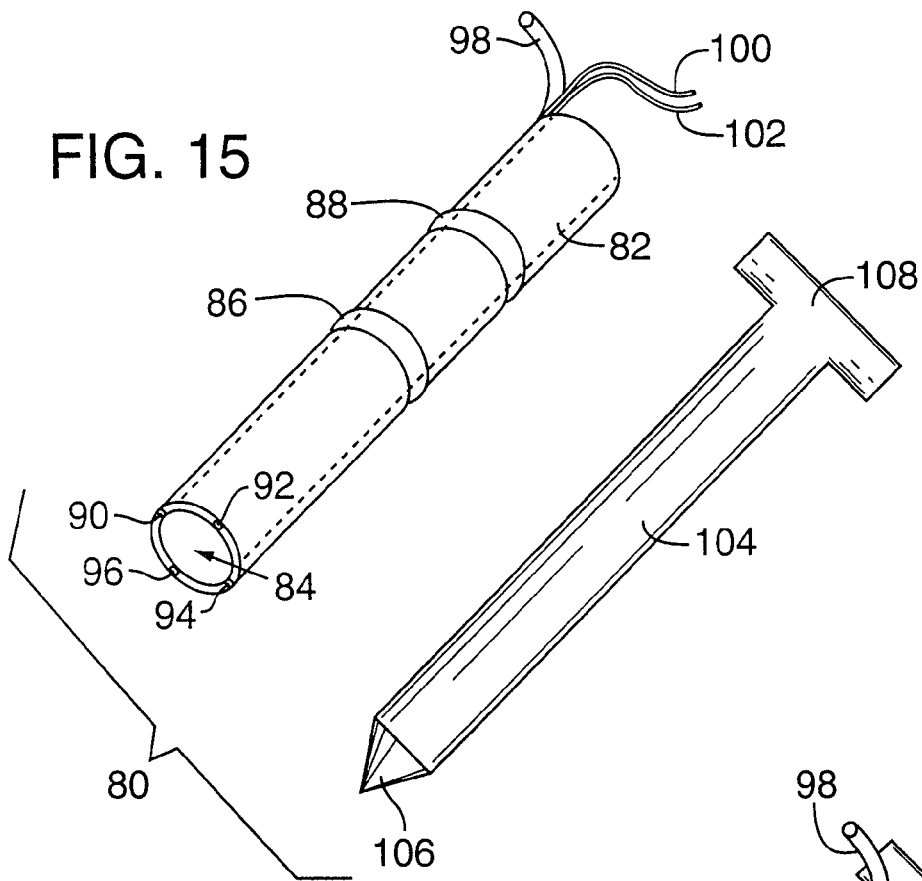
FIG. 15 is a somewhat schematic, perspective view of a biliary tree access cannula (with its trochar removed) that can be used for site specific delivery of agents into the gallbladder.

The present invention also includes a variety of delivery devices for administering substances under carefully controlled pressure conditions that allow cell and anatomic site specific delivery. An embodiment of one such device is shown in FIG. 15, which illustrates a biliary tree access cannula 80 that includes an elongated tubular body 82 that defines a central lumen 84. First and second inflatable balloons 86, 88 circumscribe body 82, and are spaced a sufficient distance from one another to allow the balloons to rest against the internal and external walls of the gallbladder when the balloons are inflated. When the balloons 86, 88 are deflated, they conform closely to the external surface of catheter and do not obstruct introduction of the catheter through surgical openings.

Small orifices 90, 92, 94, 96 are provided in the flat distal annular face of cannula 80, and each of these orifices communicates with a respective passageway in the wall of the cannula 80 that in turn communicates with a drainage line 98 at a more proximal portion of the cannula 80.

Inflation ports 100 and 102 are also provided at the proximal end of the cannula, which respectively communicate with balloons 86, 88 for inflating and deflating those balloons. A rigid trochar 104 with a sharp cutting tip 106 and a blunt handle end 108 is of sufficient dimensions to slide within lumen 84 of cannula 80.

Figure 16:
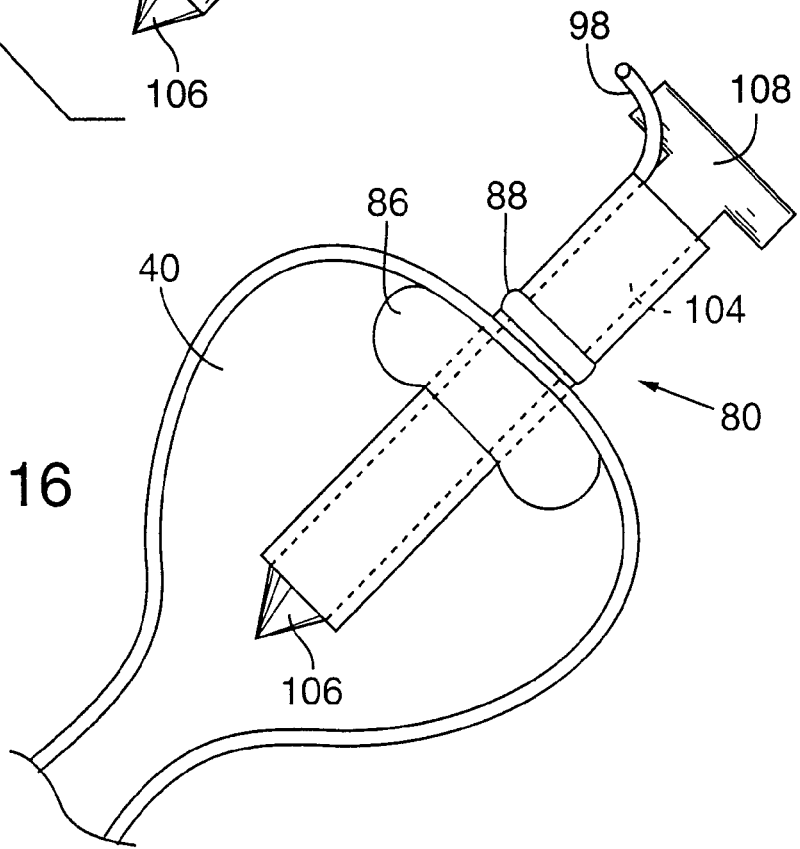
FIG. 16 is a view of the cannula of FIG. 15, but showing it assembled and inserted through the wall of the gallbladder, with a balloon inflated against the internal wall of the gallbladder.
Figure 17A:
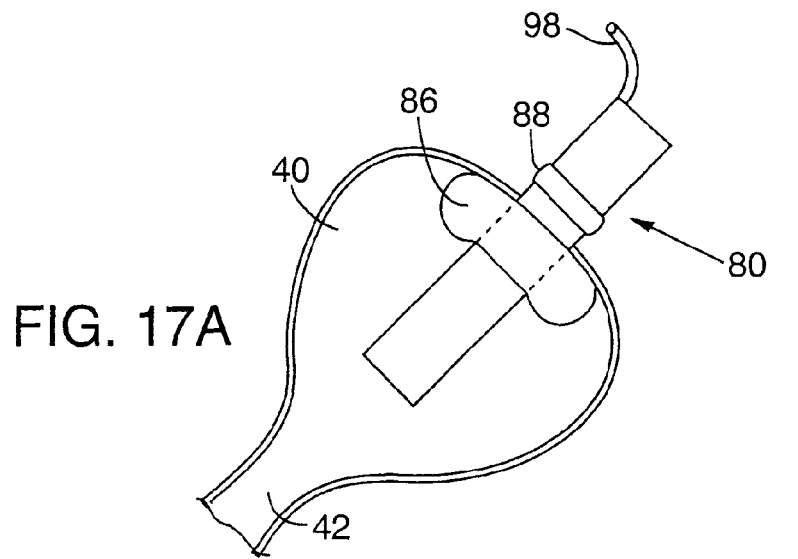
FIG. 17A is a view similar to FIG. 16, but showing the cannula with the trochar removed and the cannula elevated against the wall of the gallbladder.
Figure 17B:
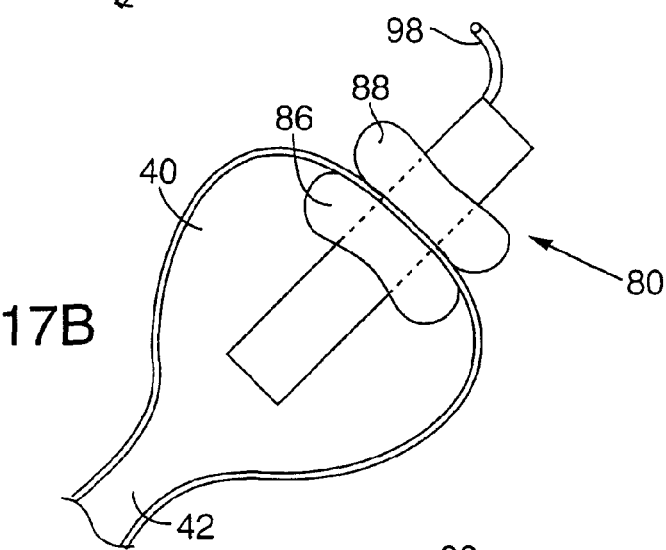
FIG. 17B shows an external balloon inflated to help seal the opening through which the trochar is introduced.
Figure 17C:
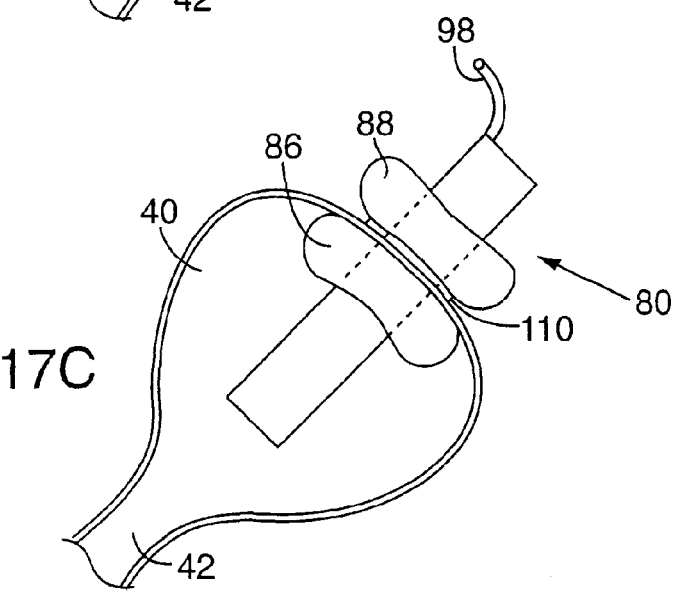
FIG. 17C is yet another embodiment, in which a silicon washer is also placed around the trochar between the balloons to help seal the opening, and maintain the biliary system as a closed pressure system.
Figure 18:
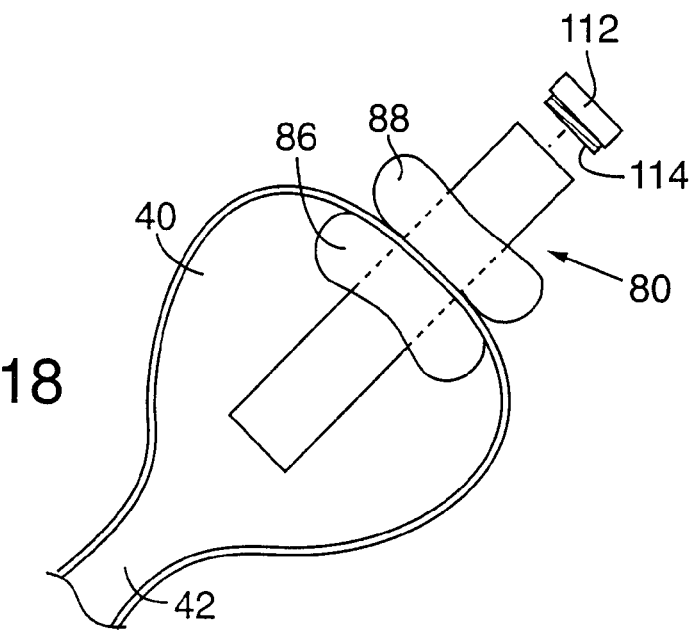
FIG. 18 is a view similar to FIG. 17B, but showing a cap for selectively closing the cannula.

To use the delivery device, trochar 104 is inserted in the lumen 84 of cannula 80, as shown in FIG. 16. After gaining surgical access to the abdominal cavity (for example through a laparoscopic or midline incision), the sharp tip 106 of trochar 104 is used to introduce cannula 80 through the wall of the gallbladder 40. After penetration, cannula 80 is then advanced until first balloon 86 (in its deflated condition) has entered the interior of the gallbladder 40, but advancement is stopped before the second balloon 88 (in its deflated condition) enters the gallbladder. The first balloon 86 is then inflated by introducing pressurized fluid (such as air) through port 100, so that balloon 86 expands and conforms to the internal surface of the gallbladder 40 and stabilizes the cannula in its desired position. Bile is then removed from the gallbladder through drain line 98, which withdraws the bile through orifices 90-96 which open on the distal face of cannula 80. Trochar 104 is then removed from cannula 80 (FIG. 17A), and the second balloon 88 is inflated on the external surface of gallbladder 40, so that the two balloons 86, 88 help maintain the cannula in its desired position shown in FIG. 17. Alternatively, as shown in FIG. 17C, a silicon washer 110 can be inserted over the proximal end of cannula 80 and positioned on the outer surface of gallbladder 40, around the opening in the gallbladder through which the cannula extends, to further provide a relatively atraumatic pressure seal. After the cannula 80 is positioned and the balloons inflated, a cap can be placed on the proximal end of the cannula to selectively permit access to the indwelling cannula. The illustrated cap 112 is a screw cap, with helical threads 114 that mate with internal threads (not shown) at the proximal lumen of the cannula. Cap 112 is selectively removable (for example by unscrewing it), and/or may be penetratable (for example by a needle).

Figure 19:
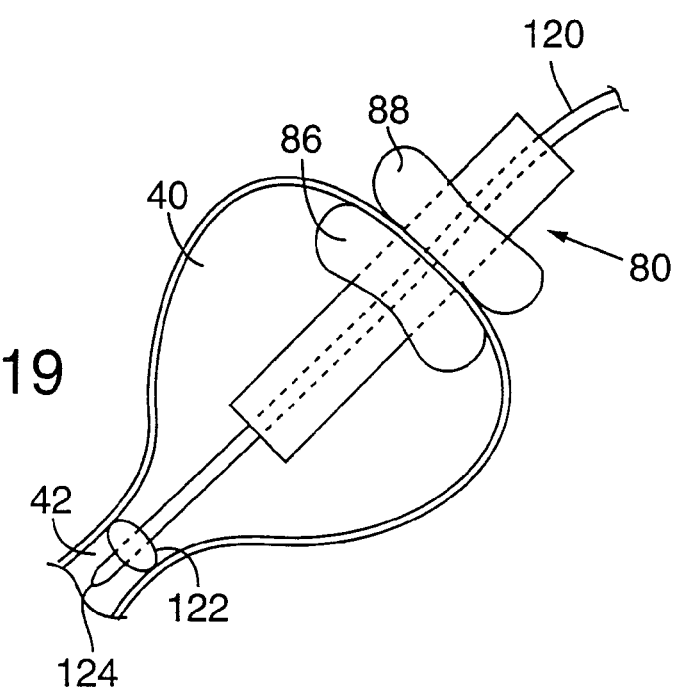
FIG. 19 is a view similar to FIG. 18, but showing the distal tip of a cathether introduced through the trochar to position an occlusive balloon in the cystic duct, for pressure isolation of the gallbladder.

When access to the gallbladder is desired, cap 112 is removed and an elongated, flexible multiple lumen catheter 120 is introduced through cannula 80. Catheter 120 has an inflatable balloon 122 (FIG. 19) adjacent its distal tip 124, and the catheter is advanced through cannula 80 until the distal tip is positioned in the cystic duct, in a position that the inflatable balloon can occlude cystic duct 42, to create a substantially sealed chamber within the gallbladder, as shown in FIG. 19.

An embodiment of the structure of the catheter 120 is shown in the enlarged view of FIG. 20A, including four central lumen quadrants 126, 127, 128, 129 and two outer concentric lumens 136, 137. The outermost concentric lumen 136 communicates with the exterior of the catheter 120 through apertures 130. The other lumens of the catheter 120 communicate with the exterior of the catheter via apertures 131-135.

The various lumens may be used for different purposes. For example, one or two of the lumens can be used for sensing pressure within the gall bladder and/or within the hepatobiliary system; another of the lumens can be used for introducing, and another for withdrawing, a therapeutic infusion. Another lumen can be used for introducing, and another for withdrawing, rinsing fluid.

As an alternative catheter design, the multiple lumens can all be of concentric configuration (FIG. 21). As an alternative aperture arrangement, shown in FIG. 22, a catheter such as that having the tip of FIG. 20B or 21 can be provided with a series of apertures arranged in separate annular bands. A first band 140 communicates with a first and central lumen that can be used for introducing rinsing fluid through the catheter into the gall bladder. A second band 144 communicates with a second lumen, concentric with the first, that can be used for removing rinsing fluid through the catheter. A third band 148 communicates with a third concentric lumen and can be used for introducing drug/vector into the catheter at the preselected flow rate/pressure, and a fourth band 152 communicates with a fourth concentric lumen for withdrawing vector from the gallbladder after it has dwelled in contact with the appropriate cells for the desired period of time at a preselected pressure.

In catheters for use in the present invention, lumens may communicate with the catheter exterior either proximally or distally of the balloon 122, depending on the location of the space to be accessed. Dual and even single-lumen catheters may also be employed, with a single lumen serving multiple functions, but a catheter with a built-in pressure transducer at or near the tip, or a catheter with at least two lumens is generally preferred, so that pressure monitoring and infusion may easily and simultaneously be performed. Even a single lumen catheter having no built-in transducer may potentially be employed, however, if a sensitive pressure transducer is included in the infusion circuit, and if the fluid flow characteristics of the infusion circuit are such that the infusion pressure at the source of infusate accurately reflects the pressure inside the gall bladder or other hollow organ space.

Of course many other general catheter designs other than the examples given are known to those of skill in the art and may find useful application within the context of the present invention. The lumen configurations above are thus provided by way of example only, and not by way of limitation.

Figure 23:
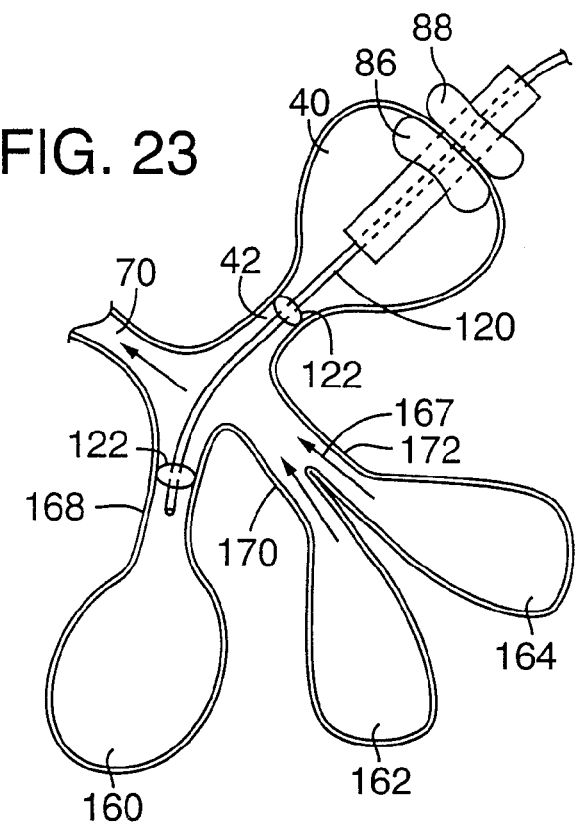
FIG. 23 is an alternative embodiment of the catheter, in which a distal multi-lumen tip has been moved into a biliary duct to occlude a lobular duct (and effectively pressure seal the ductular system of a liver lobe).

FIG. 23 illustrates the versatility of the delivery device, in that it can be used not only for intralumenal delivery of infusate to the gallbladder, but can also be used in other organs as well. As is well known, bile from liver lobes (such as lobes 160, 162 and 164) moves in a normograde direction 167 through biliary ducts 168, 170 and 172 from the liver toward the common bile duct 70. FIG. 23 shows that catheter 120 can be advanced through the cystic duct 42, in a retrograde direction up the hepatic duct, until the tip is positioned in a biliary duct that drains bile from a discrete lobe of the liver (such as lobe 160). When the tip is in this position, first balloon is in a position that it can be inflated to effectively isolate the liver lobe 160, and turn it into a pressurizable hollow organ space. Also, a second balloon 170 on the catheter is positioned in the cystic duct, where it can prevent movement of bile into the gallbladder.

Figure 24:
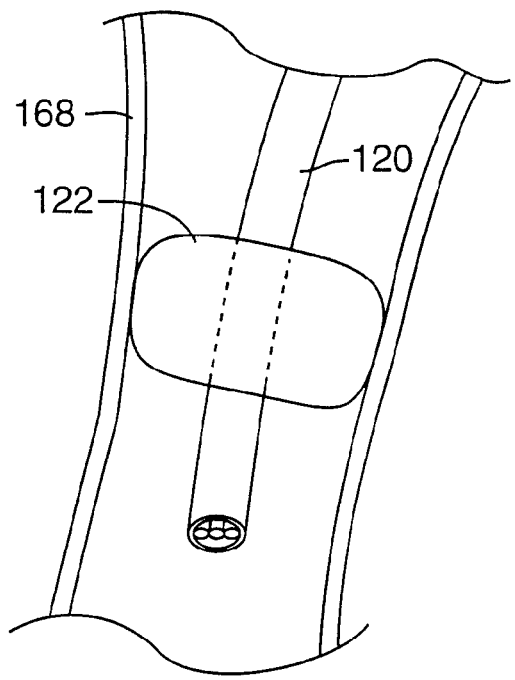
FIG. 24 is an enlarged view of the tip of the catheter of FIG. 23, showing the multiple lumens for performing different tasks, such as infusion of pressure media, delivery of vectors, and sensing pressure at the catheter tip.

Once the catheter is positioned as shown in FIG. 23, infusate can be introduced under pressure through the catheter into the bile ductular system of liver lobe 160. The pressure can be controlled by a controller (not shown) to a preselected pressure (or volume) that has been found to provide site specific delivery of the infusate to a desired site (such as the apical epithelial cells, periductular tissue, or the subepitheial/sinusoidal space). In an instance in which specific delivery is desired to the epithelial cells, a pressure transducer in the distal tip of catheter 120 provides continuous or frequent pressure measurements to the pressure controller, to maintain the pressure in the ductular system at or about the preselected level that achieves site specific delivery. Alternatively, pressure may be measured via an external transducer in fluid communication with the delivery site via one of the catheter lumens. For delivery into the liver, at least one, if not all of the lumens of the catheter, should communicate with the exterior of the catheter at a position distal of the balloon 122 (FIG. 24).

EXAMPLE 6

Vector Transfer to the Gallbladder Lamina Propria

Figure 25:
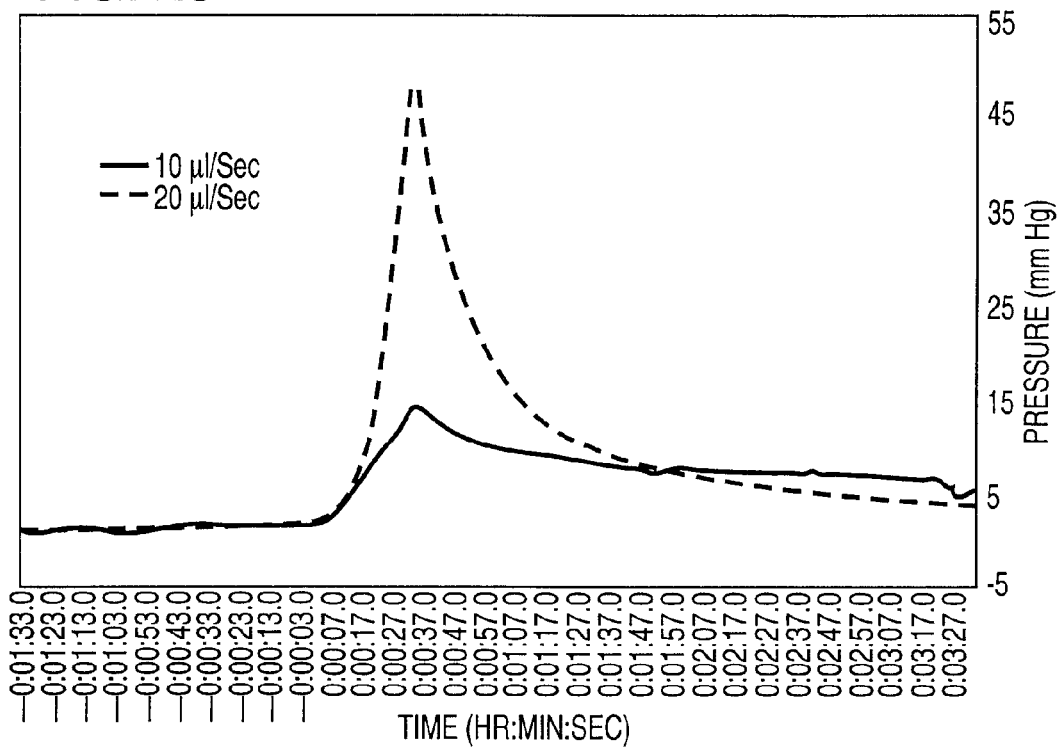
FIG. 25 is a graph of pressure versus time in the gallbladder at infusion flow rates of 10 µl/30 seconds (solid line) and 20 µl/30 seconds (dotted line).

A double-lumen catheter was surgically secured within the gallbladder of 20 gm mice while the cystic duct was occluded with a clip. Infusions were administered using a digital microinfusion pump via one of the lumens while changes in gallbladder pressure were measured by a pressure transducer via the other lumen. This system was found to be quite sensitive to changes in infusion volume or rate. For example, 10 µl of 0.9% NaCl infused over 30 seconds resulted in a 3 mm Hg rise in pressure, while 20 µl infused over 30 seconds resulted in a 45 mm rise in pressure (FIG. 25). Tissue electron microscopy (TEM) was used to evaluate the ultrastructural effect of different infusion pressures. At low pressures (such as with a 3 mm Hg rise) epithelial tight junctions appeared to be undisturbed, while at high infusion pressures (such as with a 45 mm Hg rise in pressure) epithelial tight junctions between adjacent cells appeared to be disrupted (i.e., they appeared to be physically wider than normal). Hence photomicrographic examination of tight junctions presents yet another approach to selecting pressure/flow/volume levels for site specific delivery.

Figure 26:
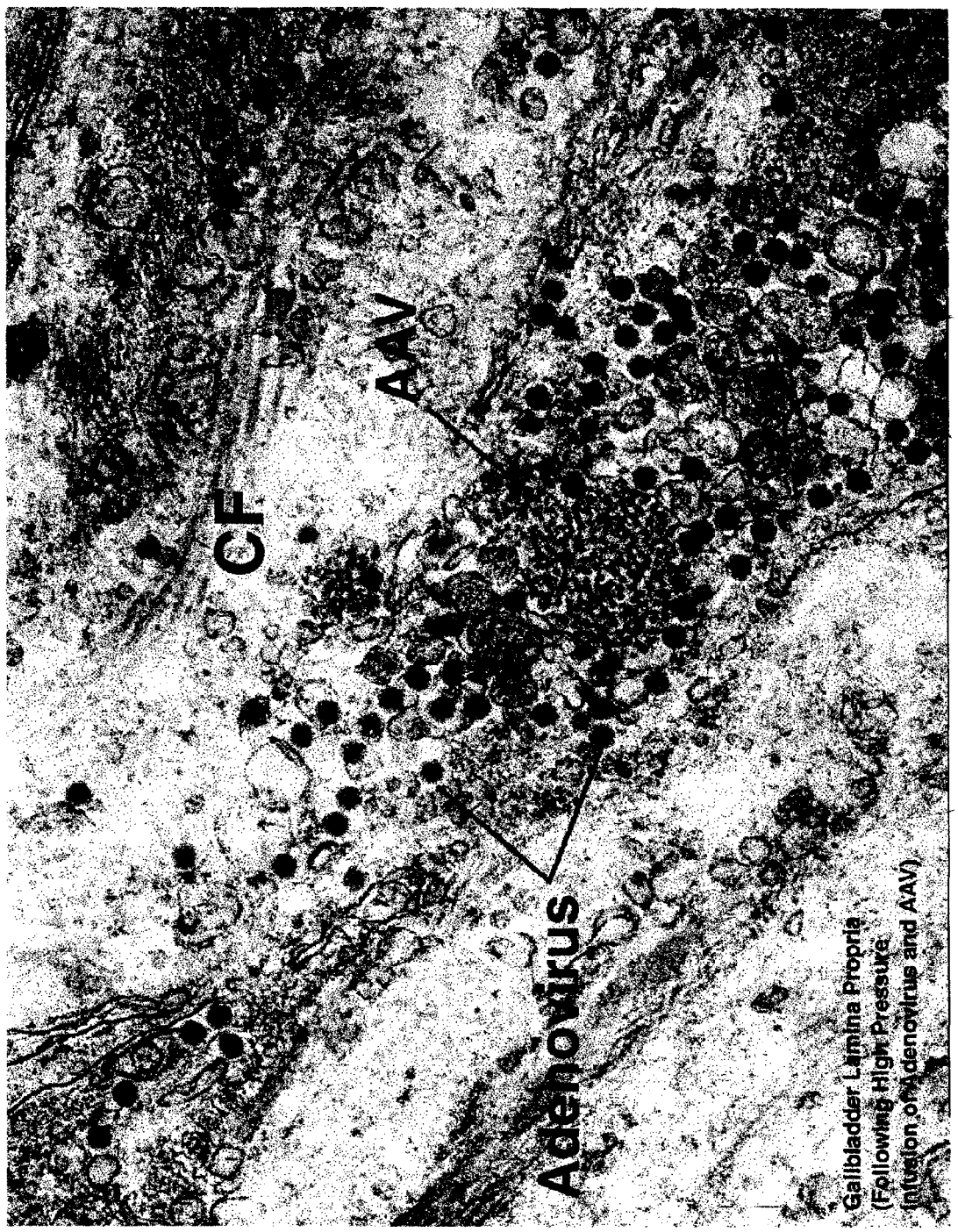
FIG. 26 is a photomicrograph showing delivery of adenovirus to the gallbladder lamina propria.
Figure 28:
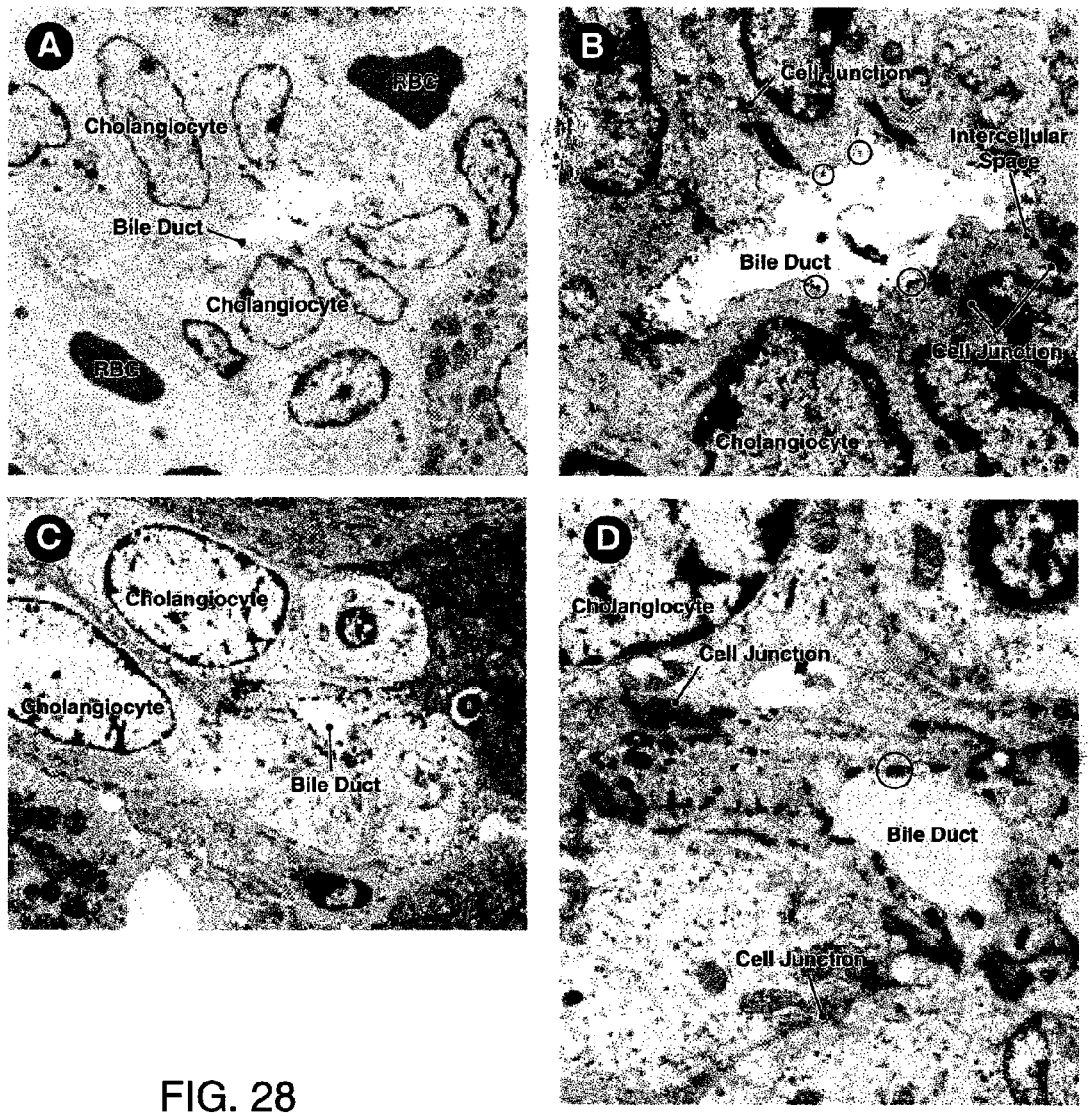
FIGS. 28A-D, 29A-E, and 30A-C are electron micrographs showing evidence of tight junction disruption achieved by methods of the present invention.
Figure 29:
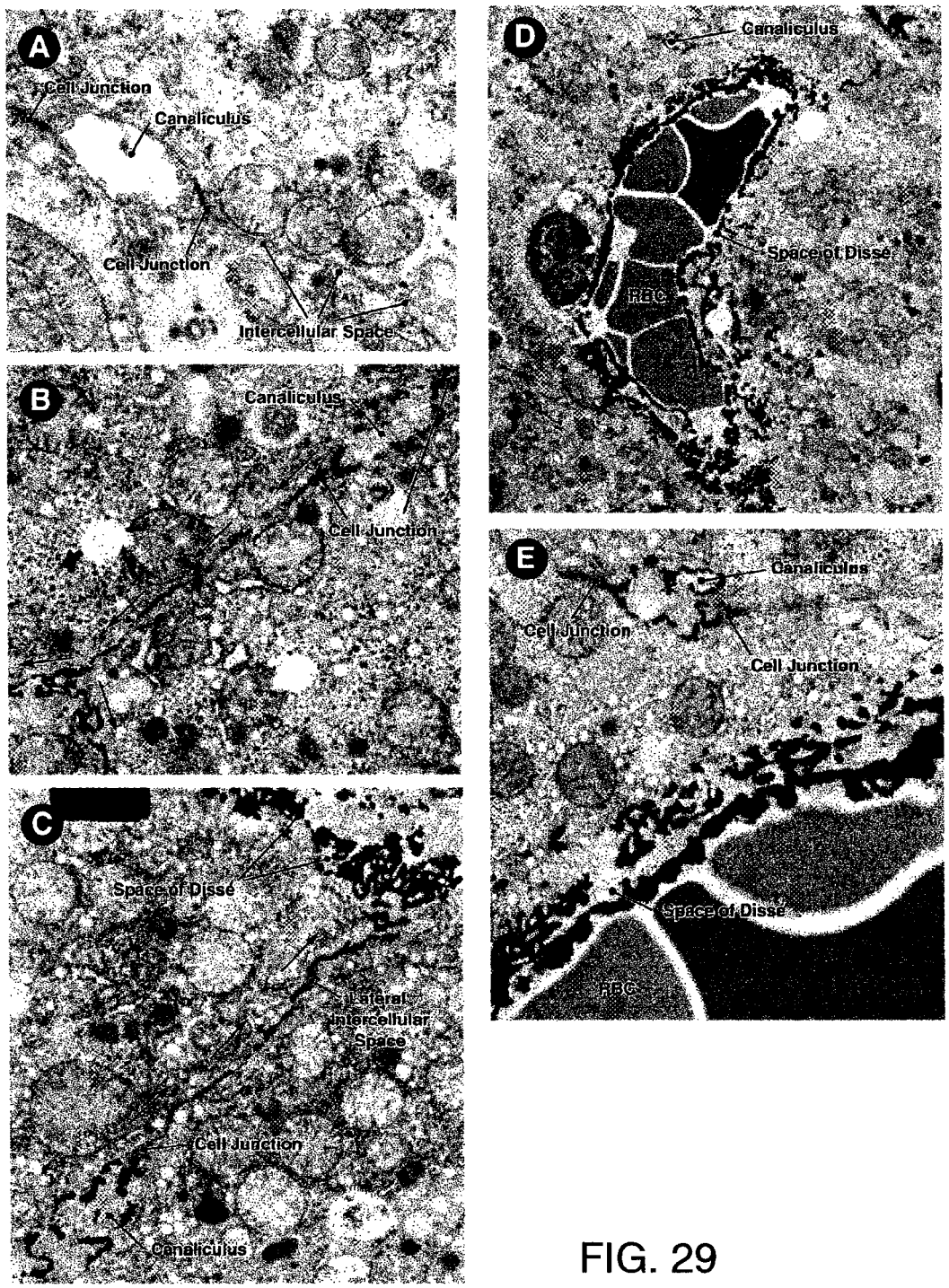

Adenovirous (AV) and Adeno-Associated Virus (AAV) were infused at either low (80 µl/20 minutes) or high (80 µl/2 minutes) rate/pressures and the gallbladders were immediately removed and examined using TEM. At low infusion pressures, viral particles were seen in the process of binding to villi and being internalized within intracytoplasmic vesicles of epithelial cells. At high infusion pressures, viral particles were seen additionally in the lamina propria (as illustrated in the photomicrograph of FIG. 26).

To determine whether the selectivity of gene transfer would also be affected by gallbladder infusion parameters, equivalent absolute viral dosages of recombinant adenovirus expressing a nuclear-localized LacZ gene were delivered at low and high infusion pressures. Tissues were removed 3 days following infusion, and evaluated using immunohistochemistry for the recombinant β-gal protein. Results for delivery of $6 \times 10^8$ plaque-forming units of β-galactosidase adenovirus were as follows: At low infusion pressures, gene transfer was confined to epithelia (7.2% positive). At high infusion pressures, gene transfer was detected in both epithelia and smooth muscle cells in the lamina propria (7.2 and 8.3% positive, respectively). These findings indicate that delivery and gene transfer to gallbladder epithelia at low intralumenal pressure selectively prevents disruption of the zona occludens, and that higher pressure infusion physically disrupts tight junctions, thereby permitting delivery of material to the gallbladder lamina propria.

EXAMPLE 7

Hepatic Lobe Specific Delivery

Figure 27:
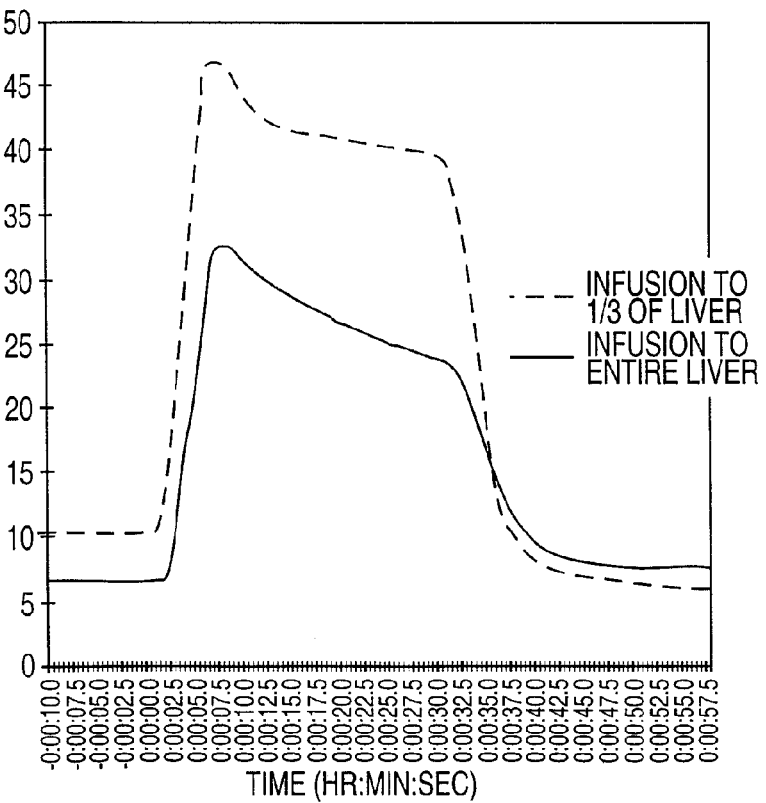
FIG. 27 is a graph of pressure versus time for delivery of an infusion into the common hepatic duct (solid line) which drains bile from the entire liver, and from a smaller duct that drains only one-third of the liver (dotted line).

This example illustrates hepatic lobe-specific delivery of vectors in mice, using a catheter as shown in FIG. 23. FIG. 27 illustrates that retrograde biliary infusion of 240 µl of 0.9% NaCl over 30 seconds to the entire liver resulted in dramatically lower pressure than achieved by 240 µl of 0.9% NaCl in 30 seconds delivered to ⅓ of the liver (right medial lobe, right lateral lobe, caudate lobe) by catheterizing and delivering the liquid into the hepatic bile duct which supplied only these lobes of the liver. Once the threshold pressure of this region of the liver was determined, β-gal adenovirus gene transfer vectors were delivered to ⅓ of the liver by infusing the adenovirus in a carrier at a volume sufficient to achieve the peak pressure at which tight junctions were apparently disrupted. Even through hepatic ductular pressure declined following the initial pressure peak (at the same volume flow), subepithelial gene transfer to hepatocytes was observed in the targeted lobes. Gene transfer was not noted outside the targeted lobes.

EXAMPLE 8

DNA Distribution Following Low Pressure Retrograde Adenovirus Biliary Infusion LacZ adenovirus was delivered by low pressure retrograde biliary infusion from the gallbladder (80 µl volume; infusion rate 0.066 µl/second) in mice. Liver tissue from these mice was evaluated by DNA in situ hybridization for the pattern of DNA distribution, which found that LacZ DNA was located primarily in bile ducts. Some DNA was also detected in immediately adjacent periductular hepatocytes. This distribution corresponds to the distribution obtained from the analysis of gene expression. Focal delivery to the bile ducts and adjacent periductular tissue in hepatic acinar zone 1 is important because there are a number of important diseases that involve this site, including hepatic fibrosis.

A similar distribution pattern was obtained by using LacZ adeno-associated virus (AAV). LacZ DNA was found in bile ducts and periductular hepatocytes 2 days following low pressure retrograde biliary infusion (80 µl volume; infusin rate 0.066 µl/second). Viral dosage administered was $3 \times 10^{10}$ Dnase-Resistant Particles (DRP)/ml. Tissue was analyzed by in situ hybridization 2 days following low pressure infusion. Tissue immunohistochemistry found LacZ gene expression at day 28 in bile duct cholangiocytes and adjacent periductular hepatocytes 28 days following low pressure infusion of $1 \times 10^{10}$ DRP of AAV.

EXAMPLE 9

Rabbit Pressure Studies

Infusion studies were performed with a multiple lumen catheter with a pressure sensor in its tip. The other lumens of the catheter permitted introduction and drainage of several liquids through separate ports. Infusion of 0.9% NaCl into the rabbit gallbladder (in which the cystic duct was occluded) resulted in characteristic pressure changes very similar to those seen with mouse gallbladder infusion and retrograde biliary infusion in mice, namely a pressure rise followed by a peak pressure, then a variable decline, and a plateau maintained during continued infusion at a substantially constant infusion rate. Once infusion was discontinued, the pressure immediately and rapidly declined towards the preinfusion baseline even though occlusion of the cystic duct was still maintained. Hence the liquid apparently continued to escape through micro-anatomic disruptions in the organ created by elevation of the intrabiliary pressure above the threshold pressure for micro-anatomic disruption.

As with the mice studies, repeat infusions produced lower peak pressures than that obtained with the initial infusion. Infusion with higher viscosity material (Hypaque) resulted in greater increases in gallbladder pressure than infusion of lower viscosity material under identical infusion conditions (i.e., identical volume and rate of infusion). Pressure was determined by the volume of the gallbladder, the volume and rate of infusion, and the viscosity of the material infused. It was possible to rinse the gallbladder without significantly raising intralumenal pressure by using low volume infusions followed by withdrawals. The low volumes/pressures of the rinses permitted the rinsing fluids to remain in the lumen substantially without epithelial or sub-epithelial administration.

After introduction of a catheter into the gallbladder of each rabbit, and occlusion of the cystic duct, low volume rinses of the gallbladder were made with very low volume rinses (e.g. 0.5 ml rinses for a gallbladder with a 1.5 ml volume), that did not significantly increase the intralumenal pressure of the organ. Then infusions were made of vehicle, DNA, or liposomes containing equivalent dosages of DNA. Very low volumes/pressures of infusions were used (infusate volume of 1 ml into gallbladders of 1.5-2.0 ml volume) to permit the infusions to remain in the lumen substantially without epithelial or subepithelial administration. Under very low pressure conditions (for example 1-2 mm Hg above the beginning pressure), no gene transfer was observed with vehicle, DNA, or liposomes. Under high pressure conditions (in which a sufficient volume was introduced into the gallbladder to reach the threshold peak beyond which microanotomic disruptions occur), gene transfer was detected with liposome delivery in gallbladder epithelia and smooth muscle in the gallbladder lamina propria. At an intermediate range volume/pressure (i.e. between the very low and high pressure conditions), delivery is substantially confined to the epithelia.

EXAMPLE 10

Minimizing Drainage

Low pressure intralumenal delivery may be combined with methods for temporarily diminishing lymphatic or venous drainage to further reduce any potential leakage into the subepithelial space. Alternatively, high pressure intralumenal delivery is combined with methods for temporarily diminishing lymphatic or venous drainage to delay and thereby diminish systemic drainage from the subepithelial space. Lymphatic or venous drainage may be temporarily reduced using direct methods such as surgical or laparoscopic occlusion of a lymphatic or venous vessel or alternatively (such as in the liver) by placement of an occluding balloon catheter in one or both hepatic veins.

High pressure intralumenal delivery is also used to achieve a non-vascular method for tissue perfusion. High pressure tissue perfusion (at least initially above the threshold pressure) may be combined with the above noted reduction of lymphatic or venous drainage so that following interstitial delivery the infused agent is given sufficient time to be taken up by target cells prior to systemic drainage. In particular embodiments, high pressure retrograde biliary infusion is combined with a device that prevents hepatic venous blood from entering the systemic circulation, but does not prevent the normal flow of blood across the hepatic parenchyma. For example, a multiple lumen balloon catheter is inserted into the hepatic vein such that when the inflated balloon seals the space between the catheter and the wall of the hepatic vein, hepatic venous blood can continue to flow into and through the catheter lumen without entering the systemic circulation. The removed blood may be treated to remove the administered agent prior to potential return of blood to the patient. In this manner, high pressure intralumenal delivery permits site directed administration of extremely high amounts of the therapeutic agent to the hepatic parenchyma without the agent subsequently entering the systemic circulation. This is particularly advantageous for achieving optimal local therapeutic concentrations of an agent that has potential systemic toxicity, while avoiding the risk of vascular complications encountered with hepatic arterial or portal venous perfusion.

EXAMPLE 11

High Pressure Retrograde Biliary Infusion Resulting in the Acute Disruption of Interhepatocyte Tight Junctions The pattern of pressure changes observed following retrograde biliary infusion, in conjunction with the finding that repetitive infusions lead to significantly lower peak intrabiliary pressures, show that retrograde biliary infusion leads to biliary ductular and/or canalicular filling, followed by leakage at a threshold pressure. Movement of fluid from the intralumenal space may conceivably occur either directly across physically opened tight junctions or indirectly by altered rates of transepithilial transcytosis. The rapidity of the observed pressure changes, however, shows that tight junction disruption is the more likely mechanism. The ability of retrograde biliary infusion to disrupt tight junctions was evaluated by qualitative ultrastructural examination of the intrahepatic distribution of lanthanum chloride, a heavy metal normally impermeant to structurally intact tight junctions.

Animals were infused retrograde with either 5 mM lanthanum chloride (Sigma) or 0.9% NaCl vehicle. Three infusions of 240 µl volume were administered per animal at a rate of 2 or 8 µl/second, with a 10 second pause between infusions. Freshly removed tissue was fixed overnight in 2% glutaraldehyde in 0.2 M cacodylate buffer. Following standard processing and embedding, 0.5 micrometer thick sections were stained with uranyl acetate and lead citrate. Sections were then examined using a Philips 201 Electron Microscope.

As shown in the electron micrographs of FIGS. 28A-D, electron dense deposits consistent with the presence of lanthanum chloride were found within bile ducts but not in their adjacent subepithelial tissue compartments following retrograde biliary infusion of 720 µl of 5 mM LaCl administered at a rate of 2 µl/second or 8 µ/second. In FIGS. 28A-D, areas with typical electron dense deposits consistent with the presence of lanthanum chloride are circled.

Electron dense deposits were found, however, within biliary canaliculi, interhepatocyte cell spaces, and the perisinusoidal Space of Disse as shown in the electron micrographs of FIGS. 29B-E. FIG. 29A is a micrograph of tissue infused with a control vehicle, while FIGS. 29B-E are micrographs of experimental tissues. The arrows denote the interpreted pathway of paracellular leakage.

Figure 30:
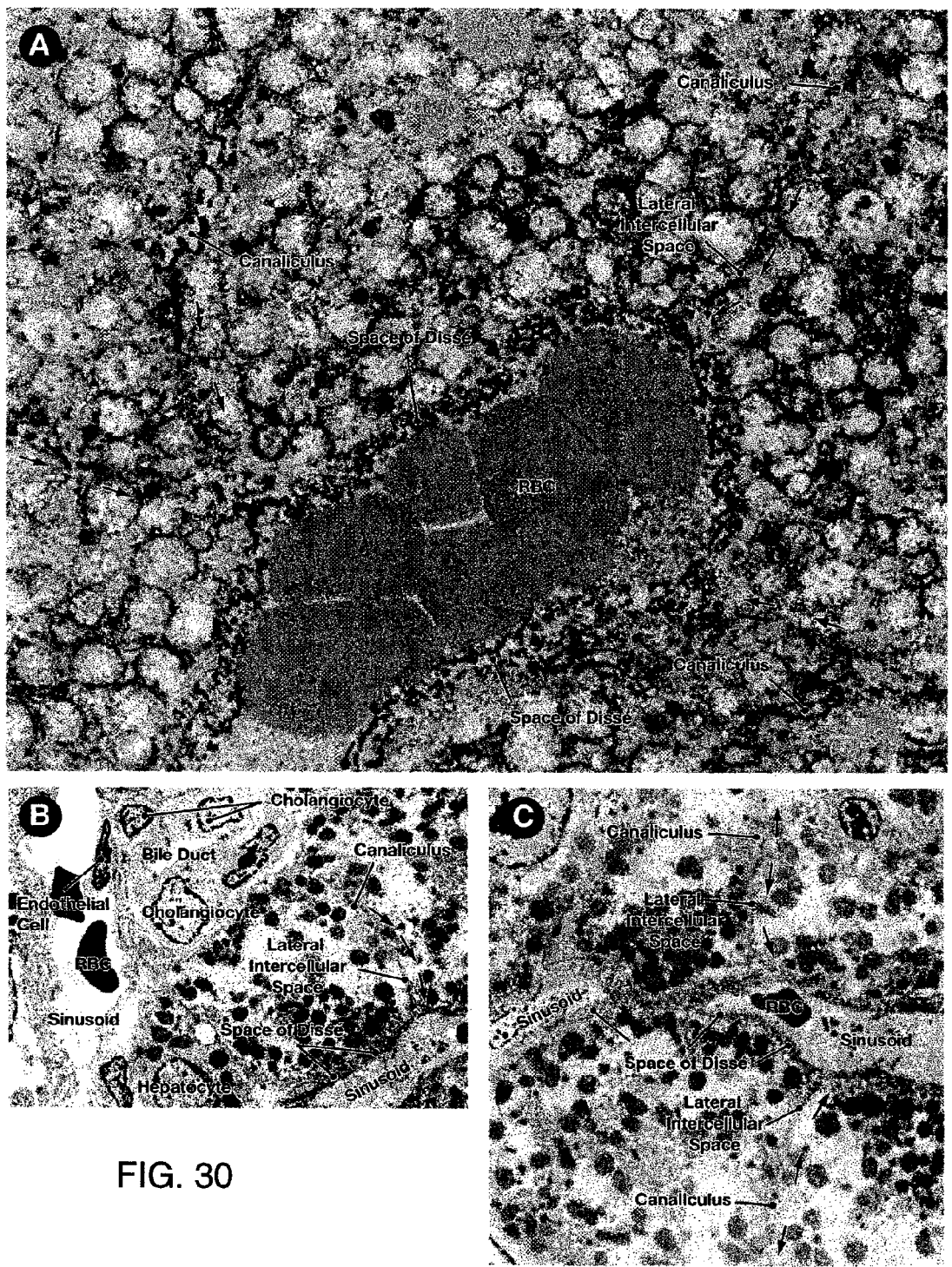

The electron micrographs of FIGS. 30A-C show the probable overall pathway, indicated by the arrows, taken by high pressure retrograde biliary infusate: from biliary canaliculi to their adjacent subepithelial compartments, viz, from the canalicular lumen across disrupted canalicular tight junctions into the lateral intercellular space and subsequently into the perisinusoidal Space of Disse.

The presence of LaCl within interhepatocyte cell spaces and the perisinusoidal Space of Disse immediately following high pressure retrograde biliary infusion is consistent with an acute alteration of tight junction permeability. It is also possible (but unlikely within the timeframe of these experiments) that active transport (including transcytosis) resulted in the observed movement of lanthanum chloride from the intralumenal space to the lateral intercellular space and the Space of Disse. In addition to the short timeframe, the likelihood of an alteration in tight junction permeability rather than transcytosis is also supported by the failure to find ultrastructural evidence of lanthanum chloride particles intracellularly within either hepatocytes or cholangiocytes.

EXAMPLE 12

Chronic Cholestasis Reducing the Peak Intrabiliary Pressure Response to Retrograde Biliary Infusion Intra- and extra-hepatic cholestasis are common clinical situations that provide a useful test system for evaluating the potential applicability of pressure-mediated delivery in the setting of disease. In order to determine the effect of chronic cholestasis on the dynamic response of the biliary system to retrograde biliary infusion, a group of animals underwent 4 days of chronic extrahepatic bile duct obstruction. Following the induction of anesthesia a midline laparatomy was made and the common bile duct visualized. A 6-0 silk tie was used to occlude the common bile duct rostral to the junction with the pancreatic ducts. The abdominal incision was closed in two layers with 6-0 silk. Four days later, the animals were reanesthetized and underwent a repeat laparotomy. A microvascular clip was placed above the level of the common bile duct occlusion and a catheter secured within the common bile duct. The microvascular clip was then removed and baseline intrabiliary pressure determined. A gallbladder catheter was then secured in position and animals received retrograde biliary infusion as described above.

Biliary manometry was then performed using a range of retrograde biliary volumes and rates of infusion with the results as shown in FIG. 31. Intrabiliary pressure following 4 days of cholestasis was compared to the values shown above (time=0 minutes: non-obstructed; time=10 minutes: 10 minutes of common bile duct obstruction). After 4 days of chronic extrahepatic bile duct obstruction, baseline (pre-infusion) intrabiliary pressure remained significantly elevated (normostasis baseline, 0.8±0.2 mm Hg [n=5] versus 4 days of cholestasis, 8.2±1.0 mm Hg [n=10]; p<0.05). The pre-infusion intrabiliary pressure after 4 days of cholestasis was not significantly different from the pressure level following only 10 minutes of biliary tree obstruction (10 minutes of cholestasis, 10.0±1.4 mm Hg [n=5] versus 96 hours of cholestasis, 8.2±1.0 mm Hg [n=10]; p>0.05).

Figure 31A:
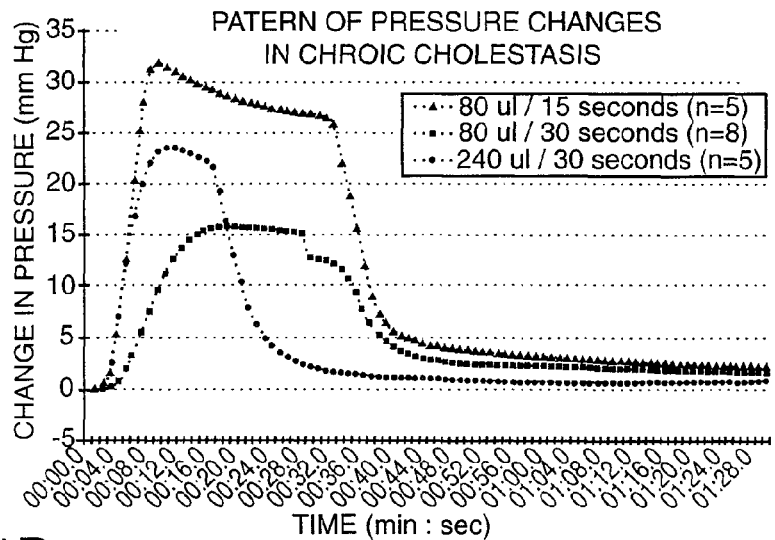
FIG. 31A is a graph of the pattern of pressure changes observed following retrograde biliary infusion in chronically cholestatic animals
Figure 31B:
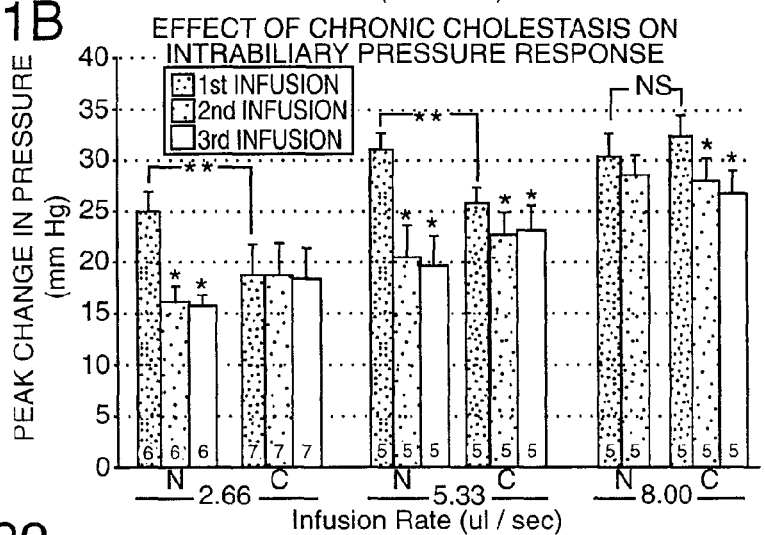
FIG. 31B is a histogram comparing the effects of repeat retrograde biliary infusion on intralumenal pressure in normostatic and chronically cholestatic animals.

FIG. 31A shows that cholestatic animals had a similar pattern of pressure changes as those seen for normostatic animals, viz, a progressive rise in intralumenal pressure until a peak pressure was reached, a slight decline in pressure, and then a plateau pressure that was sustained until the infusion was completed. Once the infusion was stopped, pressure immediately underwent a rapid decline toward the preinfusion value. As in normostatic animals, pressure changes in cholestatic animals were also dependent upon the infusion rate and volume. Greater peak pressures were achieved with faster infusion rates and the pressure rose more rapidly with time at the higher infusion rates. Peak pressures were similarly infusion rate-dependent; at a given infusion volume, increasing the infusion rate resulted in peak pressures significantly different ($p<0.05$) from those obtained using slower infusion rates, as may be seen in FIG. 31B. Pressures at the end of infusion were also dependent upon both the infusion rate and volume. Unlike normostatic animals, postinfusion pressures did not tend to be lower following larger volume, more rapid infusions.

In both normostatic and cholestatic animals, repeat retrograde biliary infusion tended to result in lower peak intrabiliary pressures than the initial infusion, as shown in FIG. 31C. However, this effect was more pronounced with the normostatic animals as they tended to have significantly greater maximal changes in intrabiliary pressure after an initial infusion than cholestatic animals for a given infusion rate and volume. At larger volumes and more rapid rates of infusion, the differences between normostatic and cholestatic animals became less pronounced.

EXAMPLE 13

Retrograde Biliary Infusion Resulting in Tight Junction Disruption in Both Normostatic and Cholestatic Animals In order to determine the effect of retrograde biliary infusion on tight junction permeability under both normostatic and cholestatic conditions, [14C]-sucrose was infused retrograde using a range of infusion rates and volumes in naive mice and following 4 days of chronic extrahepatic bile duct obstruction. Following a midline laparotomy, both ureters were identified and occluded with microvascular clips. A catheter was placed within the gallbladder lumen and the common bile duct occluded using a microvascular clip placed above the junction of the common bile duct with the superior pancreatic duct. Retrograde biliary infusions (22° C.) of 0.9% NaCl or 2 µCi of [14C]-sucrose (Amersham Pharmacia Biotech, Inc., Piscataway, N.J.) diluted in 0.9% NaCl were then administered using a range of volumes and rates of infusion. Five minutes following the completion of the infusion, a midsternal incision was rapidly made and blood obtained by intracardiac puncture using a 27 gauge needle and a syringe. Blood was immediately added to a 1.5 ml microcentrifuge tube containing 10 units of sodium heparin (Elkins-Sinn, Cherry Hill, N.J.) and centrifuged at 4,000 RPM for 5 minutes. Two hundred µl of plasma were removed and added to a glass vial containing 15 ml of scintillation solution (National Diagnostics, Atlanta, Ga.). Radioactive counts (cpm) were determined in a scintillation counter (Beckman). Since physically intact tight junctions are impermeable to sucrose, the appearance of [14C]-sucrose in the systemic circulation under these experimental conditions would signify that tight junction disruption had occurred.

Figure 32:
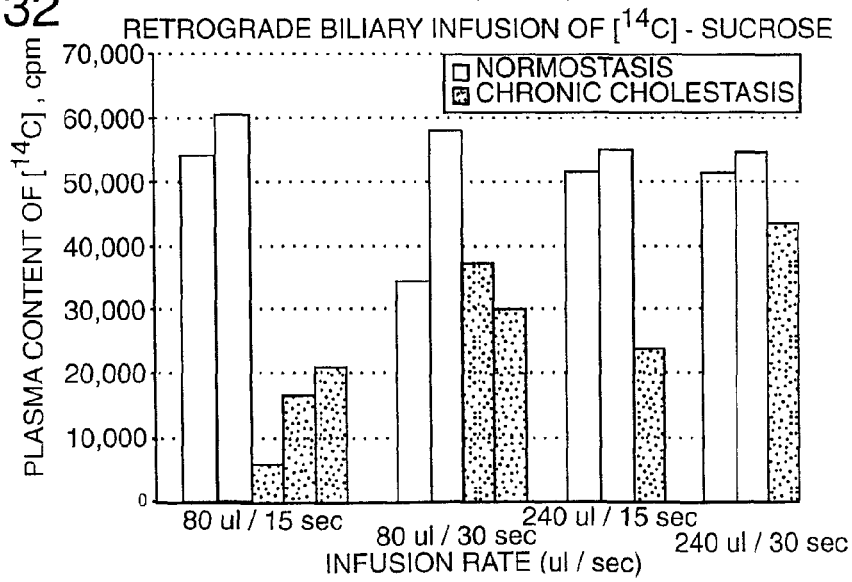
FIG. 32 is a histogram showing plasma content of a tracer molecule following retrograde biliary infusion in both normostatic and cholestatic conditions.

FIG. 32 shows the results of the experiment. In normostatic animals, systemic leakage of [14C]-sucrose at 5 minutes postinfusion was detected at approximately equivalent levels across a range of infusion rates and volumes. In cholestatic animals the amount of leakage tended to be lower than for normostatic animals at a given infusion volume and rate. In cholestatic animals increasing infusion volume or infusion duration tended to lead to greater amounts of paracellular leakage.

In cholestatic animals, retrograde biliary infusion resulted in significantly lower peak intrabiliary pressures during a first infusion than were observed under first infusion conditions in normostatic animals. This shows that chronic extrahepatic bile duct obstruction resulted in some degree of tight junction disruption independent to any induced by retrograde biliary infusion. However, cholestatic animals also tended to have smaller amounts of [14C]-sucrose in the bloodstream 5 minutes following retrograde biliary infusion than did normostatic animals. One explanation for this apparently contradictory finding is that peak intrabiliary pressure may directly affect the diameter to which tight junctions are opened and/or the driving force for paracellular movement, and thereby determine the amount of paracellular leakage of molecules of a particular diameter. Hence in the present experiments the tight junction disruption known to be caused by cholestasis was sufficient for there to be some amount of leakage of molecules smaller than sucrose (e.g., water) during a retrograde biliary infusion. This fluid leakage would have minimized the extent of the peak intrabiliary pressure rise achieved during a retrograde biliary infusion. This smaller peak intrabiliary pressure in turn could have diminished the number of tight junctions that were acutely widened to the degree that molecules of the diameter of sucrose would acutely pass through, or alternatively may have reduced the driving force (pressure gradient) driving the paracellular movement of sucrose across disrupted tight junctions. This example illustrates that it is possible to determine a range of different diameter molecules and infusion pressures that are desirable to more precisely determine a correlation between the absolute level of intrabiliary pressure, the degree of tight junction disruption, and the amount of paracellular leakage.

EXAMPLE 14

Intralumenal Delivery to the Rabbit Urinary Bladder

Figure 33A:
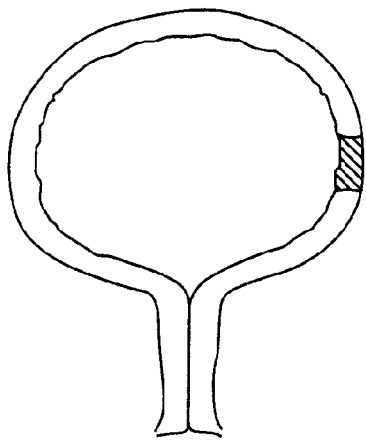
FIGS. 33A-D are cross-sectional diagrams of the urinary bladder showing the response of the urinary bladder the filling thereof.
Figure 33B:
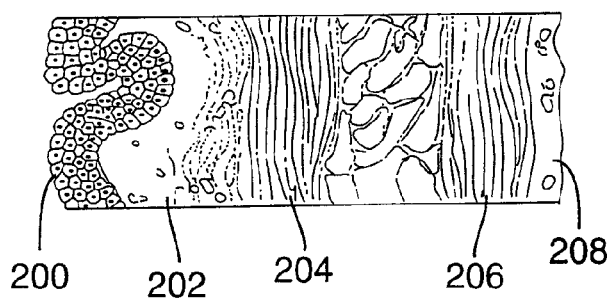
Figure 33C:
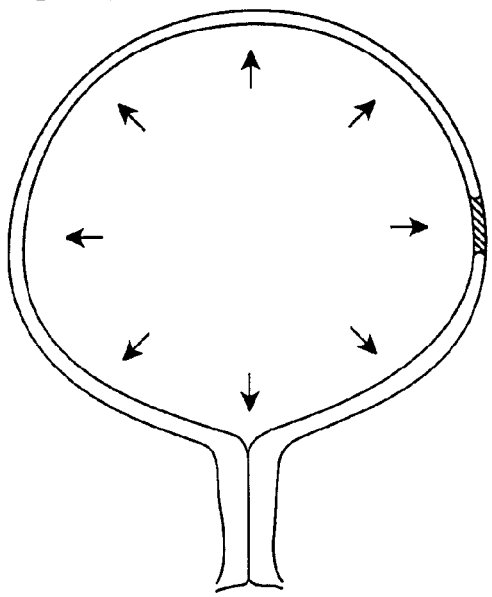
Figure 33D:
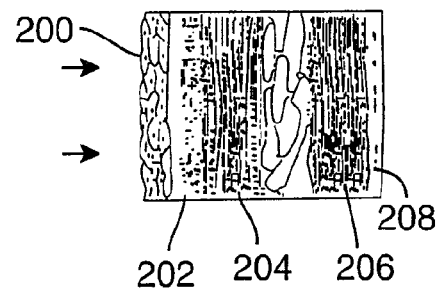

The genitourinary system is another example of a lumenal structure amenable to pressure-mediated delivery. FIGS. 33A-D are schematic cross-sections of a urinary bladder illustrating the effect of urinary bladder filling upon the histological compartments of the bladder. FIG. 33A shows a cross-section of the urinary bladder in a relatively empty state (where 200 is the transitional epithelium, 202 is the lamina propria, layers 204 and 206 are muscle, and 208 is adventitia. FIG. 33B shows an enlarged view of the non-compressed wall section highlighted in FIG. 33A. FIG. 33C shows a cross-section of the urinary bladder in a relatively full state, and FIG. 33D shows an enlarged view of the compressed wall section highlighted in FIG. 33C. The arrows indicate the direction of the pressure exerted by the contents of the bladder.

Both slow, passive filling from storage of urine, and active filling through acute volume or pressure-mediated expansion, cause a compression of the layers of the urinary bladder, as illustrated in FIGS. 33A-D. Retrourethral catheterization is a well-described method for delivery to the urinary bladder. However, the effect of urinary bladder pressure on molecular delivery has not previously been characterized. In particular, use of urinary bladder pressure to insure selective delivery of agents to either the surface epithelial cells or to deeper histological sub-compartments, including the lamina propria and muscular layers has not previously been characterized.

As an experimental model to mimic retrourethral delivery, male Dutch Belted Rabbits (1-2 Kg BW) had PE-50 tubing placed in the lumen of each urethra and advanced so that the tips were within the lumen of the urinary bladder. One ureteral catheter was connected to a pressure transducer and used for recording intralumenal pressure. The other ureteral catheter was connected to a microinfusion pump. Microvascular clips were placed on the ureters to prevent retrograde reflux.

The urethra was occluded using a vascular loop. 5 mM Lanthanum Chloride was infused so that the intralumenal pressure was either 25 mm Hg or 50 mm Hg.

Tissues were removed 10 minutes later and processed for electron microscopy. At 25 mm Hg, electron dense deposits were detected in the intercellular spaces between epithelial cells. At 50 mm Hg, there was some evidence of patchy epithelial denudation. Following the administration of 200 nm fluorescent latex microspheres at 50 mm-100 nm intralumenal pressure, the urinary bladder was removed and processed for fresh-frozen sections. Evaluation of fresh-frozen sections using fluorescent microscopy revealed the presence of microspheres in the lamina propria immediately adjacent to the first muscle layer. These results indicate that at elevated intralumenal pressures, urinary bladder infusate can be delivered across epithelial cell tight junctions.

Figure 34:
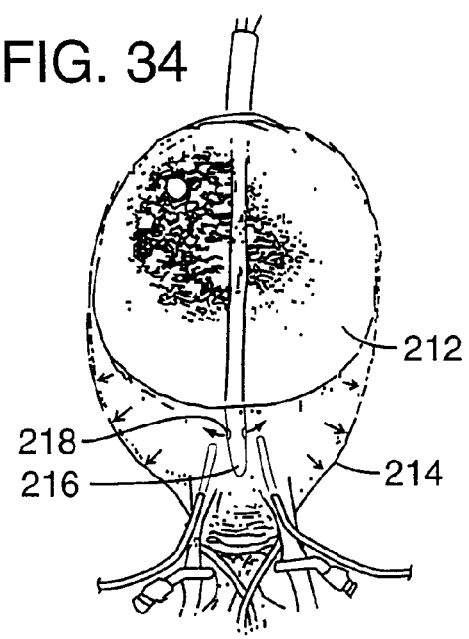
FIG. 34 is a partial cross-section of a urinary bladder prepared for study as described herein, and showing used of a Foley catheter in accordance with a method of the present invention.

Under some circumstances it may be useful to reduce the total volume of infusate that must be delivered to an intralumenal site. This would be particularly advantageous if the infusate is particularly costly or difficult to obtain. Accordingly, intralumenal balloons may be used in combination with pressure mediated delivery, in order to reduce the volume of infusate that must be delivered, while still taking advantage of the benefits of pressure-mediated intralumenal delivery. The balloon(s) are expanded prior to infusate administration in order to reduce the volume of infusate that must be delivered. A working application of this technique is shown in FIG. 34, in a bladder prepared as described above, where the intralumenal balloon 212 is shown in a urinary bladder 214, with the tip 216 of the catheter having orifices 218 through which infusate can be delivered. A 3.5 French Foley catheter was introduced into the lumen of the urinary bladder and inflated. This permitted delivery of a reduced volume of infusate to the urinary bladder, while still permitting administration at elevated intralumenal volumes/pressures.

EXAMPLE 15

A Constant Pressure Delivery Device

The results presented above indicate that intralumenal delivery of infusate to structures lined by either epithelial cells or endothelial cells may be selectively targeted to either the luminal surface or to deeper subepithelial or subendothelial histological compartments by selection of appropriate delivery parameters. It may be particularly useful to administer agents under steady-state conditions, in which delivery pressure is maintained constant irrespective of how the tissue responds to the infusion. For example, under non-steady state delivery conditions, opening of tight junctions or expansion in size of a structure will affect the intralumenal pressure. Steady-state delivery bypasses this feature, permitting delivery at constant, pre-determined pressures.

Figure 35:
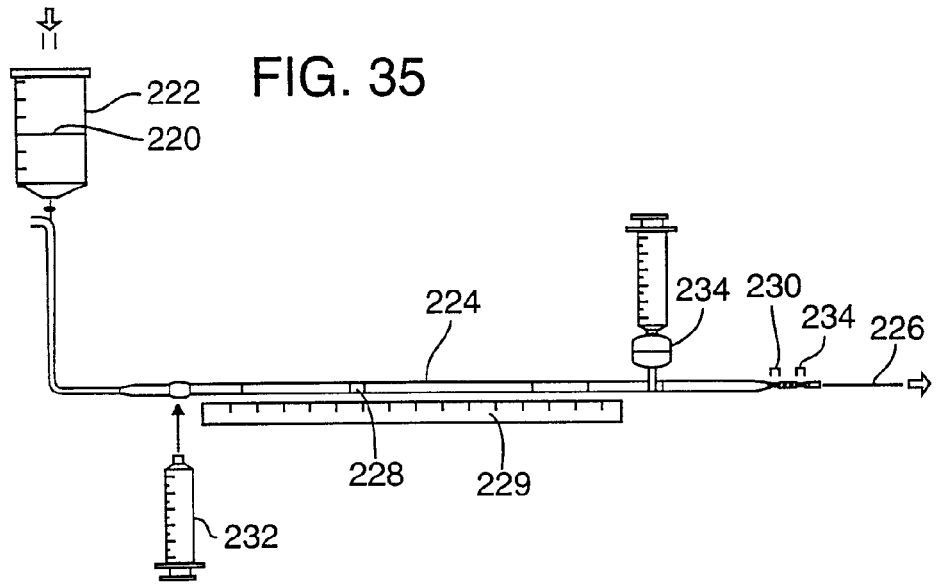
FIG. 35 is a diagram of an example of a constant-pressure infusion device.

FIG. 35 is a diagram of a working example of a system for constant-pressure intralumenal delivery. A manometrically-controlled nitrogen-gas/fluid interface 220 in a fluid infusion reservoir 222 permits constant pressure administration. A working model was regulated using an adaptation of a Cole-Palmer pressure controller. Infusion fluid from the reservoir flows through capillary glass tubes 224 on its way to an infusion line 226. Flow rates may then be determined by tracking air bubbles 228 in the capillary glass tubes 224 with a ruler 229. A pressure sensor 230 detects the pressure of the infusion fluid at a location near the infusion line 226.

To set up the system, fluid was added to the reservoir, and the system was rinsed and filled with fluid. The infusion line 226 was then surgically placed into the animal's organ. When the system was started, a pneumatic servo-pressure controller (not shown) provided a constant air pressure to the top of the liquid level at interface 220 in the reservoir 222. By adjusting the controller setting the desired pressure could be obtained at the pressure sensor, which was kept at the same height ($z=0$) as the animal. The reading at the pressure sensor was thus equal to the applied pressure (the pump pressure) plus the pressure head (the pressure increase due to the change in height between the top of the liquid level in the reservoir and the height of the infusion line). The infusion line was kept at the same height as the pressure sensor and the animal on the operating table. Alternate systems could be of course be adapted in which a constant pressure is maintained at the pressure sensor and not at the top of the Reservoir. This would be most important when a large volume of fluid is infused. Specifically, if the pressure control is provided at the top of the reservoir, then when a large amount of fluid is infused, the pressure has to be slowly increased to account for the decreasing pressure head.

When the system is started, a constant pressure infusion is delivered to the animal. The infusion pressure and internal organ pressure may be recorded over time. For example, this was done for rabbit urinary bladder experiments by placing a second catheter in the bladder, which was connected to a pressure transducer. As one alternative of the present invention, the intralumenal pressure may measured through the tip of the delivery catheter, and this pressure may be used to control the pressure of the infusion fluid, such as at the nitrogen-gas/infusion-fluid interface.

The flow rate of infusion fluid was experimentally recorded in the following way: the cross sectional area of the bubble tube was determined by injecting a known volume of water (from syringe 232) into a measured length of the bubble tube. The cross sectional area was 0.0233 $cm^2$ (0.35 cc in 15 cm). When the flow started, an air bubble was slowly injected into the infusion fluid flow. The bubble then traveled down the bubble tube. At the end of the tube, the bubble would rise up into the bubble trap 234 and displace an equal volume of liquid. For each bubble 25 time points were recorded, on 1-cm intervals of ruler 229. The time versus distance that the bubble had traveled could be plotted and the slope of this line was the velocity of the bubble. Multiplying the slope by the cross sectional area of the bubble tube gave the average flow rate of the infusion fluid. This method of flow rate measurement is a working and experimental model for the purpose of illustration. In practice, flow rates may also be determined by ultrasonic or other methods known to those of skill in the art.

EXAMPLE 16

Constant-Pressure Delivery to the Rabbit Urinary Bladder

As a working model, the delivery setup described in Example 14 was utilized with the modification that a ureteral catheter was connected to the constant pressure administration device. One catheter delivered the infusion fluid; the other measured the internal bladder pressure (this was also recorded over time). The bladder was drained through the infusion catheter, rinsed twice with saline, and then once with the infusion fluid. The bladder was then primed until it reached the desired steady state pressure, the same pressure that the constant pressure system was set to apply for the experiment.

Rinsing and initial filling the bladder was accomplished with a syringe through a stopcock 234 (FIG. 35). Once the internal bladder pressure reached the desired experimental pressure, stopcock 234 was turned to allow flow from the constant pressure system into the infusion line. Then 0.9% NaCl was administered at sustained constant-pressures of 5-50 mm Hg for periods of 60 to 90 minutes. When the constant pressure system was switched on, there was an initial drop in the internal bladder pressure. This was probably due to the difference between the pressure applied from the syringe and the pressure applied from the system. The pressure applied by the syringe to raise the internal bladder pressure to the desired pressure was often 10 times greater than the pressure that the constant pressure system was applying (which was the same as the desired pressure). So the drop in the internal bladder pressure corresponded with the drop in applied pressure.

Figure 36:
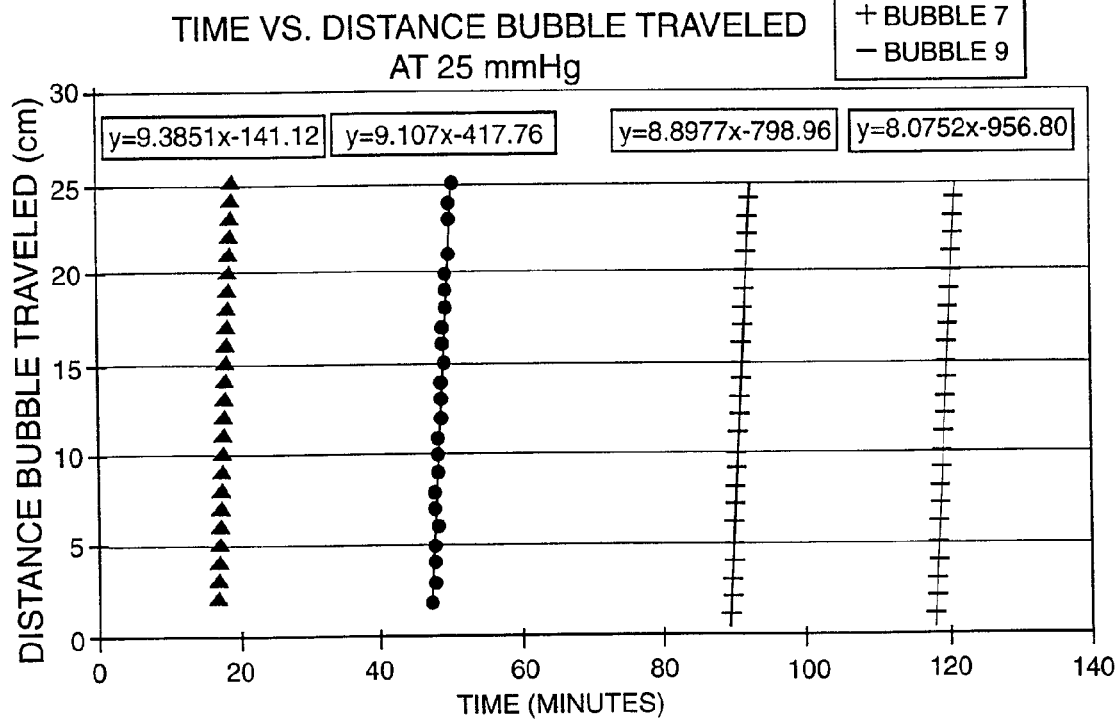
FIG. 36 is a graph of bubble travel observed in a urinary bladder infusion performed with the infusion device of FIG. 35.
Figure 37:
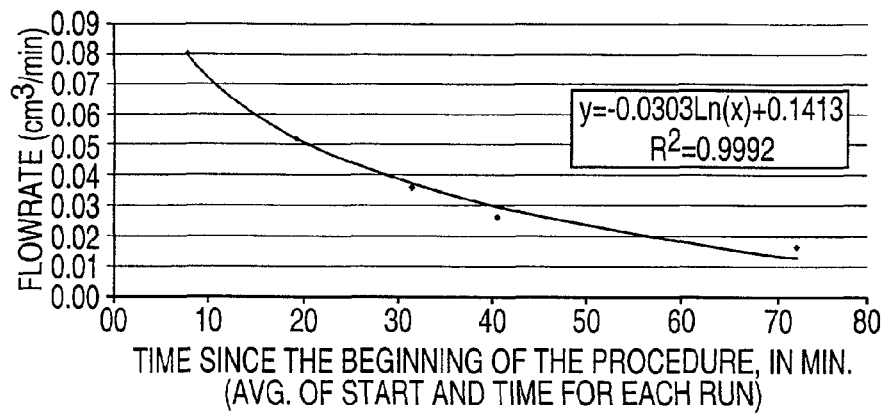
FIG. 37 is a graph of flow rate versus time in a constant-pressure urinary bladder infusion.

Flow rates were directly dependent upon administration pressure. The flow rate for the entire infusion time was not constant. But over shorter intervals, the time for a bubble to travel through the bubble tube, the flow rate was relatively constant. FIG. 36 shows a typical time versus bubble distance plot for selected bubbles in constant-pressure intralumenal administration to a Rabbit urinary bladder. The slopes of the bubble plots decrease over time. Each calculated flow rate could then be plotted with respect to time (average of the time of d=1 cm and d=25 cm). For rabbit urinary bladder infusions the flow rates decreased with a logarithmic shape. FIG. 37 is a typical time versus flow rate graph for a rabbit urinary bladder infusion.

During experiments, the bladder appeared to slowly expand as the muscles relaxed. When the desired pressure was low (e.g., 25 mm Hg), the internal pressure would reach the desired pressure in 45-70 minutes. Once the internal bladder pressure reached the desired or infusion pressure, the flow into the bladder would stop. If the desired pressure was high (e.g., 50 mm Hg), the internal pressure would not always reach the desired pressure in the 90 minute dwell time.

Figure 38:
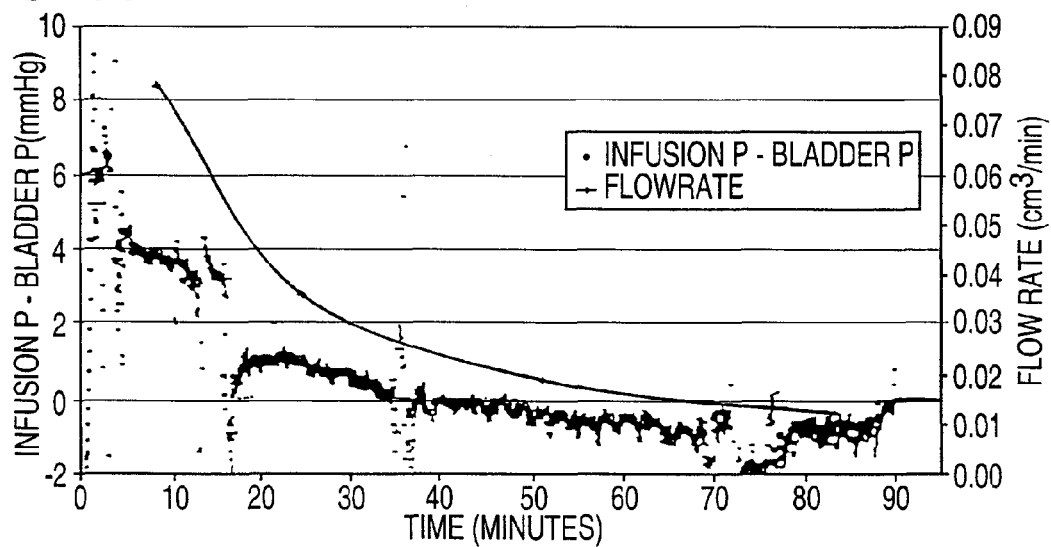
FIG. 38 is a graph of the differences in pressure (applied pressure versus internal bladder pressure) verses time and flow rate versus time.

The difference between the infusing and internal bladder pressure was proportional with the flow rate into the bladder. When the differences in pressure (applied pressure versus internal bladder pressure) were plotted verse time and flow rate (on a second y-axis), the two plots showed similar shapes. This was true for all rabbit bladder infusions. FIG. 38 is a typical graph.

Figure 39:
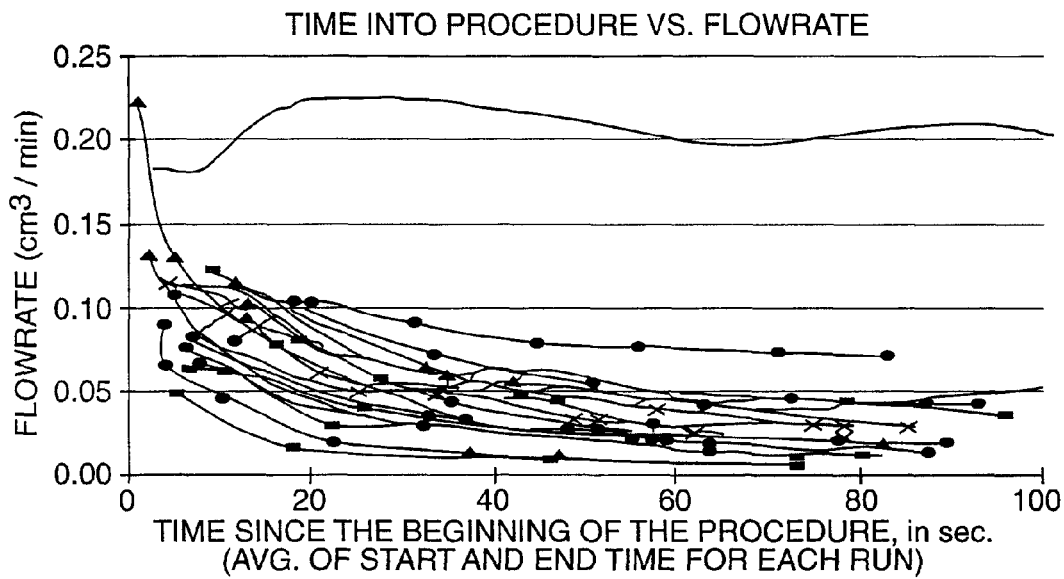
FIG. 39 is a graph of flow rate versus time for a number of different bladders.
Figure 40:
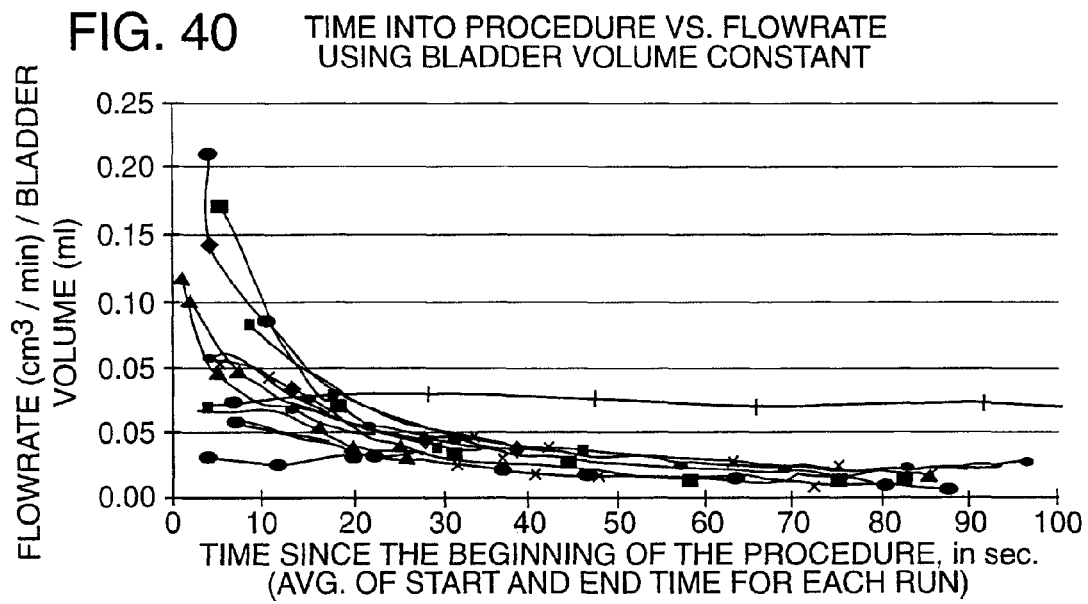
FIG. 40 is a graph of flow rate over bladder volume versus time for the bladders of FIG. 39.

Plots of flow rate versus time for rabbit bladder infusions had the same shape even for different infusion pressures and flow rates. The initial bladder volume turned out to be a useful normalizing factor to relate flow rate versus time (see FIG. 39). The initial bladder sizes of rabbits vary by at least a factor of ten. If the flow rates ($cm^3$/min) were divided by primed bladder size (5.5 cc-78 cc), the amount of fluid that had to be added to get the bladder to the desired pressure, then the time versus (flow rate)/(primed bladder size) curves converged when graphed on one chart. This can be seen in FIGS. 39 and 40.

Urinary bladder volumes were also determined during constant pressure infusion using externally fixed ultrasonic crystals (Sonometrics, Toronto) and continuous measurement of longitudinal, medial, and ventral-dorsal diameters. Bladder shape was assumed to be ellipsoidal. Steady state infusion at a range of sustained constant infusion pressures resulted in flow into the urinary bladder at rates that were dependent upon the delivery pressure. At higher constant infusion pressures flow rates were correspondingly increased. Constant pressure infusion into the rabbit urinary bladder for 120 minutes at a steady state pressure of 25 mm Hg resulted in flow rates that declined with time. The volume of material infused was completely accounted for by changes in total urinary bladder volume (urinary bladder luminal contents+bladder wall thickness). This shows that passive stretch of the bladder resulted in a progressive reduction in flow rates over time at a constant infusion pressure of 25 mm Hg. In contrast, constant pressure infusion for 120 minutes at a steady state pressure of 50 mm Hg resulted in a sustained flow rate that did not decline with time. Urinary bladder volume did not significantly increase during the delivery period, indicating that fluid movement across the urinary epithelium accounted for the sustained flow rates at constant infusion pressures of 50 mm Hg.

In the urinary bladder, the rate of delivery of certain sized therapeutics to the subepithelial compartment appears to be influenced by the level of initial constant pressure exposure as well as the sustained pressure level once the epithelial tight junctions have been disrupted. [14C]-sucrose (3.8 µCi/ml) was administered at constant infusion pressures of 25, 37.5, and 50 mm Hg for 120 minutes. A heparinized jugular venous catheter was utilized to obtain plasma samples at t=−5, 0, 1, 2, 3, 4, 5, 10, 20, 30, 60, 90, and 120 minutes. 400 µl of plasma was then evaluated for 14C content (cpm). Since the experiments described above had resulted in TEM evidence of tight junction disruption and deposition in the lamina propria of 200 nm latex microspheres at 25-50 mm Hg, it would have been predicted that Sucrose would have also entered the lamina propria and then subsequently traveled via venous and/or lymphatic drainage into the systemic circulation. However, no evidence of systemic [14C]-sucrose leakage was detected. Instead, radioactive evidence of [14C]-sucrose was detected on gauze placed on the external surface of the urinary bladder.

This shows that sustained elevations of intralumenal bladder pressure may result in microherniations, providing a pathway for rapidly transiting across the urinary bladder. Selection of appropriate infusion conditions, such as an initial pulsatile disruption of tight junctions followed by sustained constant low pressure delivery at 5-10 mm Hg may permit the slow perfusion of the subepithelial space with smaller molecules.

EXAMPLE 17

Constant Pressure Retrograde Biliary Infusion in Mice

Constant pressure infusion was evaluated in mice using the retrograde biliary infusion setup described previously. The constant pressure device was substituted for the microinfusion pump. [14C]-sucrose (molecular weight 342; 3.8 µCi/ml) was administered to both normostatic and chronically cholestatic mice (4 and 21 days of chronic extrahepatic bile duct occlusion). Infusion flow rates were recorded using the bubble tube method described above. Blood samples were obtained and evaluated as described above.

Flow rates for murine biliary infusions were constant for the entire dwell time, unlike the rabbit bladder flow rates that decreased over time. As in the rabbit urinary bladder experiments, constant pressure retrograde biliary infusion resulted in flow rates that were direct functions of administration pressure.

Figure 41:
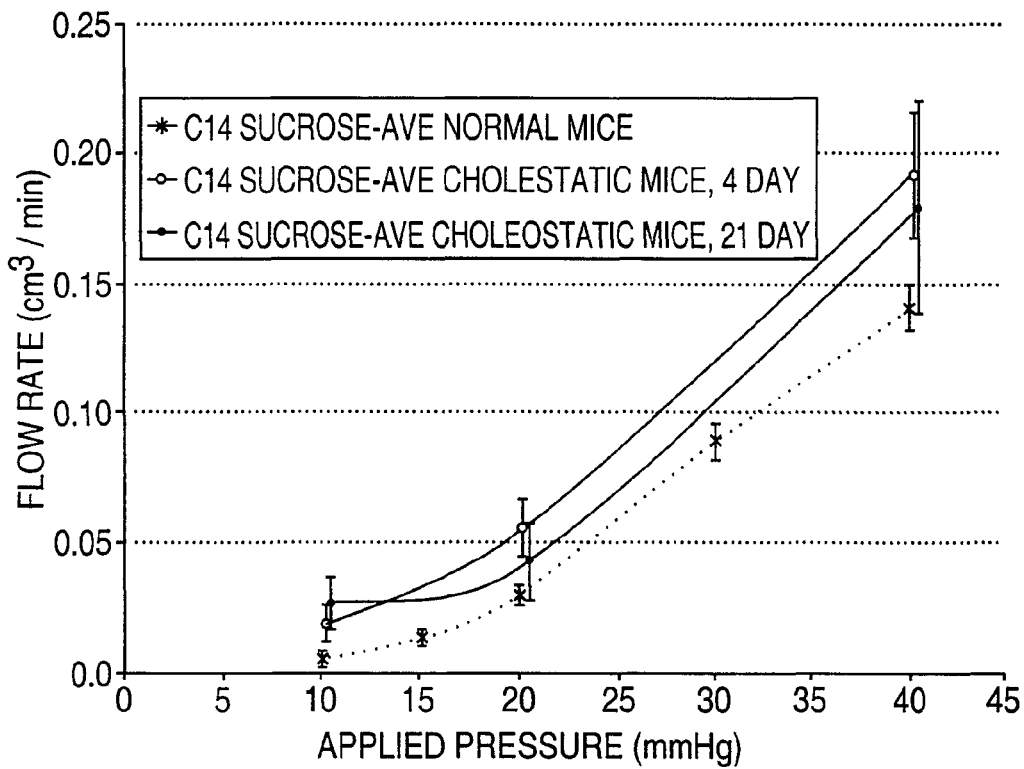
FIG. 41 is a graph of flow rates of murine biliary infusions as a function of applied pressure in normostatic and chronically cholestatic animals.
Figure 42:
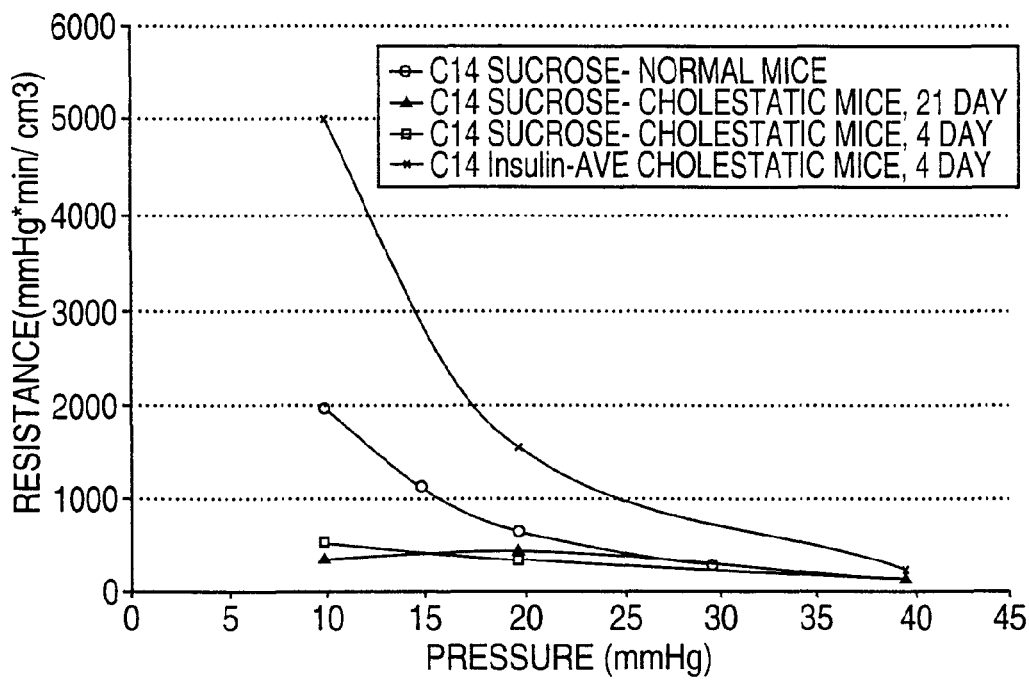
FIG. 42 is a graph of resistance (applied pressure/flow rate) at different constant pressures of murine biliary infusions.

FIG. 41 is a graph of infusion flow rate as a function of applied pressure in normostatic and chronically cholestatic mice. FIG. 42 is a graph of resistance (applied pressure/flow rate) at different constant pressures. Resistance to flow is greatest at the lowest infusion pressures and declines as infusion pressure is increased. Chronic extrahepatic bile duct obstruction is known to disrupt intrahepatic tight junctions and this is reflected in a decreased resistance to flow in these animals.

Under constant pressure conditions solutes normally excluded by an intact tight junction were detected in the systemic bloodstream. Solutes evaluated included sucrose (molecular weight 370), inulin (molecular weight 5,200), and Dextran (molecular weight 70,000). At lower infusion pressures, solutes of greater molecular weight exhibit greater resistance to flow (see FIG. 43: 4 day inulin versus 4 day sucrose) and slower flow rates (see Table 1 below). Table 1 compares flow rates for [14C]-sucrose and [14C]-inulin at different infusion pressures, listing flow rates, resistances, and levels of paracellular leakage (average counts).

TABLE 1

Constant Pressure Infusion

| Pressure mmHg | n = | Flowrate cm$^3$/min | STDEVP (Flow) | SEM (Flow) | Ave Counts | Resistance (P/flow rate) mmHg*min/cm$^3$ | STDEVP (Resist) | SEM (Resist) |
|---|---|---|---|---|---|---|---|---|
| C14 Sucrose Normal Mice (Average) | | | | | | | | |
| 10 | 24 | 0.0051 | 0.0034 | 0.0007 | 1744 | 1963 | 2428 | 506 |
| 15 | 18 | 0.0132 | 0.0136 | 0.0033 | 19186 | 1134 | 5206 | 1263 |
| 20 | 24 | 0.0297 | 0.0192 | 0.0040 | 20881 | 674 | 2514 | 524 |
| 30 | 6 | 0.0889 | 0.0155 | 0.0069 | 101454 | 337 | 76 | 34 |
| 40 | 21 | 0.1412 | 0.0382 | 0.0085 | 80515 | 283 | 145 | 33 |
| C14 Sucrose - Cholestatic (Average) 04 day mice | | | | | | | | |
| 10 | 6 | 0.0186 | 0.0154 | 0.0069 | 832 | 539 | 564 | 252 |
| 20 | 6 | 0.0555 | 0.0258 | 0.0115 | 67384 | 361 | 1099 | 491 |
| 40 | 4 | 0.1921 | 0.0412 | 0.0238 | 730366 | 208 | 73 | 42 |
| C14 Sucrose - Cholestatic (Average) 21 day mice | | | | | | | | |
| 10 | 6 | 0.0267 | 0.0234 | 0.0105 | 2446 | 375 | 816 | 365 |
| 20 | 7 | 0.0424 | 0.0352 | 0.0144 | 7563 | 472 | 557 | 227 |
| 40 | 6 | 0.1798 | 0.0914 | 0.0409 | 60513 | 222 | 212 | 95 |
| C14 Insulin - Cholestatic (Average) 04 day mice | | | | | | | | |
| 10 | 6 | 0.0020 | 0.00051 | 0.0002 | 27 | 4984.355 | 2096 | 937 |
| 20 | 6 | 0.0129 | 0.00508 | 0.0023 | 2534 | 1552.701 | 579 | 259 |
| 40 | 6 | 0.1263 | 0.07355 | 0.0329 | 20134 | 316.708 | 186 | 83 | der was filling with infusate. The period of approximately constant flow (4 minutes-20 minutes) indicates that either the gallbladder was stretching to accommodate the infusion and/or infusate was leaking from the gallbladder lumen.

The plasma [14C] rose steadily during the course of the infusion, consistent with paracellular leakage rather than gallbladder stretch as the explanation of a constant infusion rate. Once the infusion was discontinued paracellular leakage continued, likely due to the combination of a intralumenal-subepithelial pressure gradient and the time required for sucrose to be taken up within venous and/or lymphatic capillaries within the lamina propria.

EXAMPLE 18

Constant Pressure Infusion into Rabbit Gallbladder

Constant pressure infusion to the rabbit gallbladder was evaluated by emptying the gallbladder and securing a silicone catheter (030" ID/065" OD) within the gallbladder lumen. The cystic duct was occluded using microvascular clips with particular care being taken to not occlude the cystic artery or vein. [14C]-sucrose (3.8 μCi/ml) was administered at a constant pressure of 40 mm Hg for 20 minutes using the gallbladder catheter and the constant-pressure device described above. A heparinized internal jugular catheter was utilized to obtain plasma samples. Plasma samples were obtained at different timepoints and evaluated in a scintillation counter (Beckman).

Figure 43:
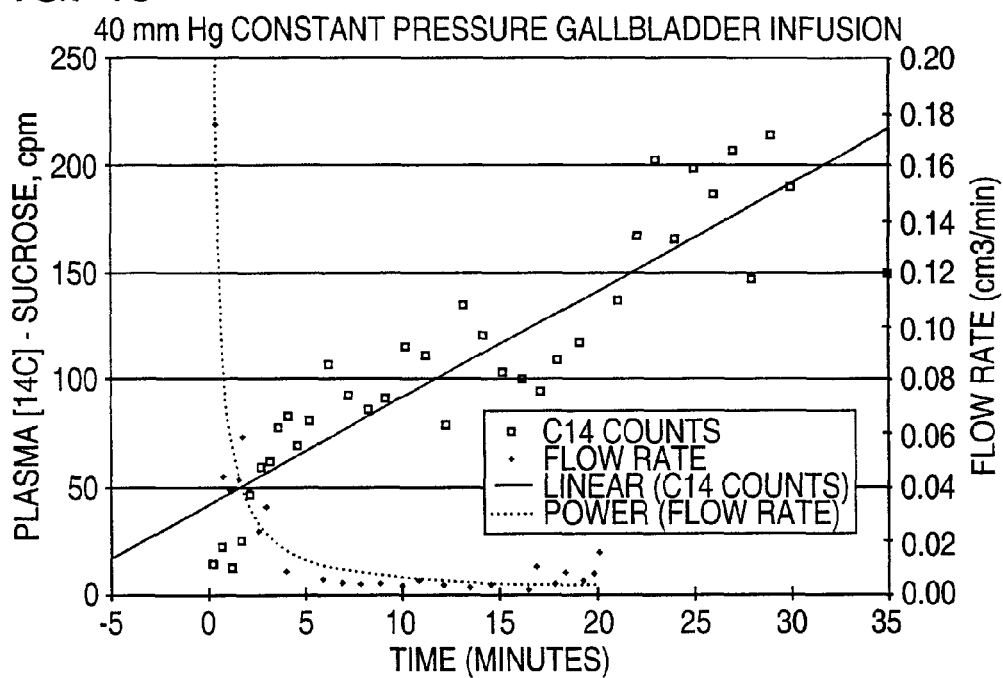
FIG. 43 is a plot of flow rate and sucrose tracer counts in plasma as a function of time for constant-pressure gallbladder infusion.

FIG. 43 is a plot of both flow rate and paracellular leakage (plasma content of [14C]-sucrose) over the course of the experiment. Flow rates were initially high and then rapidly declined to an approximately steady level. The rapid rate of flow with decline was due to the period in which the gallblad-

EXAMPLE 19

Constant Pressure Retrograde Biliary Infusion in Rabbit

A silastic catheter (030" ID/065" OD) was secured within the lumen of the common bile duct with its opening directed in a retrograde direction. [14C]-sucrose (3.8 μCi/ml) was administered at a constant pressure of 20, 30, or 40 mm Hg for 20 minutes using the common bile duct catheter and the pressure device described above. A heparinized internal jugular catheter was utilized to obtain plasma samples. Plasma samples were obtained at different timepoints and evaluated in a scintillation counter (Beckman).

Figure 44:
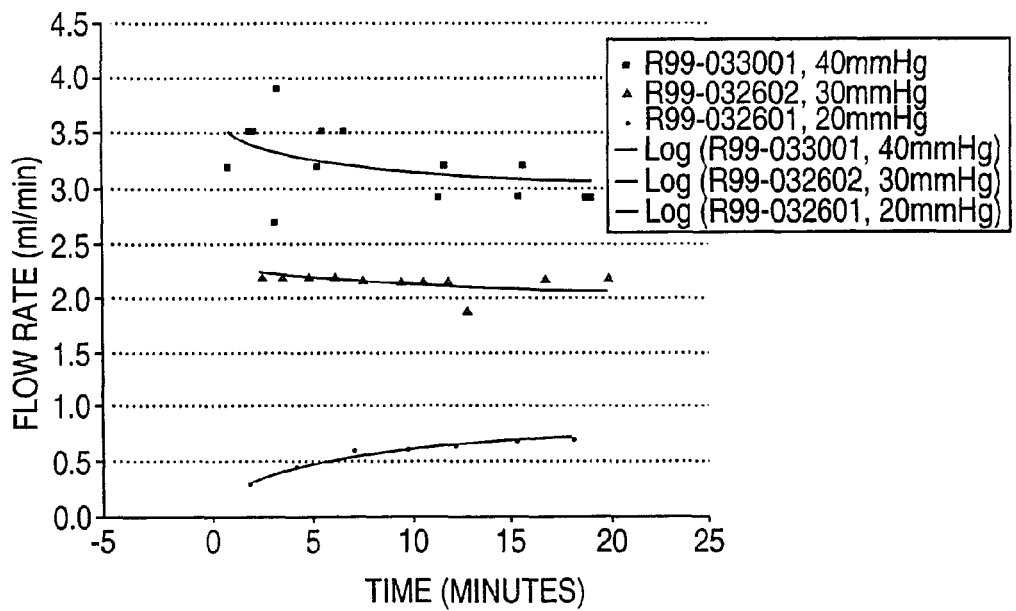
FIG. 44 is a graph of flow rate over time at 20, 30, and 40 mm Hg constant pressure infusion.
Figure 45:
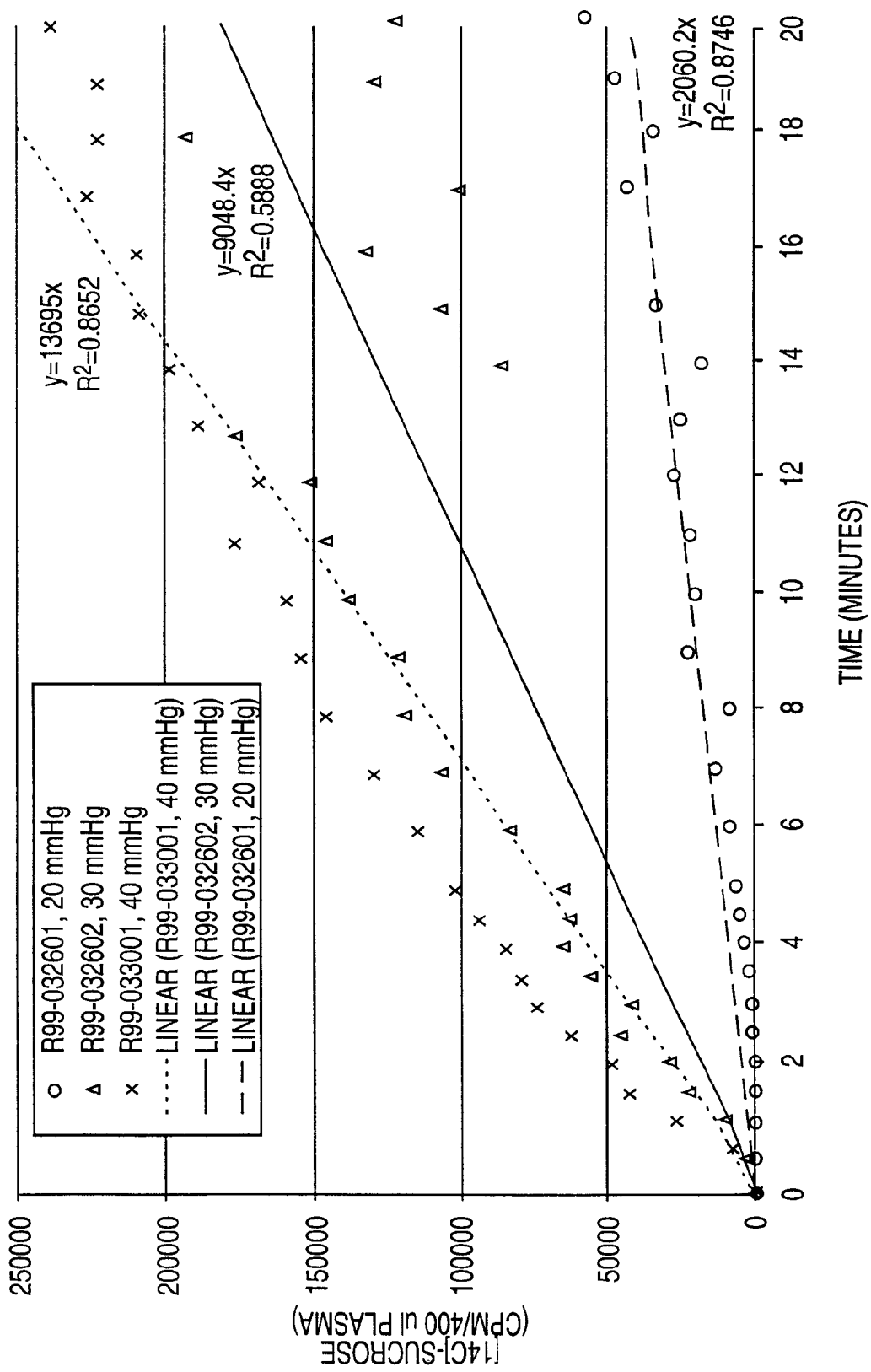
FIG. 45 is a graph of paracellular leakage over time at 20, 30, and 40 mm Hg constant pressure infusion.

FIG. 44 is a graph of flow rate over time at 20, 30, and 40 mm Hg constant pressure infusion. FIG. 45 is a graph of paracellular leakage over time at 20, 30, and 40 mm Hg constant pressure infusion. Flow rates were proportional to infusion pressure and remained fairly constant once a steady state value was achieved. Paracellular leakage was also proportional to infusion pressure.

EXAMPLE 20

Vascular Catheter

Figure 46A:
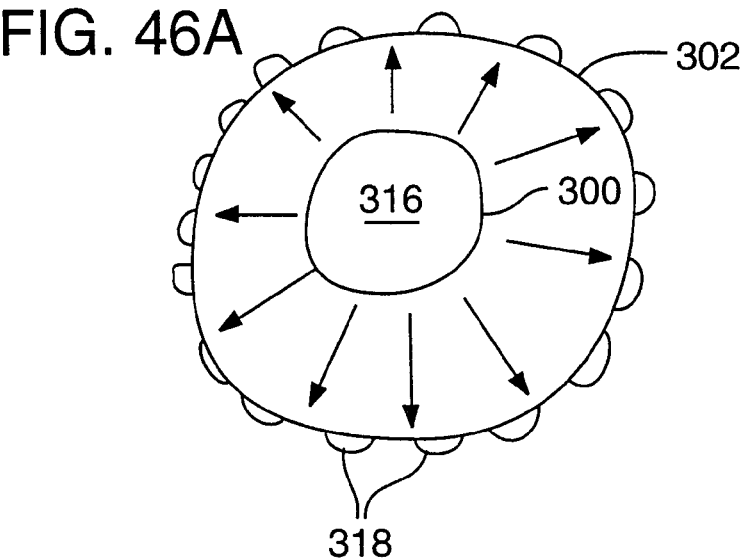
FIG. 46A is a schematic cross-section of a catheter positioned within a body lumen for use in the methods of the present invention.
Figure 46B:
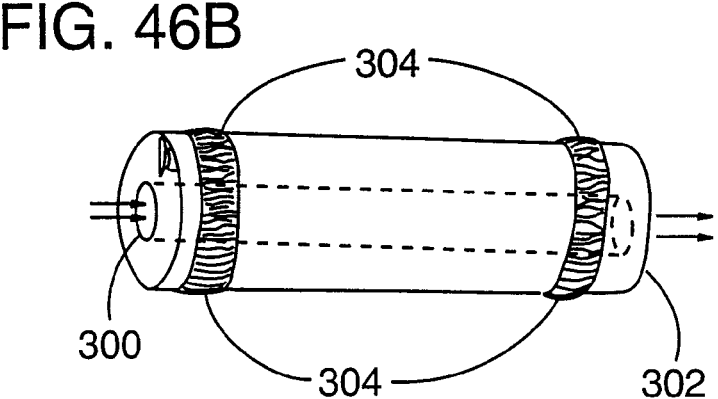
FIG. 46B is a longitudinal view of the body lumen and catheter of FIG. 46A.

Constant pressure intralumenal delivery permits the focused application of defined pressures to the inner surface of a vessel lumen. FIG. 46A is a schematic cross-section of a catheter 300 positioned in a body lumen 302 surrounded by smooth muscle cells 318. The catheter 302 allows the controlled application of pressure in the direction indicated by the arrows. The catheter includes a lumen 316 to permit blood to flow through the vessel and continue through the circulation while a defined vascular segment is isolated, by balloons on the circumference of the catheter, and undergoes constant pressure infusion. FIG. 46B shows a partial longitudinal view of the catheter 300 within the body lumen 302 with the balloons 304 inflated. Blood flows through a lumen of the catheter 300 in the direction shown by the arrows.

This infusion provided by the catheter 300 may be used to compress an atherosclerotic plaque or to disrupt the tight junctions between surface endothelial cells, thereby permitting infusate to move along a pressure gradient to deeper histological cells, such as vascular smooth muscle cells. Alternatively, a pharmacological or other agent may be applied to the apical surface in order to increase surface permeability. A pressure gradient may then be utilized to deliver molecules to the deeper histological compartments.

Figure 47:
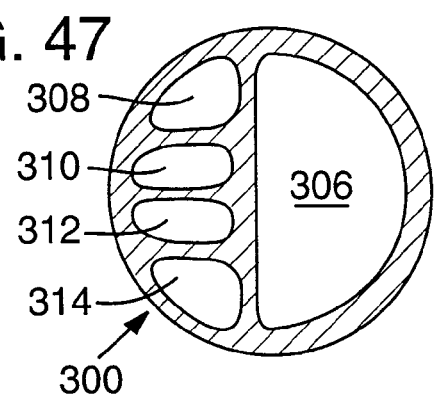
FIG. 47 is a cross-section of an example of a multiple lumen catheter useful in the methods of the present invention.

The catheter preferably includes multiple lumens, such as those shown, for example, in the cross-section of FIG. 47. The largest lumen 306 would desirably be used for blood flow, while smaller lumens 308, 310, 312, and 314 would be employed for purposes such as (1) inflating and deflating the balloons, (2) delivering therapeutic substance(s) to the space sealed off by the balloons, (3) detecting the pressure in the space sealed off by the balloons, (4) utilizing ultrasound or other means to detect volume of the space sealed off by the balloons.

EXAMPLE 20

Combination of Pharmacological and/or Physical Intervention with Pressure Gradient A pharmacological substance that increases (or decreases) disruption of tight junctions, and/or a physical treatment having the same effect, may be employed in combination with a pressure gradient produced and employed according to the methods of the present invention so as to enhance the tissue- or cell-specific delivery of a therapeutic agent. For example, electrical or acoustic disruption, as well as pharmacological disruption of tight junctions may permit more effective delivery of a therapeutic agent to subepithelial or subendothelial tissue compartments. An example of pharmacological creation of a pathway through which molecules may move along a pressure gradient is the use of zona occludens toxin, described in U.S. Pat. Nos. 5,864,014, 4,827,534, and 5,664,389.

EXAMPLE 21

Measurement of Capacitance

The above-described methods of constant pressure intralumenal delivery may be combined with methods for measuring the expansion of a viscous, duct, or blood vessel to evaluate the effective volume of the tissue compartment. Such methods may include the use of intralumenal ultrasound, which has been described for the evaluation of tissue compartment diameters. This allows fairly direct measurement of capacitance, i.e., the compartment volume function of the pressure in the compartment. Assessment of capacitance prior to therapeutic infusion could allow better selectivity in delivery to specific tissues, reducing the variations attributable to individual physiology. Intralumenal ultrasound or other methods of assessing the tissue compartment may also be combined with pressure-mediated delivery to permit evaluation of the depth of delivery of a therapeutic agent.

The methods and devices of the present invention can be used, with appropriate modifications, to delivery of agents into the ducts of epithelial organs, such as those of the parotid and salivary glands. In any anatomic site, the therapeutic substance can include gene therapy vectors, such as an adenovirus, adeno-associated virus, retrovirus, herpes simplex virus, lentiviruses, hybrid viruses, DNA plasmids, molecular conjugates and liposomes. Diseases that can be treated with gene therapy using these methods include metabolic diseases (including disorder of cholesterol metabolism), hepatic fibrosis (with a gene that expresses the anti-inflammatory gene IL-10), hepatocellular, pancreatic, gallbladder colon, urinary bladder, uterine, ovarian, cervical, ureteral, renal, salivary gland, or parotid gland carcinoma (with a gene that expresses a proinflammatory gene, or other antineoplastic gene, such as the adenoviral Ela gene), sclerosing cholangitis or primary biliary cirrhosis (using expression of an anti-inflammatory agent, such as IL-10), cystic fibrosis (by expressing the CFTR gene delivered preferentially to the epithelia of the hepatobiliary tree, pancreas and intestine), and hepatobiliary infections of the type seen with immunosuppression (for example by expression of a fungal gene delivered preferentially to the hepatobiliary epithelium).

The methods and devices of the present invention can be used, with appropriate modifications, for the delivery of agents into the lumen of vascular structures, such as arteries or veins. Similarly, the methods and devices of the present invention may be used, with appropriate modification, for delivery of agents into lymphatic vessels, such as the thoracic duct. glands. In any anatomic site, the therapeutic substance can include gene therapy vectors, such as an adenovirus, adeno-associated virus, retrovirus, herpes simplex virus, lentiviruses, hybrid viruses, DNA plasmids, molecular conjugates and liposomes. Diseases that can be treated with gene therapy using these methods include prevention of restenosis following vascular grafting or angioplasty (using genes that expresses the anti-inflammatory gene IL-10 or other genes that prevent neointimal thickening).

In certain embodiments, the methods and devices create a pressure gradient for the purpose of delivery of therapeutic agents, for example a pressure gradient where the pressure is greater on the inside of a structure than the deeper histological components of the structure such that flow is directed from internal toward external. In the case of a epithelial organ or duct this pressure gradient may be created such that the intraluminal pressure is greater than the pressure in the lamina propria, which is greater than the pressure in the muscle layer, which is greater than the pressure in the serosa. In the case of a vascular structure the pressure gradient may be created such that the intraluminal pressure is greater than the pressure in the media or adventitia. Establishment of the gradient may be combined with techniques for accessing more internal layers, such as removal of epithelial cells, endothelial cells, or atherosclerotic plaque followed by application of an internal to external pressure gradient. Alternatively, the pressure gradient may be established such that pressure on the more external components of the structure is greater than the pressures inside the structure, so that flow is directed from external toward internal regions. In the case of a epithelial organ or duct this pressure gradient would be created such that the pressure in the serosa is greater than the pressure in the muscle layer, lamina propria or within the lumen (or that the gradient is established in that direction). In the case of a vascular structure the pressure gradient would be created such that the pressure in the adventitia is greater than the pressure within more internal structures. In the case of a nerve, the pressure gradient would be applied to the epineurium or other structure and directed toward the inner portion of nerve fibers. Establishment of the gradient may be combined with techniques for accessing more internal layers, such as stripping of the adventitia, epineurium, or serosa followed by application of an external-internal pressure gradient.

As used in this specification, the term "therapeutic agent" includes a diagnostic agent used for the purpose of making a medical diagnosis. "Predetermined" pressures, flows, and volumes may either be determined in a particular patient, or estimated from pre-existing data. The term "non-vascular" means "not a blood vessel." However the term "vascular" includes both lymphatic and blood vessels. "Surgical" includes any technique for accessing the interior of the body or its organs, and includes conventional surgical access, as well as endoscopic or laparoscopic procedures. A "lumen" is a cavity or channel within a hollow or tubular organ (such as the gall bladder or a duct). "Hepatic" refers to the liver, "biliary" refers to the gallbladder or bile ducts, and "hepatobiliary" refers to the gallbladder, liver, and bile ducts (including ductules) that collect the bile and communicate between the two organs. An "isolated" or "pressurized" chamber within an organ does not require a fluid-tight seal, but only reduction of fluid flow from the organ chamber to a sufficient extent to achieve adequate pressure in the organ chamber.

A "threshold" pressure is one at which epithelial delivery begins, sub-epithelial delivery begins, systemic delivery begins, or some other type of delivery (such as a desired mix of the aforementioned types of delivery) begins. A particular example of a threshold is the peak pressure that is developed in a closed organ space, and which represents microanatomic disruption that leads to substantial subepithelial delivery.

As used in the following claims, the singular includes the plural. Hence "a" includes one or more.

Having illustrated and demonstrated the principles of the invention in several embodiments, it should be apparent to those skilled in the art that these embodiments can be modified in arrangement and detail without departing from such principles.

We claim:

1. A method for delivery of a therapeutic or diagnostic agent, the method comprising:
    forming a substantially closed chamber within or adjacent to an organ,
    administering a test fluid into the closed chamber at a given flow rate and measuring a peak pressure at which delivery to a region deep to a superficial histological layer within the organ commences,
    administering a fluid comprising a therapeutic or diagnostic agent to the histological layer within an organ, by forming a substantially closed chamber within or adjacent the organ, and delivering the fluid at a preselected pressure, flow rate or volume of administration to direct delivery of the fluid to the histological layer of the organ,
    wherein controlling at least one of the pressure, the flow rate or the volume comprises administering the fluid (1) as part of a fluid flow into the closed chamber during which the peak pressure is not exceeded, when selective delivery only to a superficial histological layer is desired, or (2) as part of a fluid flow into the closed chamber during which the peak pressure is equaled or exceeded, when selective delivery to a region deep to the superficial histological layer is desired.

2. The method of claim 1, wherein the histological layer is selected from the group consisting of (a) an epithelial or subepithelial layer; (b) an endothelial or subendothelial layer; (c) a serosa or subserosal layer; and (d) an adventitial or subadventitial layer.

3. The method of claim 2 wherein the histological layer is an epithelial or subepithelial layer.

4. The method of claim 1, wherein the organ comprises a blood vessel or a hollow viscus, and an interior volume of the blood vessel or hollow viscus is isolated to control the predetermined pressure, flow rate or volume of administration.

5. The method of claim 1, wherein an external area of the organ is isolated to control the preselected pressure, flow rate, or volume of administration.

6. The method of claim 1 further comprising:
    forming a closed chamber within the organ by forming a closed chamber within a hollow organ space within the organ or forming a closed chamber around the organ or a portion of the organ; and
    administering the fluid into the hollow organ space or the chamber around the organ.

7. The method of claim 6 wherein the hollow organ space is in an organ that includes a neoplasm, and the agent comprises an anti-neoplastic agent or a pro-inflammatory cytokine.

8. The method of claim 6 wherein the hollow organ space comprises:
    (a) a portion of the hepatobiliary system adjacent to or involved with hepatic fibrosis, primary biliary cirrhosis or sclerosing cholangitis, and the therapeutic or diagnostic agent comprises an anti-inflammatory agent; or
    (b) a portion of intestine affected with Crohn's disease, and the therapeutic or diagnostic agent comprises an anti-inflammatory agent for delivery at a sufficient pressure to introduce the therapeutic or diagnostic agent to a subepithelial lamina propria of the intestinal wall; or
    (c) a portion of hepatobiliary tract, the superficial layer comprises epithelial cells lining the hepatobiliary tract, and the region deep to the superficial layer comprises at least one of sinusoids of the liver, Space of Disse, lamina propria, and smooth muscle cells of the gall bladder; or
    (d) a portion of the pancreas affected by pancreatic adenocarcinoma and the therapeutic agent comprises an anti-neoplastic agent or a pro-inflammatory agent or an agent that promotes the formation of blood vessels; and the agent is delivered to either the epithelial cells or subepithelial cells or both; or
    (e) a portion of the esophagus affected by esophageal carcinoma and the therapeutic agent comprises an anti-neoplastic agent or a pro-inflammatory agent; or
    (f) a portion of the prostate gland affected by prostatic carcinoma and the therapeutic agent comprises an anti-neoplastic agent or a pro-inflammatory agent; or
    (g) a portion of the urinary bladder affected by carcinoma and the therapeutic agent comprises an anti-neoplastic agent or a pro-inflammatory agent delivered to either the superficial epithelial cells, the lamina propria, any or all of the circular and longitudinal muscle layers, and/or the serosa.

9. The method of claim 1, wherein controlling the liquid pressure comprises administering the liquid at a constant pressure.

10. The method of claim 1, wherein forming a closed chamber within a hollow organ space comprises accessing the hollow organ space, substantially occluding an outlet therefrom, and draining the hollow organ space to remove bodily fluids that may interfere with the action of the therapeutic or diagnostic agent.

11. The method of claim 1 wherein controlling at least one of the pressure, the flow rate, and the volume comprises substantially occluding an outlet from a hollow organ space, and varying the flow rate or volume so as to obtain a desired pressure.

12. The method of claim 1 wherein the closed chamber comprises a hollow organ space, and controlling at least one of the pressure, the flow rate, and the volume comprises administering the fluid comprising the therapeutic or diagnostic agent at a pressure only slightly above a normal physiologic intralumenal pressure in the hollow organ space, at a pressure sufficient to achieve selective delivery substantially only to the histological layer.

13. The method of claim 12 wherein the fluid administered slightly above a normal physiologic intralumenal pressure is administered at a pressure no more than about 2-5 mg Hg above the normal physiologic intralumenal pressure in the hollow organ space.

14. The method of claim 1 wherein the closed chamber comprises a hollow organ space, and the method further comprises isolating a portion of the hollow organ space within the body to form the substantially closed chamber.

15. The method of claim 14 wherein isolating the portion of the hollow organ space comprises occluding a duct draining the organ.

16. The method of claim 15 wherein the isolated portion of the hollow organ space comprises the hepatobiliary tract.

17. The method of claim 14 wherein the isolated portion of the hollow organ space comprises the gall bladder and/or ducts of the hepatobiliary tract.

18. The method of claim 14 wherein the isolated portion of the hollow organ space comprises hepatic bile ducts or at least a portion of intestine.

19. The method of claim 1 wherein the therapeutic or diagnostic agent comprises at least one of a chemotherapy agent, a pro-inflammatory agent, an anti-inflammatory agent, and a genetic vector.

20. The method of claim 1, wherein the fluid is administered at a flow rate of 0.066-960 µl/sec.

21. The method of claim 1, wherein the fluid is administered at a flow rate of less than 1000 µl/sec.

22. The method of claim 21, wherein the fluid is administered at a pressure of no more than about 500 mm Hg.

23. The method of claim 22, wherein the fluid is administered at substantially constant pressure.

24. The method of claim 23, wherein the organ is non-vascular, and the fluid is administered at a substantially constant pressure of about 5-100 mm Hg.

25. The method of claim 23, wherein the organ is vascular, and the fluid is administered at a substantially constant pressure of about 5-400 mm Hg.

26. The method of claim 1, further comprising administering a pharmacological substance that improves opening of tight junctions.

27. The method of claim 1, wherein the organ is a hollow viscus, and the method further comprises partially filling the hollow viscus with an inflatable space occupier before administering the fluid.

28. The method of claim 1, wherein the pressure is controlled by creating a pressure gradient in a solid portion of the organ, wherein the pressure gradient is preselected to deliver the agent to the predetermined region.

29. The method of claim 28, wherein the pressure gradient is highest inside the organ.

30. The method of claim 28, wherein the pressure gradient is highest outside the organ.

31. The method of claim 1, wherein the histological layer includes polarized epithelial cells.

32. The method of claim 1, wherein the organ includes a hollow viscus lined with polarized epithelial cells, and the therapeutic or diagnostic agent is administered to the apical surfaces of the polarized epithelial cells.

33. The method of claim 1, wherein the delivery of the fluid temporarily opens inter-epithelial tight junctions thereby creating a pressure gradient along which therapeutic or diagnostic molecules are delivered to a subepithelial tissue compartment.

34. The method of claim 1, wherein forming a substantially closed chamber within or adjacent the organ comprises forming a closed pressure system.

35. The method of claim 1, wherein the delivery pressure is 2 to 5 mm Hg above normal physiologic intraluminal pressure.

36. The method of claim 1, wherein administering the fluid to a histological layer comprises treating or diagnosing the histological layer.

37. The method of claim 36, wherein the histological layer is treated or diagnosed substantially without damaging the histological layer.

38. A method for selective administration of a therapeutic or diagnostic substance, the method comprising:
    isolating a hollow organ space;
    one or more times, introducing a test fluid into the hollow organ space at a preselected flow rate; and
    one or more times, administering a test solution to determine a pressure at which leakage across epithelial or endothelial tight junctions occurs; and
    administering a liquid including the therapeutic or diagnostic substance by introducing the liquid into the isolated hollow organ space, during which the pressure is not exceeded with the purpose of preferentially delivering the substance to an epithelial layer of the hollow organ space, or during which the peak pressure is exceeded with the purpose of preferentially delivering the substance to a subepithelial layer of the hollow organ space.

39. A method of determining the delivery pressure for selective administration of a therapeutic or diagnostic substance, the method comprising:
    isolating a hollow organ space;
    one or more times, introducing a test fluid into the hollow organ space at a preselected approximately constant pressure;
    one or more times, measuring the infusion rate of the administered fluid as the test fluid is introduced; and
    administering a liquid including a test solution into the hollow organ space and determining a flow rate at which paracellular leakage across endothelial or epithelial tight junctions occurs.

* * * * *